United States Patent
Tucker-Schwartz et al.

(10) Patent No.: US 11,927,592 B2
(45) Date of Patent: Mar. 12, 2024

(54) COMPOSITIONS AND METHODS FOR CARRYING OUT ASSAY MEASUREMENTS

(71) Applicant: Meso Scale Technologies, LLC., Rockville, MD (US)

(72) Inventors: Alexander K. Tucker-Schwartz, Bethesda, MD (US); George Sigal, Rockville, MD (US)

(73) Assignee: MESO SCALE TECHNOLOGIES, LLC., Rockville, MD (US)

(*) Notice: Subject to any disclaimer, the term of this patent is extended or adjusted under 35 U.S.C. 154(b) by 0 days.

(21) Appl. No.: 17/813,722

(22) Filed: Jul. 20, 2022

(65) Prior Publication Data

US 2022/0373554 A1    Nov. 24, 2022

Related U.S. Application Data

(63) Continuation of application No. 17/264,489, filed as application No. PCT/US2019/068293 on Dec. 23, 2019.

(60) Provisional application No. 62/787,892, filed on Jan. 3, 2019.

(51) Int. Cl.
*G01N 33/58* (2006.01)
*G01N 21/66* (2006.01)

(52) U.S. Cl.
CPC .............. *G01N 33/58* (2013.01); *G01N 21/66* (2013.01); *G01N 2458/30* (2013.01)

(58) Field of Classification Search
CPC .............. G01N 21/66; G01N 2458/30; G01N 33/5306; G01N 33/54326; G01N 33/5438; G01N 33/58
See application file for complete search history.

(56) References Cited

U.S. PATENT DOCUMENTS

| | | | |
|---|---|---|---|
| 5,093,268 A | 3/1992 | Leventis et al. |
| 5,147,806 A | 9/1992 | Kamin et al. |
| 5,238,808 A | 8/1993 | Bard et al. |
| 5,240,863 A | 8/1993 | Shibue et al. |
| 5,308,754 A | 5/1994 | Kankare et al. |

(Continued)

FOREIGN PATENT DOCUMENTS

| | | | | |
|---|---|---|---|---|
| AU | 2008200361 A1 | * | 2/2008 | ............. C12Q 1/485 |
| CN | 101532961 A | | 9/2009 | |

(Continued)

OTHER PUBLICATIONS

Chen, Yu et al., "A simple and versatile paper-based electrochemiluminescence biosensing platform for hepatitis B virus surface antigen detection," Biochemical Engineering Journal 129:1-6 (2017).

(Continued)

*Primary Examiner* — Jennifer Wecker

(74) *Attorney, Agent, or Firm* — MEDLER FERRO WOODHOUSE & MILLS PLLC

(57) ABSTRACT

The present disclosure provides compositions, reagents, kits, systems, system components, and methods for performing assays. More particularly, the disclosure relates to an assay composition for detecting luminescence, which comprises an alkyl diethanolamine, for example, N-butyldiethanolamine (BDEA). In emodiments, the assay composition comprises 2-dibutylaminoethanol (BDAE).

16 Claims, 23 Drawing Sheets

(56) References Cited

U.S. PATENT DOCUMENTS

| | | |
|---|---|---|
| 5,324,457 A | 6/1994 | Zhang et al. |
| 5,589,136 A | 12/1996 | Northrup et al. |
| 5,591,581 A | 1/1997 | Massey et al. |
| 5,597,910 A | 1/1997 | Gudibande et al. |
| 5,641,623 A | 6/1997 | Martin |
| 5,643,713 A | 7/1997 | Liang et al. |
| 5,679,519 A | 10/1997 | Oprandy |
| 5,705,402 A | 1/1998 | Leland et al. |
| 5,714,089 A | 2/1998 | Bard et al. |
| 5,731,147 A | 3/1998 | Bard et al. |
| 5,776,672 A | 7/1998 | Hashimoto et al. |
| 5,786,141 A | 7/1998 | Bard et al. |
| 5,846,485 A | 12/1998 | Leland et al. |
| 5,866,434 A | 2/1999 | Massey et al. |
| 5,935,779 A | 8/1999 | Massey et al. |
| 5,993,740 A | 11/1999 | Niiyama et al. |
| 6,066,448 A | 5/2000 | Wohlstadter et al. |
| 6,090,545 A | 7/2000 | Wohlstadter et al. |
| 6,136,268 A | 10/2000 | Ala-Kleme et al. |
| 6,140,045 A | 10/2000 | Wohlstadter et al. |
| 6,207,369 B1 | 3/2001 | Wohlstadter et al. |
| 6,316,607 B1 | 11/2001 | Massey et al. |
| 6,451,225 B1 | 9/2002 | Leland et al. |
| 6,808,939 B2 | 10/2004 | Sigal et al. |
| 6,919,173 B2 | 7/2005 | Tsionsky et al. |
| 6,977,722 B2 | 12/2005 | Wohlstadter et al. |
| 7,288,410 B2 | 10/2007 | Tsionsky et al. |
| 7,491,540 B2 | 2/2009 | Tsionsky et al. |
| 7,842,246 B2 | 11/2010 | Wohlstadter et al. |
| 8,785,201 B2 | 7/2014 | Tsionsky et al. |
| 9,416,150 B2 | 8/2016 | Bergmann et al. |
| 9,731,297 B2 | 8/2017 | Glezer et al. |
| 9,891,221 B2 | 2/2018 | Tsionsky et al. |
| 10,753,934 B2 | 8/2020 | Tsionsky et al. |
| 2012/0178091 A1 | 7/2012 | Glezer et al. |
| 2012/0190589 A1 | 7/2012 | Anderson et al. |
| 2018/0364175 A1 | 12/2018 | Josel et al. |
| 2021/0109100 A1 | 4/2021 | Tsionsky et al. |

FOREIGN PATENT DOCUMENTS

| | | | |
|---|---|---|---|
| CN | 106124753 A | 11/2016 | |
| CN | 106526183 A | 3/2017 | |
| CN | 109444116 A * | 3/2019 | ............. C12Q 1/485 |
| CN | 108698047 B | 4/2022 | |
| JP | H08502586 A | 3/1996 | |
| JP | 2001021560 A | 1/2001 | |
| WO | 1990/005296 A1 | 5/1990 | |
| WO | 1996/021154 A1 | 7/1996 | |
| WO | 1997/036931 A1 | 10/1997 | |
| WO | 1998/012539 A1 | 3/1998 | |
| WO | 1998/057154 A1 | 12/1998 | |
| WO | 1999/014599 A1 | 3/1999 | |
| WO | 1999/063347 A2 | 5/1999 | |
| WO | 1999/032662 A1 | 7/1999 | |
| WO | 1999/058962 A1 | 11/1999 | |
| WO | 2000/003233 A1 | 1/2000 | |
| WO | 2003/023380 A1 | 3/2003 | |

OTHER PUBLICATIONS

Debad, Jeff et al., "Clinical and Biological Applications of ECL" in Electrogenerated Chemiluminescence, 1st Edition, 2004, CRC Press; pp. 43-78.

Han, Shuang et al., "Effect of Hydroxyl and Amino Groups on Electrochemiluminescence Activity of Tertiary Amines at Low tris(2,2'-bipyridyl)ruthenium(II) Concentrations" (Abstract), Talanta 81(1-2):44-47 (2010).

International Search Report dated Apr. 22, 2020 in International Appl. No. PCT/US2019/068293.

Kirschbaum-Harriman, Stefanie et al., "Improving ruthenium-based ECL through nonionic surfactants and tertiary amines," Analyst 142(14):2648-2653 (2017).

Kirschbaum-Harriman, Stefanie et al., "Signal enhancement and low oxidation potentials for miniaturized ECL biosensors via N-butyldiethanolamine", Analyst 142(13):2469-2474 (2017).

Kitte, Shimeles Addisu et al., "Electrogenerated chemiluminescence of tris(2,2'-bipyridine) ruthenium(II) using N-(3-aminopropyl)diethanolamine as coreactant", Anal Bioanal Chem 408(25):7059-7065 (2016).

Hu et al., "Applications and trends in electrochemiluminescence," Chemical Society Reviews, 39: 3275-3304 (2010).

Wang et al., "Label free bifunctional electrochemiluminescence aptasensor for detection of adenosine and lysozyme," Electrochimica Acta, 76: 416-423 (2012).

Final Office Action in U.S. Appl. No. 17/264,489, United States Patent and Trademark Office, dated Jan. 29, 2024.

* cited by examiner

|  | Assay | Signal | | Signal (Normalized) | | CV (Intraplate) | | CV (Interplate) | |
|---|---|---|---|---|---|---|---|---|---|
|  |  | TPA | BDEA | TPA | BDEA | TPA | BDEA | TPA | BDEA |
| Mid-Cal | IFN-γ | 11,025 | 12,090 | 100% | 110% | 3.9% | 3.3% | 2.2% | 3.0% |
|  | IL-1β | 59,532 | 58,779 | 100% | 99% | 4.0% | 3.8% | 2.1% | 1.9% |
|  | IL-2 | 42,754 | 45,724 | 100% | 107% | 2.9% | 2.7% | 3.0% | 2.7% |
|  | IL-4 | 25,038 | 27,079 | 100% | 108% | 4.9% | 4.4% | 2.4% | 1.4% |
|  | IL-6 | 32,282 | 31,396 | 100% | 97% | 4.7% | 4.2% | 6.5% | 4.6% |
|  | IL-8 | 18,141 | 17,981 | 100% | 99% | 3.7% | 3.8% | 3.2% | 4.9% |
|  | IL-10 | 22,363 | 25,758 | 100% | 115% | 3.3% | 2.9% | 2.2% | 1.7% |
|  | IL12p70 | 10,515 | 10,829 | 100% | 103% | 6.6% | 6.4% | 3.7% | 2.8% |
|  | IL-13 | 7,977 | 11,148 | 100% | 140% | 5.5% | 4.5% | 3.2% | 3.9% |
|  | TNF-α | 8,639 | 8,329 | 100% | 96% | 4.4% | 4.2% | 2.6% | 2.6% |
|  | Average | 23,827 | 24,623 | 100% | 107% | 4.4% | 4.0% | 3.1% | 3.0% |
| NSB | IFN-γ | 534 | 1,127 | 100% | 211% | 7.3% | 6.4% | 15.0% | 20.9% |
|  | IL-1β | 1,788 | 5,321 | 100% | 298% | 7.5% | 9.6% | 13.8% | 5.6% |
|  | IL-2 | 321 | 592 | 100% | 185% | 14.2% | 6.6% | 16.4% | 10.9% |
|  | IL-4 | 175 | 262 | 100% | 150% | 20.5% | 19.9% | 20.5% | 17.9% |
|  | IL-6 | 215 | 374 | 100% | 174% | 12.4% | 9.6% | 13.4% | 9.9% |
|  | IL-8 | 272 | 421 | 100% | 155% | 9.8% | 9.7% | 17.7% | 17.0% |
|  | IL-10 | 456 | 884 | 100% | 194% | 8.6% | 6.4% | 18.5% | 19.0% |
|  | IL12p70 | 180 | 213 | 100% | 118% | 35.8% | 33.2% | 15.9% | 22.8% |
|  | IL-13 | 155 | 245 | 100% | 158% | 14.6% | 12.9% | 12.4% | 12.5% |
|  | TNF-α | 189 | 331 | 100% | 175% | 20.5% | 11.7% | 14.9% | 17.6% |
|  | Average | 429 | 931 | 100% | 182% | 15.1% | 12.6% | 15.9% | 15.4% |

FIG. 2A

|  | Assay | Signal | | Signal (Normalized) | | CV (Intraplate) | | CV (Interplate) | |
|---|---|---|---|---|---|---|---|---|---|
|  |  | TPA | BDEA+NaCl | TPA | BDEA+NaCl | TPA | BDEA+NaCl | TPA | BDEA+NaCl |
| Mid-Cal | IFN-γ | 8,494 | 7,774 | 100% | 91.5% | 3.3% | 3.4% | 4.2% | 3.6% |
|  | IL-1β | 49,770 | 39,585 | 100% | 79.5% | 3.3% | 3.3% | 3.5% | 4.1% |
|  | IL-2 | 40,845 | 34,365 | 100% | 84.1% | 2.8% | 2.5% | 3.2% | 3.0% |
|  | IL-4 | 31,722 | 28,372 | 100% | 89.4% | 4.4% | 4.8% | 4.7% | 4.9% |
|  | IL-6 | 33,504 | 26,074 | 100% | 77.8% | 4.1% | 3.7% | 6.3% | 5.9% |
|  | IL-8 | 16,029 | 12,887 | 100% | 80.4% | 3.5% | 3.5% | 3.6% | 4.4% |
|  | IL-10 | 22,983 | 21,797 | 100% | 94.8% | 3.4% | 3.1% | 3.9% | 3.3% |
|  | IL12p70 | 9,226 | 8,405 | 100% | 91.1% | 6.5% | 6.1% | 7.3% | 7.3% |
|  | IL-13 | 10,451 | 11,703 | 100% | 112.0% | 4.9% | 3.8% | 5.1% | 4.0% |
|  | TNF-α | 9,048 | 7,132 | 100% | 78.8% | 3.9% | 3.5% | 4.3% | 3.5% |
|  | Average | 23,207 | 19,809 | 100% | 88.0% | 4.0% | 3.8% | 4.6% | 4.4% |
| NSB | IFN-γ | 242 | 367 | 100% | 151.7% | 13.6% | 9.9% | 13.9% | 12.4% |
|  | IL-1β | 1,374 | 1,757 | 100% | 127.9% | 9.1% | 8.7% | 9.7% | 18.3% |
|  | IL-2 | 231 | 214 | 100% | 92.5% | 12.8% | 14.7% | 12.8% | 15.9% |
|  | IL-4 | 124 | 117 | 100% | 94.4% | 27.6% | 28.2% | 28.1% | 30.1% |
|  | IL-6 | 148 | 160 | 100% | 108.4% | 16.2% | 14.6% | 16.7% | 15.8% |
|  | IL-8 | 165 | 172 | 100% | 104.0% | 13.9% | 13.5% | 14.8% | 13.7% |
|  | IL-10 | 198 | 245 | 100% | 123.6% | 14.8% | 13.2% | 15.0% | 14.3% |
|  | IL12p70 | 151 | 172 | 100% | 113.9% | 17.4% | 17.2% | 17.7% | 17.8% |
|  | IL-13 | 120 | 115 | 100% | 95.8% | 19.9% | 21.1% | 20.3% | 21.8% |
|  | TNF-α | 202 | 244 | 100% | 120.7% | 14.4% | 13.9% | 15.1% | 14.4% |
|  | Average | 296 | 356 | 100% | 113.3% | 16.0% | 15.5% | 16.4% | 17.4% |

FIG. 2B

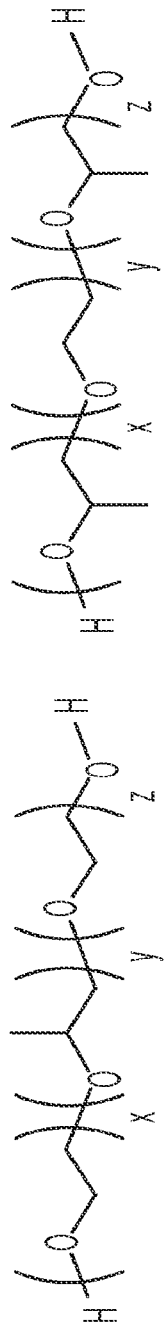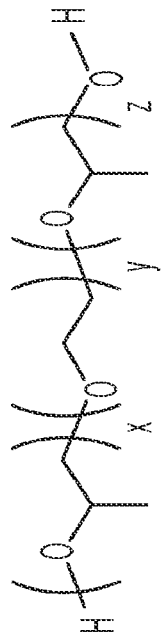
FIG. 5A

Read Buffer liquid/air interfacial tensions

| Surfactant in BDEA Read Buffer | Average $\gamma_{l/a}$ (dyn/cm) | STDEV |
|---|---|---|
| Surfactant free | 53.19 | 0.59 |
| L-121 | 42.06 | 0.23 |
| P407 | 37.19 | 0.24 |
| Tween 20 | 34.16 | 0.33 |
| Brij 58 | 34.05 | 0.43 |
| Decyne-3,4-diol | 33.46 | 0.09 |
| 31R1 | 32.36 | 0.05 |
| Brij L4 (t=35 s) | 32.30 | 0.21 |
| Tetronic 701 | 31.20 | 0.11 |
| P-123 | 29.60 | 0.12 |
| PEG(18)-tridecyl | 29.39 | 0.08 |
| Triton X-100 | 27.20 | 0.10 |

FIG. 5B

| EV Assay | Surfactant in BDEA Read Buffer | Soak Time | ECL | %CV (n=4) | %ECL vs Tween-20 @ t=0 min | %ECL vs soak @ t=15 min |
|---|---|---|---|---|---|---|
| CD9/CD9 | Tween 20 | 0 min | 61933 | 4.1% | 100.0% | 103.9% |
| | | 15 min | 64326 | 3.9% | | |
| | Triton X-100 | 0 min | 809 | 8.7% | 1.3% | 50.4% |
| | | 15 min | 408 | 6.8% | | |
| | Kolliphor® P 407 | 0 min | 58851 | 5.1% | 95.0% | 109.2% |
| | | 15 min | 64275 | 1.4% | | |
| | Pluronic® P-123 | 0 min | 61155 | 3.1% | 98.7% | 99.9% |
| | | 15 min | 61080 | 3.4% | | |
| | Pluronic® L-121 | 0 min | 64643 | 3.1% | 104.4% | 104.1% |
| | | 15 min | 67263 | 2.3% | | |
| | Pluronic® 31R1 | 0 min | 63193 | 2.9% | 102.0% | 96.5% |
| | | 15 min | 60963 | 3.6% | | |
| | Tetronic 701 | 0 min | 59875 | 0.9% | 96.7% | 101.9% |
| | | 15 min | 61002 | 5.2% | | |
| | 2,4,7,9-Tetramethyl-5-decyne-4,7-diol ethoxylate | 0 min | 60697 | 1.3% | 98.0% | 104.6% |
| | | 15 min | 63506 | 4.4% | | |
| | PEG(18) tridecyl ether | 0 min | 62710 | 2.2% | 101.3% | 105.1% |
| | | 15 min | 65897 | 4.3% | | |
| | Brij® L4 | 0 min | 60163 | 2.0% | 97.1% | 99.6% |
| | | 15 min | 59923 | 1.9% | | |
| | Brij® C10 | 0 min | 49150 | 5.7% | 79.4% | 43.7% |
| | | 15 min | 21455 | 9.8% | | |
| | Brij® 58 | 0 min | 60936 | 4.2% | 98.4% | 95.1% |
| | | 15 min | 57960 | 3.2% | | |
| | Brij® S20 | 0 min | 62097 | 2.1% | 100.3% | 87.0% |
| | | 15 min | 54053 | 3.9% | | |
| | Brij® S10 | 0 min | 63885 | 4.3% | 103.2% | 78.9% |
| | | 15 min | 50430 | 2.5% | | |

FIG. 7

|  |  | Average %ECL loss over 39-652 pg/ml cal ||||||
|  |  | MSD T2x ||| BDEA |||
| Capture | Detect | 0 min | 5 min | 10 min | 0 min | 5 min | 10 min |
| --- | --- | --- | --- | --- | --- | --- | --- |
| 4880-B18-1 | 4883-C28-2 | 0% | 41% | 63% | 0% | 26% | 43% |
| 4883-C28-2 | 4880-B18-1 | 0% | 20% | 32% | 0% | 2% | 2% |
| 4883-C28-2 | 4882-A54-1 | 0% | 46% | 68% | 0% | 46% | 69% |
| 4883-C69-2 | 4882-A54-1 | 0% | 48% | 69% | 0% | 51% | 67% |
| 4883-C69-2 | 4883-G74-3 | 0% | 17% | 33% | 0% | 8% | 15% |
| 4883-C69-2 | 4883-J01-1 | 0% | 38% | 60% | 0% | 32% | 53% |

FIG. 9A

|  |  | Average %ECL loss over 10-156 pg/ml cal ||||||
|  |  | MSD T2x ||| BDEA |||
| Capture | Detect | 0 min | 5 min | 10 min | 0 min | 5 min | 10 min |
| --- | --- | --- | --- | --- | --- | --- | --- |
| 512004 | 507602 | 0% | 9% | 19% | 0% | 3% | 6% |
| 512004 | 4390-B35-1 | 0% | 66% | 80% | 0% | 54% | 71% |
| 512004 | 558088 | 0% | 11% | 20% | 0% | 3% | 10% |
| 507602 | 512004 | 0% | 6% | 12% | 0% | 1% | 4% |
| CABT-WN1726 | 4390-B35-1 | 0% | 71% | 83% | 0% | 59% | 73% |
| CABT-WN1726 | 507602 | 0% | 8% | 19% | 0% | -1% | 3% |
| CABT-WN1726 | 4390-F63-4 | 0% | 51% | 72% | 0% | 34% | 54% |
| 130-096-860 | 4390-B35-1 | 0% | 68% | 80% | 0% | 54% | 69% |
| 4365-A26-3 | 4365-A95-1 | 0% | 33% | 54% | 0% | 21% | 39% |

FIG. 9B

|  |  | Average %ECL loss over 195 pg/ml cal |  |  |  |  |  |
|---|---|---|---|---|---|---|---|
|  |  | MSD T2x |  |  | BDEA |  |  |
| Capture | Detect | 0 min | 5 min | 10 min | 0 min | 5 min | 10 min |
| 4945-A82-7 | AF1750 | 0% | 43% | 61% | 0% | 11% | 28% |
| 4945-A82-7 | 4942-D39-6 | 0% | 43% | 63% | 0% | 11% | 24% |

FIG. 9C

|  |  | Average %ECL loss over 1-4 pg/ml |  |  |  |  |  |
|---|---|---|---|---|---|---|---|
|  |  | MSD T2x |  |  | BDEA |  |  |
| Capture | Detect | 0 min | 5 min | 10 min | 0 min | 5 min | 10 min |
| 4680-G17-2 | 4681-B70-5 | 0% | 38% | 59% | 0% | 20% | 34% |

FIG. 9D

COMPOSITIONS AND METHODS FOR CARRYING OUT ASSAY MEASUREMENTS

1. FIELD OF THE DISCLOSURE

This application relates to compositions for use in assays, particularly in electrochemiluminescent assays, and methods of using the same. Reference is made to U.S. Pat. Nos. 6,919,173; 7,288,410; 7491,540; and 8,785,201, each of which are hereby incorporated by reference.

2, BACKGROUND OF THE DISCLOSURE

There are a number of commercially available instruments that utilize electrochemiluminescence (ECL) for analytical measurements. Examples of ECL labels include: i) luminescent organometallic compounds, for example, compounds containing Ru, Os, Ir, Re or a Lanthanide metal such as the it is-bipyridyl-ruthenium (RuBpy) moiety, ii) luminol and related compounds, and iii) noble-metal nanoclusters, for example, gold nanoclusters with the general formula $Au_n(SR)_m$ where n and m are integers (for example, n and m between 18 and 144). Species that participate with the ECL label in the ECL process are referred to herein as ECL coreactants. Commonly used coreactants include tertiary amines (e.g., see U.S. Pat. No. 5,846,485, herein incorporated by reference), oxalate, and persulfate for ECL from RuBpy and hydrogen peroxide for ECL from luminol (see, e.g., U.S. Pat. No. 5,240,863), The light generated by ECL labels can be used as a reporter signal in diagnostic procedures (Bard et al., U.S. Pat. No. 5,238,808). For instance, an ECL, label can be covalently coupled to a binding agent such as an antibody, antigen, nucleic acid, receptor, ligand, or small molecule; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels. ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731.147; 6,066,448; 6,136,268; 5,776,672; 5,308,754; 5,240,863; 6,207,369 and 5,589,136 and Published PCT Nos. WO99/63347; WO00/03233; WO99/58962; WO99/32662; WO99/14599; WO98/12539; WO97/36931 and WO98/57154.

Commercially available ECL instruments have demonstrated good performance. They have become widely used for reasons including their sensitivity, dynamic range, precision, and tolerance of complex sample matrices. Several types of commercial instrumentation are available for carrying out ECL-based measurements (Debad, et al., 2004. Clinical and Biological Applications of ECL, in: Electrogenerated Chemiluminescence. Marcel Dekker, pp. 43-78.). Instruments have been disclosed that are configured to carry out binding assays on beads, and that include flow cells for collecting the beads on an electrode for inducing ECL (U.S. Pat. Nos. 5,935,779 and 5,993,740), ECL instrumentation has also been disclosed that uses reagents immobilized on the electrode used to induce ECL (see, e.g., U.S. Pat. Nos. 6,140,045; 6,066,448; 6,090,545; 6,207,369 and Published PCI Application No. WO98/12539). Multi-well plates having integrated electrodes suitable for such ECL measurements have also been disclosed (see, e.g., U.S. Pat. Nos. 6,977,722 and 7,842,246, hereby incorporated by reference). Cartridges having electrodes for ECL measurements have also been disclosed (e.g., US 2012/0190589 and US 2012/0178091).

Currently, reagents containing the ECL coreactant tripropylamine (IPA) are available to enhance light generation from ECL labels. Applicants have discovered that such components have significant drawbacks.

3. SUMMARY OF THE DISCLOSURE

The present disclosure is directed to compositions, reagents, kits, systems, system components, and methods for performing assays. In embodiments, the disclosure relates to an assay composition for inducing luminescence, the composition comprising an alkyl diethanolamine. In embodiments, the alkyl diethanolamine has the formula $(HOCH_2CH_2)_2N-CHR^1-CHR^2-CHR^3-R^4$, wherein $R^1$, $R^2$, $R^3$ and $R^4$ are each independently $-H$, $-CH_3$, $CH_2CH_3$, or $-CH(CH_3)_2$. In embodiments, $R^1$, $R^2$ and $R^3$ are $-H$ and $R^4$ is $-H$ or $-CH_3$. In embodiments, the disclosure relates to an assay composition for inducing luminescence, the composition comprising N-butyldiethanolamine (BDEA) or 2-dibutylaminoethanol (DBAE). In embodiments, the compositions comprise BDEA.

In embodiments, the present disclosure provides a composition comprising N-butyldiethanolamine (BDEA) or 2-dibutylaminoethanol (DBAE), or both; a pH buffering component; and an ionic component. In embodiments, the present disclosure provides a composition comprising N-butyldiethanolamine (BDEA) or 2-dibutylaminoethanol (DBAE), or both; a pH buffering component; an ionic component; and a surfactant. In embodiments, the present disclosure provides a composition comprising N-butyldiethanolamine (BDEA) or 2-dibutylaminoethanol (DBAE), or both; a pH buffering component; an ionic component; and a liquid diluent. In embodiments, the present disclosure provides a composition comprising N-butyldiethanolamine (BDEA) or 2-dibutylaminoethanol (DBAE), or both; a pH buffering component; an ionic component; a surfactant; and a liquid diluent.

In embodiments, the present disclosure provides a composition consisting essentially of N-butyldiethanolamine (BDEA) or 2-dibutylaminoethanol (DBAE), or both; a pH buffering component; and an ionic component. In embodiments, the present disclosure provides a composition consisting essentially of N-butyldiethanolamine (BDEA) or 2-dibutylaminoethanol (DBAE), or both; a pH buffering component; an ionic component; and a surfactant. In embodiments, the present disclosure provides a composition consisting essentially of N-butyldiethanolamine (BDEA) or 2-dibutylaminoethanol (DBAE), or both; a pH buffering component; an ionic component; and a liquid diluent. In embodiments, the present disclosure provides a composition consisting essentially of N-butyldiethanolamine (BDEA) or 2-dibutylaminoethanol (DBAE), or both; a pH buffering component; an ionic component; a surfactant; and a liquid diluent.

In embodiments, the present disclosure provides a composition consisting of N-butyldiethanolamine (BDEA) or 2-dibutylaminoethanol (DBAE), or both; a pH buffering component; and an ionic component. In embodiments, the present disclosure provides a composition consisting of N-butyldiethanolamine (BDEA) or 2-dibutylaminoethanol (DBAE), or both; a pH buffering component; an ionic component; and a surfactant. In embodiments, the present disclosure provides a composition consisting of N-butyldiethanolamine (BDEA) or 2-dibutylaminoethanol (DBAE), or both; a pH buffering component; an ionic component; and a liquid diluent. In embodiments, the present disclosure provides a composition consisting of N-butyldiethanolamine (BDEA) or 2-dibutylaminoethanol (DBAE), or both; a pH buffering component; an ionic component; a surfactant; and a liquid diluent.

In some embodiments, the compositions of the present disclosure further comprise an ECL label; a binding reagent for a binding assay; a preservative; a biocide; an antifoaming agent; a perchlorate compound; a coloring agent; a tracer chemical; a solid support; or combinations thereof.

In some embodiments, an ECL generated by an ECL label in the presence of the compositions described herein changes, on average, by less than 1% per ° C. over the temperature range of 18° C. to 30° C. In some embodiments, the slope of a change in ECL with pH for an ECL generated by an ECL label in the presence of the composition is less than 10% per pH unit. In some embodiments, a change in the concentration of the ECL coreactant from 0.8 to 1.2 times the nominal value provides less than a 10% change in an ECL generated by an ECL label in the presence of the compositions described herein. In some embodiments, the ECL is generated from an electrochemiluminescent ruthenium organometallic complex in proximity to a carbon-based electrode.

In additional embodiments, the present disclosure provides a kit comprising in one or more containers the following materials: N-butyldiethanolamine (BDEA) or 2-dibutylaminoethanol (DBAE), or both; a pH buffering component; and an ionic component.

In some embodiments, the kits of the present disclosure comprise the compositions described herein and an assay instrument, an assay consumable, an additional assay reagent, an assay sample, or a combination thereof. In some embodiments, the assay instrument is configured to conduct ECL assays.

In further embodiments, the present disclosure provides a method for producing a composition comprising combining: N-butyldiethanolamine (BDEA) or 2-dibutylaminoethanol (DBAE), or both; a pH buffering component; and an ionic component.

In embodiments, the present disclosure provides a method for generating ECL comprising contacting an electrode with a composition described herein and an ECL label; applying a voltage to the electrode; and generating ECL.

In embodiments, the present disclosure provides a method for measuring the quantity of an ECL label comprising contacting an electrode with a composition described herein and the ECL label; applying a voltage to the electrode; generating ECL; measuring the ECL; and determining, from the measured ECL, the quantity of the label.

In embodiments, the present disclosure provides a method for measuring the quantity of a binding complex comprising a binding reagent linked to an ECL label, the method comprising contacting an immobilized binding reagent on an electrode with a labeled binding reagent comprising an ECL label; forming a binding complex on the electrode comprising the immobilized binding reagent and the labeled binding reagent; contacting the binding complex on the electrode with a composition as described herein; applying a voltage to the electrode in the presence of the composition; generating ECL; and measuring the ECL to determine the quantity of the binding complex on the electrode.

In embodiments, the present disclosure provides a method for measuring the quantity of a binding complex comprising a binding reagent linked to an ECL label, the method comprising contacting an immobilized binding reagent on a particle with a labeled binding reagent comprising an ECL label; forming a binding complex on the particle comprising the immobilized binding reagent and the labeled binding reagent; contacting the binding complex on the particle with a composition as described herein; collecting the particle on an electrode; applying a voltage to the electrode in the presence of the composition; generating ECL; and measuring the ECL to determine the quantity of the binding complex on the electrode.

In embodiments, the present disclosure provides a method for measuring the quantity of an analyte, the method comprising: contacting an immobilized binding reagent on an electrode with a labeled binding reagent comprising an ECL label and the analyte (or a sample comprising the analyte); forming a binding complex on the electrode comprising the immobilized binding reagent and the labeled binding reagent; contacting the binding complex on the electrode with a composition as described herein; applying a voltage to the electrode in the presence of the composition; generating ECL; and measuring the ECL to determine the quantity of the analyte.

In embodiments, the present disclosure provides a method for measuring the quantity of an analyte, the method comprising: contacting an immobilized binding reagent on a particle with a labeled binding reagent comprising an ECL label and an analyte (or a sample comprising the analyte); forming a binding complex on the particle comprising the immobilized binding reagent and the labeled binding reagent; contacting the binding complex on the particle with a composition described herein; collecting the particle on an electrode; applying a voltage to the electrode in the presence of the composition; generating ECL; and measuring the ECL to determine the quantity of the analyte.

4. DESCRIPTION OF THE FIGURES

FIG. 1A shows the specific ECL signals for ECL labeled reagent on an electrode surface, and FIG. 1B shows background ECL signals in the absence of the labeled reagent, when ECL is generated in the presence of ECL read buffers containing BDEA, DBEA or TPA coreactants, with or without the presence of TRITON X-100. FIG. 1C also shows the effect of changing the pH buffering component in the read buffer.

FIGS. 2A and 2B show the specific signals and background signals generated by a multiplexed panel of ECL sandwich immunoassays. FIG. 2A compares the signals generated in the presence of a BDEA-containing coreactant composition to those generated by a conventional TPA-containing coreactant composition; and FIG. 2B compares the signals generated in the presence of a BDEA-containing coreactant composition containing a high level of salt to those generated by a conventional TPA-containing coreactant composition.

FIGS. 3A-3F show the effects of sources of compositional and environmental variation on specific ECL signals and ECL background signals generated in the presence of BDEA and TPA containing ECL read buffers including the effect of read buffer pH (FIG. 3A), the effect of read buffer temperature during ECL generation (FIG. 3B), the effect of coreactant concentration and surfactant presence or absence (FIG. 3C), the effect of diluting or concentrating all the ingredients within the read buffers (FIG. 3D), the effect of read buffer temperature and pH (FIG. 3E), and % background change at different read buffer temperature and pH (FIG. 3F).

FIG. 5B shows the liquid/lair interfacial tensions (in dynes/cm) for read buffers prepared with these surfactants.

FIG. 7 shows ECL signals from an ECL sandwich immunoassay for extracellular vesicles expressing the CD9 surface protein and compares the signals measured using different BDEA-containing read buffers that include different surfactants and, for each read buffer, compares the signal measured immediately after addition of read buffer (T=0) to the signal measured if the assay product was incubated in the read buffer for 15 minutes before measurement of the signal (T=15).

Figure 8:
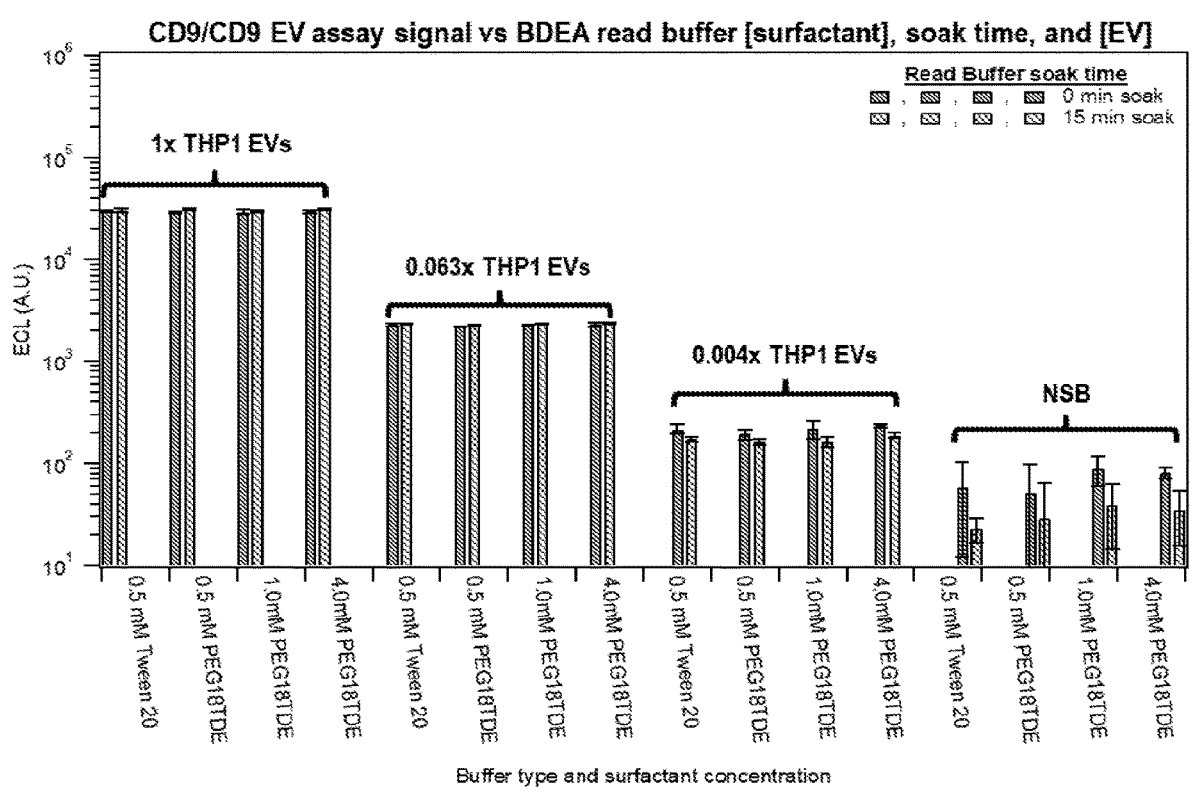

FIG. 8 shows ECL signals from an ECL sandwich immunoassay for extracellular vesicles (EV) expressing the CD9 surface protein and compares the signals measured using different BDEA-containing read buffers that include either TWEEN 20 or PEG(18) tridecyl ether (PEG18TDE) at various concentrations. Four different concentrations of EVs were tested.

FIGS. 9A-9D show the average % ECL loss using BDEA or TPA read buffer during antibody screens for the analytes sRange (FIG. 9A), IL-9 (FIG. 9B), Kim-1 (FIG. 9C), and MIG (FIG. 9D).

Figure 10A:
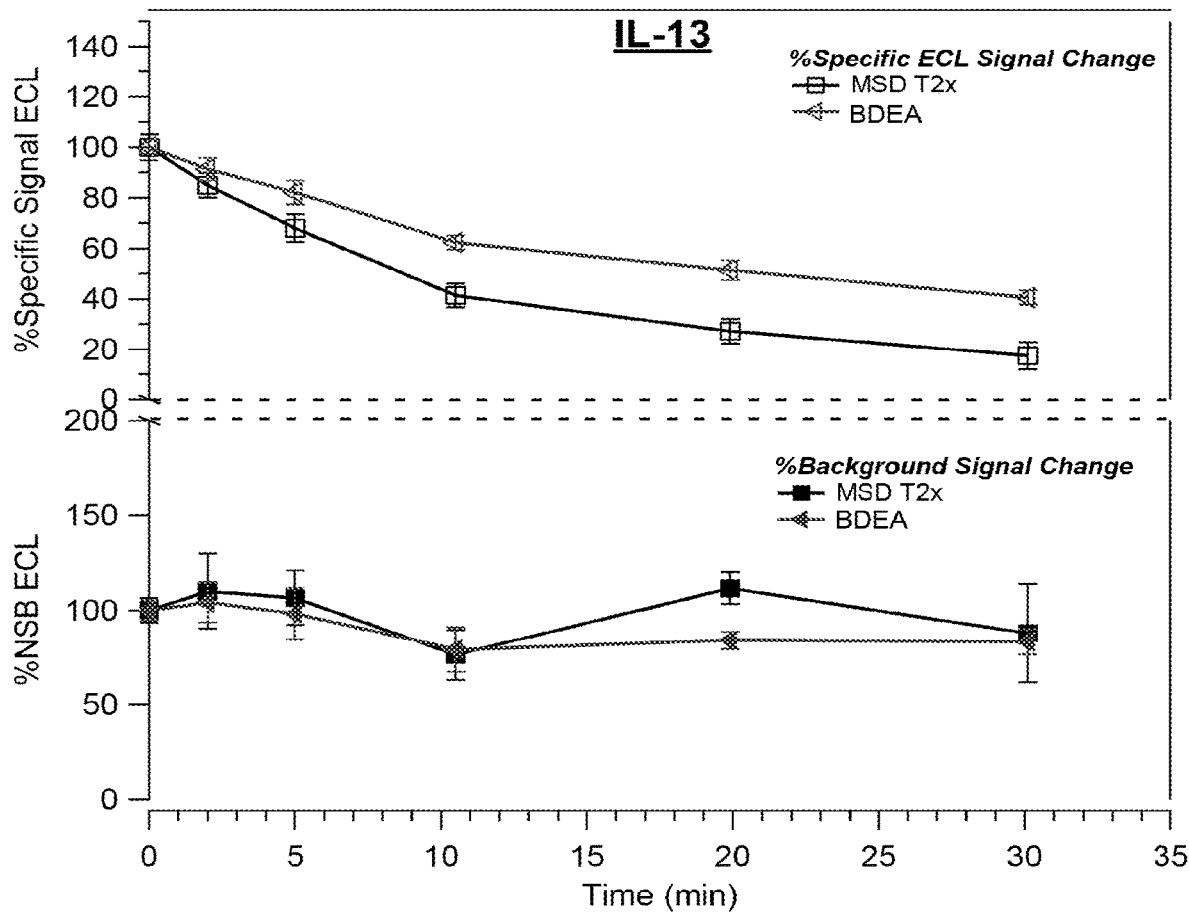
Figure 10B:
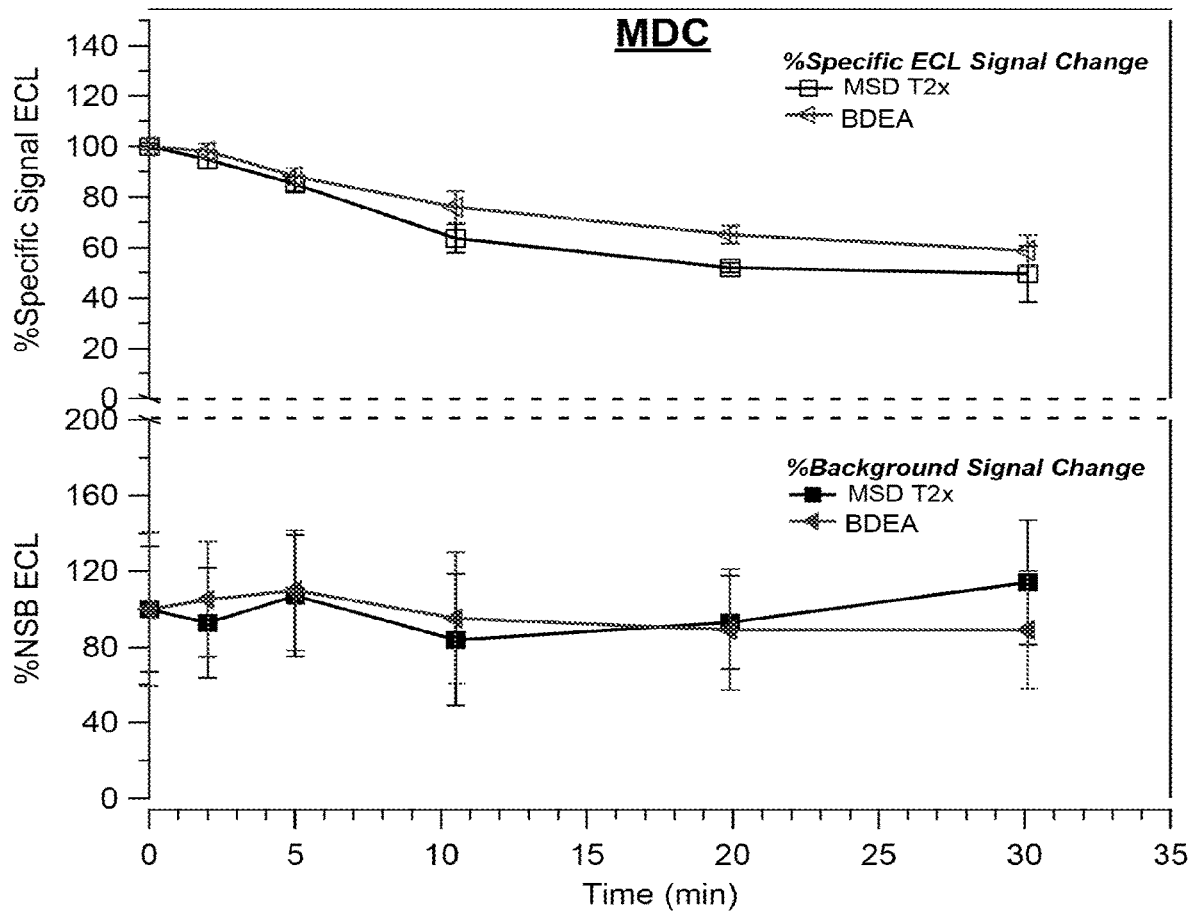
Figure 10C:
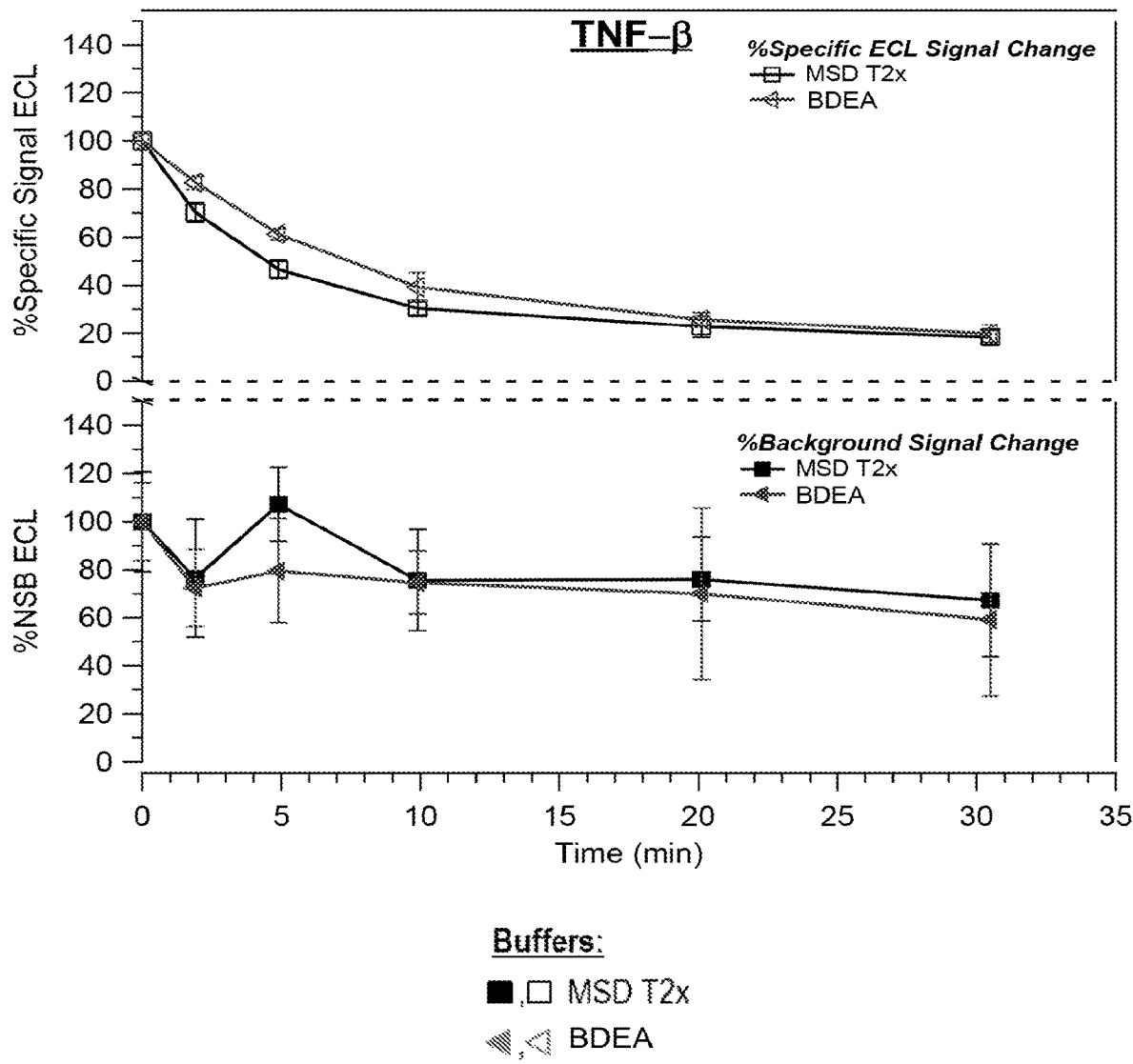

FIGS. 10A-10C show the % specific and % non-specific ECL, signal in multiplex assays using BDEA or TPA read buffer with the analytes IL-13 (FIG. 10A), MDC (FIG. 10B), and TNF-β (FIG. 10C).

Figure 11A:
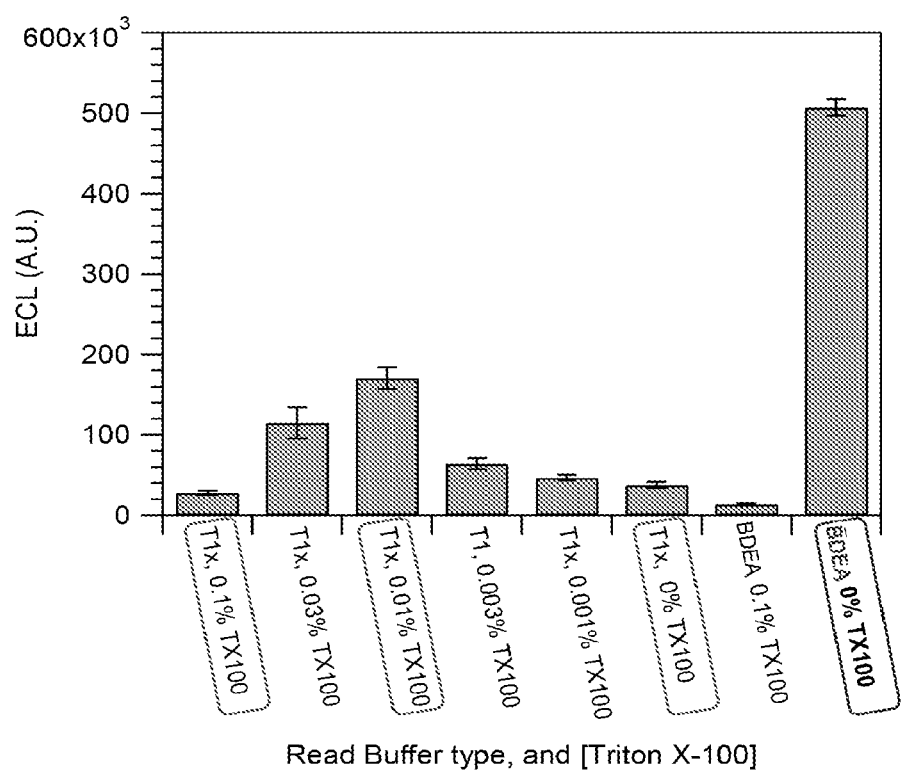
Figure 11B:
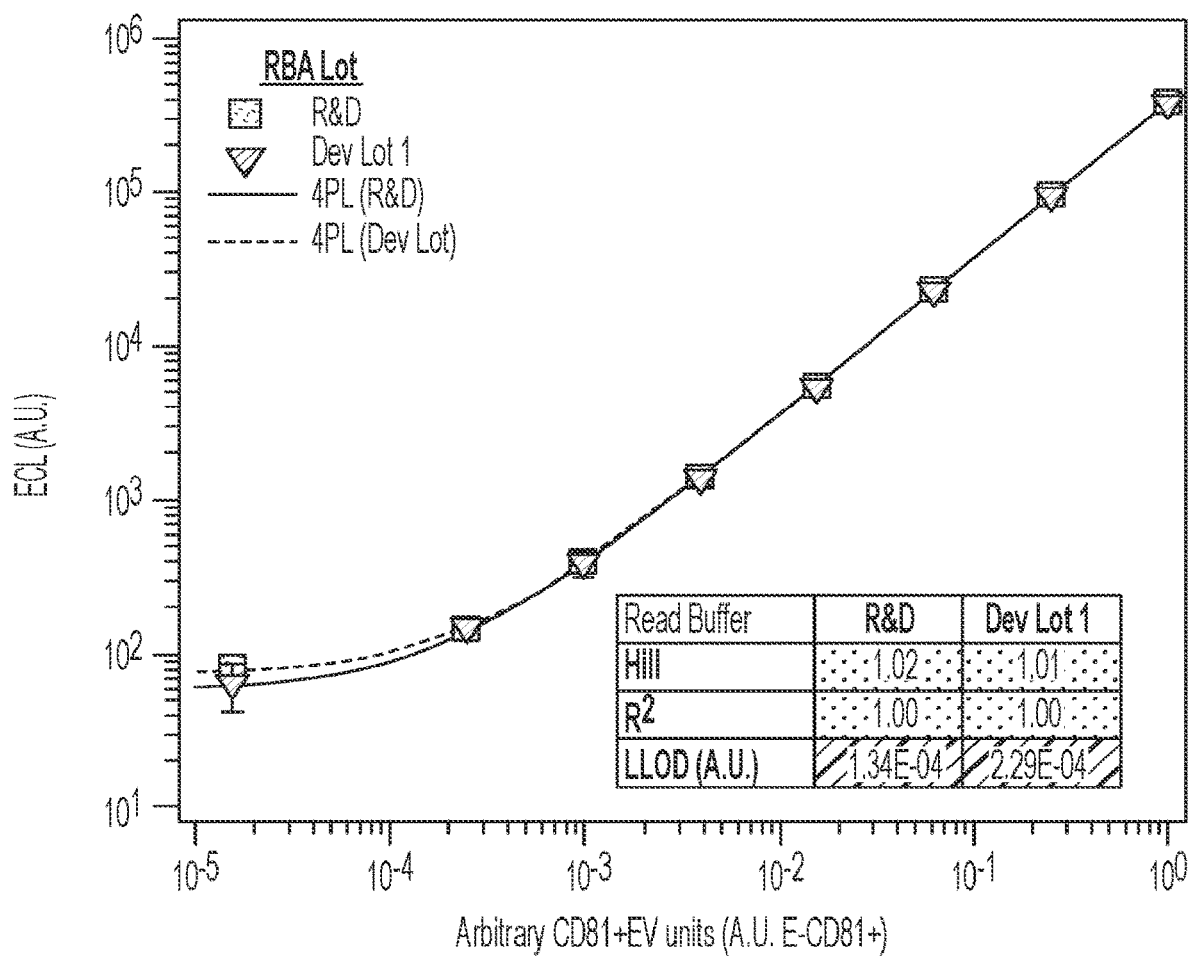

FIG. 11A shows the ECL signal change in an EV assay using BDEA or TPA read buffer with varying concentration of TRITON X-100. FIG. 11B shows a titration curve for known concentrations of EV tested with two different lots of non-TRITON BDEA read buffer.

5, DETAILED DESCRIPTION OF THE DISCLOSURE

The disclosure, as well as additional objects, features and advantages thereof, will be understood more fully from the following detailed description of certain embodiments.

As described herein, the ECL coreactant tripropylamine (TPA) has certain disadvantages. For example, TPA has low solubility in water, which leads to manufacturing difficulties, and it is volatile with an unpleasant odor, Thus, the inventors set out to determine whether it was possible to find a formulation in which TPA was replaced with another ECL coreactant.

In embodiments, the invention provides ECL coreactant reagents and formulations that include an alkyl diethanolamine of the following formula $(HOCH_2CH_2)_2N—CHR^1—CHR^2—CHR^3—R^4)$:

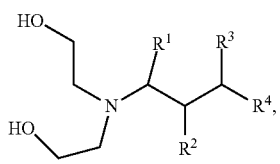

wherein $R^1$, $R^2$, $R^3$ and $R^4$ are each independently —H, —$CH_3$, —$CH_2CH_3$, or —$CH(CH_3)_2$. In embodiments, $R^1$, $R^2$, $R^3$ are each —H and $R^4$=—$CH_3$ (BDEA). In embodiments, $R^1$, $R^2$, $R^3$ and are each H.

The invention includes reagents and formulations which include BDEA or DBAE, preferably BDEA, as an ECL coreactant, providing an alternative to the use of TPA as an ECL coreactant. These coreactants are highly water soluble, non-volatile and have little to no odor, thus addressing the major limitations of TPA. The inventors discovered preferred compositions containing the new coreactants that are able to provide comparable ECL signal generation to TPA-containing compositions, while also minimizing assay background signals. The compositions of the invention also provide additional unexpected advantages over conventional TPA-containing compositions that include: (i) the ECL signals are less sensitive to lot-to-lot variations in the coreactant component, such as variability in the levels of trace contaminants; (ii) the ECL signals are also less sensitive to changes in pH, temperature and salt concentration; (iii) the ECL signals are insensitive to the presence or absence of surfactants and, unlike TPA-containing compositions, do not require the presence of harsh aromatic surfactants such as TRITON X-100 (which can disrupt certain analytes, especially analytes comprising lipid membranes) for optimal signal generation; and (iv) reduced ECL signal loss, which is indicative of a lower off-rate between the analyte and binding reagent. These unexpected benefits, in turn, provide greater robustness than TPA-containing compositions to sources of lot-to-lot variability in manufacturing and measurement-to-measurement variability when conducting assays. Reducing these sources of assay variability is highly desired in the field. See, e.g., Lee at al., 2006. In addition, the unexpected low sensitivity to surfactant presence allows for the tailoring of surfactant composition and concentration to achieve specific desirable attributes such as control over solution surface tension and meniscal shapes, as well as control over the ability to preserve or disrupt the association of components in an assay mixture.

The invention includes (i) compositions as described herein, (ii) assay reagents that include one or more of the components of these compositions, (iii) kits that contain one of these compositions or reagents and, optionally, other assay components and (iv) methods that employ these compositions, reagents and/or kits for carrying out an ECL process or measurement.

In the discussion and claims herein, the term "about" modifying the quantity of an ingredient or reactant of the invention employed refers to variation in the numerical quantity that can occur, for example, through typical measuring and liquid handling procedures used for making concentrates or using solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, preferably within 5% of the reported numerical value.

As used herein, unless otherwise noted, compositions containing components joined by the term "or" encompass compositions with combinations of the components. For example, a composition comprising "x", "y", or "z"

includes, but is not limited to, compositions comprising "x", "y" and "z"; "x" and "y"; "x" and "z"; and "y" m and "z".

As used herein, the term "substantially," or "substantial," is equally applicable when used in a negative connotation to refer to the complete or near complete lack of an action, characteristic, property, state, structure, item, or result. For example, a surface that is "substantially" flat would be either completely flat, or so nearly flat that the effect would be the same as if it were completely flat.

As used herein, terms such as "a," "an" and "the" are not intended to refer to only a singular entity, but include the general class of which a specific example may be used for illustration.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes whole numbers of 5, 6, 7, 8, 9, and 10, and fractional numbers 5.1, 5.2, 5,3, 5.4, 5.5, 5,6, 5.7, 5.8, 5.9, etc.

A substance that can be induced to emit ECL may be referred to as being ECL-active or having ECL-activity. It may also be referred to as an ECL-active species, an ECL moiety, ECL label. ECL label compound or ECL label substance, etc. It is within the scope of the disclosure for these ECL-active species—when utilized in certain composition, reagent, kit, method, or system embodiments in accordance with the disclosure—to be linked to other molecules and, in particular, to components of biochemical or biological assays, e.g., an analyte or an analog thereof, a binding partner of the analyte or analog thereof, a further binding partner of such aforementioned binding partner, or a reactive component capable of binding with the analyte, an analog thereof or a binding partner as mentioned herein. The ECL-active species described herein can also be linked to a combination of one or more binding partners and/or one or more reactive components. In certain enzymatic assays, an ECL-active species may be linked to an enzyme substrate. In the context of the excitation of measurement of ECL, art ECL-active species may be described as being "bound" or "free". In this context, "bound" refers to ECL-active species held in proximity to an electrode that is used to induce ECL, for example, species that are directly immobilized on the electrode, that are held through binding interactions to other species that are immobilized on the electrode, and that are present on the surface of beads that have been collected on the surface of the electrode. In contrast, in this context "free" refers to labels that are free to diffuse in a bulk liquid media in contact with the electrode, such as a solution, suspension or emulsion containing ECL-active species.

It is similarly within the scope of the disclosure for the aforementioned "composition," hereinafter sometimes an "ECL composition," or a "system" to contain unstable, metastable and other intermediate species formed in the course of the ECL reaction, such as an ECL moiety in an excited state as aforesaid. Additionally, although the emission of visible light is an advantageous feature of certain embodiments of the disclosure, it is within the scope of the disclosure for the composition (hereinafter sometimes "ECL composition") or system to emit other types of electromagnetic radiation, such as infrared or ultraviolet light, X-rays, microwaves, etc. Use of the terms "electrochemiluminescence." "electrochemiluminescent," "luminescence," "luminescent" and "luminesce" in connection with the present disclosure does not require that the emission be light, but admits of the emissions being such other forms of electromagnetic radiation.

The compositions in the disclosure may comprise acidic or basic components that may be present in protonated or deprotonated forms, e.g., depending on the pH of an aqueous composition. For example, a reference to an amine or other base (such as BDEA, DBAE, or Tris) may refer to the unprotonated (amine) form or to the protonated (ammonium) form. Similarly, a reference to phosphate could refer to phosphoric acid or any of the deprotonated states of phosphate.

The present disclosure relates to ECL read buffers, assay compositions and kits containing the same, and methods of using the same. A kit refers to a set of components that are provided to be used together, for example, to create a composition, to manufacture a device, or to carry out a method. A kit can comprise one or more components. The components of a kit may be provided in one package or in multiple packages, each of which can contain one or more of the components.

In embodiments, the compositions of the present disclosure are used in assay systems in replacement of, or in combination with, or substitution for TPA containing compositions.

One aspect of the disclosure relates to improved ECL assay compositions that comprise an ECL coreactant, wherein the ECL coreactant is BDEA or DBAE, preferably BDEA. These ECL assay compositions provide a suitable environment for inducing ECL labels to emit ECL and for sensitively measuring ECL labels via the measurement of ECL. The ECL assay composition of the disclosure may optionally comprise additional components including pH buffers, detergents, preservatives, surfactants, anti-foaming agents. ECL active species, salts, chelators, acids, bases, metal ions and/or metal chelating agents, and/or additional coreactants.

The ECL assay compositions of the disclosure may also include components of a biological assay, which in some cases may be labeled with an ECL label, including antibodies, fragments of antibodies, proteins, enzymes, enzyme substrates, enzyme inhibitors, cofactors, antigens, haptens, lipoproteins, liposaccharides, cells, sub-cellular components, cell receptors, membrane fragments, exosomes, extracellular vesicles, viruses, nucleic acids, nucleic acid analogs (including analogs having unnatural linkages. such as protein nucleic acids. or unnatural nucleotide bases), antigens, lipids, glycoproteins, carbohydrates, peptides, amino acids, receptors, hormones, binding reagents, protein-binding ligands, ligands, pharmacological agents, membrane vesicles, liposomes, organelles, bacteria, fungi or combinations thereof. These biological assay components may be in a non-immobilized form or they may be immobilized on a solid phase surface, including surfaces of solid phases used in solid phase binding assays including, but not limited to, a surface of a slide, a chip, a well, an assay cell, a tube or other container, a bead, or a microparticle. The ECL assay compositions may also include the analytes to be measured in a biological assay and/or a sample or components of a sample in which an analyte is to be measured by a biological assay.

The disclosure also relates to ECL read buffers, which are compositions that comprise ECL coreactant, and optionally one or more additional components of an ECL assay composition as described herein, and which are useful for use in assays that measure analytes in samples. The ECL read buffers are then used by themselves or in combination with other assay components to form ECL assay compositions as described herein. In one embodiment, an ECL read buffer comprises an (i) ECL coreactant, (ii) a pH buffering component holding the pH of the read buffer within a defined range, (iii) an additional ionic component and, optionally, (iv) a surfactant.

The ECL assay compositions and ECL read buffers of the disclosure can be aqueous or substantially aqueous >75% or preferably >85% water by weight) in nature, although it may be desirable in some applications to add organic co-solvents such as DMSO, DMF, formamide, ethylene glycol, propylene glycol, methanol, ethanol, glycerol or other alcohols. In embodiments of the disclosure, an ECL read buffer (or one or more components thereof) is provided in dry form and the user converts it to a liquid reagent by addition of the appropriate solvent or matrix (preferably water or an aqueous medium), and preferably by adding a defined volume of the appropriate solvent or matrix, so as to produce a solution with pre-specified concentrations of the solution components.

5.1 ECL Coreactants

Applicants have discovered ECL read buffers and ECL assay compositions comprising non-TPA coreactants that in some applications provide performance that is comparable or better than TPA.

In embodiments, the non-TPA coreactant is an alkyl diethanolamine of the following formula. $(HOCH_2CH_2)_2N-CHR^1-CHR^2-CHR^3-R^4$:

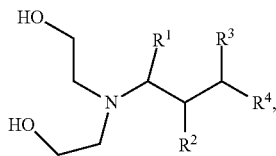

wherein $R^1$, $R^2$, $R^3$ and $R^4$ are each independently —H, —$CH_3$, —$CH_2CH_3$, or —$CH(CH_3)_2$. In embodiments, $R^1$, $R^2$, $R^3$ are each —H and $R^4$=—$CH_3$ (BDEA). In embodiments, $R^1$, $R^2$, $R^3$ and $R^4$ are each H.

The non-TPA coreactants include BDEA or DBAE (structures shown below) Preferably, the non-TPA coreactant is BDEA.

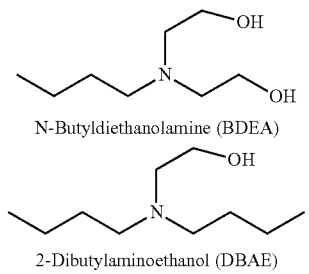

N-Butyldiethanolamine (BDEA)

2-Dibutylaminoethanol (DBAE)

Relative to TPA, BDEA and DBAE have low volatility (vapor pressure less than 2 mm Hg at room temperature), high boiling points (boiling points greater than 200° C. at atmospheric pressure), good water solubility, low odor, and low flammability. Applicants have discovered that BDEA's surprisingly advantageous effects are relatively not influenced by its concentration as an ECL coreactant. This coreactant can be combined with other components to form a composition, as discussed below. This includes adding other ECL coreactants such as TPA, or N,N-dibutylethanolamine, or both.

The concentration of BDEA or DBAE coreactant in the ECL assay compositions and/or read buffers of the invention can be between about 10 mM and about 800 mM, between about 75 mM and about 400 mM, between about 75 mM and about 300 mM, between about 100 mM and about 300 mM, between about 100 mM and about 225 mM, between about 100 mM and about 150 mM, between about 100 mM and about 175 mM, about 150 mM, or about 125 mM. The concentration may be selected such that in an ECL assay employing the composition and/or read buffer, the specific ECL signal is relatively insensitive to small changes in coreactant concentration, for example, a change in concentration from about 0.5 times to about 5 times, or from about 0.6 times to about 2.5 times, or from about 0.7 times to about 1.2 time, or from about 0.8 times to about 1.5 times, or from about 0.8 times to about 1.4 times, or from about 0.8 times to about 1.2 times the nominal value leads to a specific ECL signal change of less than or about 5%, less than or about 10%, or less than or about 20%.

In one embodiment, the ECL assay compositions and/or read buffers are such that the ECL generation step in ECL assays employing them are relatively insensitive to temperature changes, for example, a change in temperature from 18° C. to 30° C. for the step of generating ECL from an ECL label in the presence of the ECL assay composition leads to an change in specific ECL of less than 10%, less than 20%, or less than 30%, or the slope of change in ECL with temperature over this range was less than 2% per ° C., or less than 10% per ° C.

In embodiments of the compositions of the present disclosure, the ECL coreactant is BDEA. In embodiments, the ECL coreactant is DBAE. In embodiments, an ECL generated by an ECL label in the presence of the composition changes, on average, by less than 1% per ° C. over the temperature range of 18° C. to 30° C. In embodiments, the ECL is generated from an electrochemiluminescent ruthenium organometallic complex in proximity to a carbon-based electrode.

In embodiments, the concentration of the ECL coreactant in the composition is between about 10 mM and about 800 mM. In embodiments, the concentration of the ECL coreactant is between about 75 and about 300 mM. In embodiments, the concentration of the ECL coreactant is between about 100 mM and about 150 mM. In embodiments, a change in the concentration of the ECL coreactant from 0.8 to 1.2 times the nominal value provides less than a 10% change in an ECL generated by an ECL label in the presence of the composition. In embodiments, the ECL is generated form an electrochemiluminescent ruthenium organometallic complex in proximity to a carbon-based electrode.

5.2 pH Buffers

The co-reactant containing ECL assay compositions and read buffers of the invention are, preferably, designed to maintain a pH within a desired range. To achieve control over the pH, these compositions and buffers may include a pH buffering component. Materials that can act as pH buffering components to maintain solutions within specific pH ranges are well known in the art. Examples of suitable pH buffering components include tris(hydroxymethyl)aminomethane (also referred to herein as "Tris"), phosphate, HEPES, glycylglycine (also referred to as GlyGly), borate, acetate, and citrate. Preferred pH buffering components are Tris and phosphate. Tris is especially preferred because mixtures of Tris and BDEA (or DBAE) provide efficient generation of ECL in the presence of ECL labels, but very low ECL background signals in the absence of ECL labels. In one embodiment of the invention, a buffering component used in an ECL assay composition and/or read buffer is selected such that, relative to an analogous composition wherein the buffering component is replaced with the same concentration of phosphate, the specific signal in an ECL assay using that composition is greater than, or at least about 20% greater than, or at least about 50% greater than the signal with the phosphate composition and the read buffer background signal in the absence of ECL labels is less than, or at least about 20% less than, or at least about 50% less than, or at least about 80% less than the read buffer background in with the phosphate composition.

The concentration of a pH buffering component in the ECL assay compositions and/or read buffers of the invention can be between about 10 mM and about 800 mM, between about 50 mM and about 400 mM, between about 100 mM and about 300 mM, between about 150 mM and 250 mM, or about 200 mM.

The ECL assay compositions or read buffers may be designed or adjusted to have a pH within a defined range. The composition can have a pH ranging from about 6 to about 10, about 6 to about 9, about 7 to about 8, about 7.6 to about 7.9 or about 7.8. In one embodiment, the formulation and pH of the ECL assay compositions and/or read buffers are chosen, so that in an ECL assay using the composition the ECL signal is insensitive to changes in pH, for example, the change in specific ECL signal with a 0.1 increase or decrease in pH is less than 5% or less than 10%, or the rate of change in ECL signal over this pH range is less than 10% per pH unit or less than 25% per pH unit.

In embodiments of the compositions of the present disclosure, the pH buffering component is phosphate, HEPES, glycylglycine, borate, acetate or citrate.

In embodiments of the compositions of the present disclosure, the pH buffering component is Tris. In embodiments, the pH buffering component is Tris, and the composition comprises a surfactant. In embodiments, the surfactant is a non-ionic surfactant. In embodiments, the surfactant is a non-ionic surfactant that comprises a phenol ether. In embodiments, the surfactant is TRITON X-100. In embodiments, the surfactant is a non-ionic surfactant that does not comprise an aromatic group. In embodiments, the surfactant is a non-ionic surfactant that does not comprise a phenol ether. In embodiments, the composition does not disrupt lipid bilayer membranes. In embodiments, the surfactant is a non-ionic surfactant, for example, KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(n) tridecyl ether, BRIJ L4, BRIJ 58 or TWEEN 20. In embodiments, the surfactant comprises an alkyl ether-PEG. In embodiments, the surfactant is a linear alkyl ether-PEG. In embodiments, the surfactant is PEG(10) tridecyl ether, PEW 2) tridecyl ether, or PEG(18) tridecyl ether. In embodiments, the surfactant is TWEEN-20. In embodiments, the surfactant is PEG(18) tridecyl ether. "PEG" refers to a polyethyleneglycol moiety in the detergent and PEG(n) refers to a polyethyleneglycol moiety comprising n monomer subunits.

In embodiments of the compositions of the present disclosure, the pH of the composition is between about 6 and about 9. In embodiments, the pH is between about 7 and about 8. In embodiments, the pH is between about 7.6 and about 7.9. In embodiments, the pH is about 7.8. In embodiments, a slope of a change in ECL with pH for an ECL generated by an ECL label in the presence of the composition is less than 10% per pH unit, in embodiments, the ECL is generated from an electrochemiluminescent ruthenium organometallic complex in proximity to a carbon-based electrode.

In embodiments of the compositions, the concentration of the pH buffering component is between about 10 mM and about 800 mM. In embodiments, the concentration of the pH buffering component is between about 100 mM and about 300 mM. In embodiments, the concentration of the pH buffering component is between about 150 mM and about 250 mM.

In embodiments of the composition, the pH buffering component is not phosphate and the composition provides at least a 20% increase in an ECL generated by an ECL label and/or at least a 20% decrease in background ECL generated in the absence of an ECL label, compared with the same composition that contains phosphate as the pH buffering component. In embodiments, the ECL from the ECL label is generated from an electrochemiluminescent ruthenium organometallic complex in proximity to a carbon-based electrode and/or ECL in the absence of an ECL label is generated at a carbon-based electrode.

5.3 Ions and Salts

The compositions and/or read buffers of the disclosure may include various concentrations of one or more ions or salts (including or in addition to the pH buffering components as described herein). A key unexpected finding in the development of the non-TPA containing compositions and read buffers of the invention is the beneficial effect of high ion concentrations, relative to the ion concentrations typically used in analogous TPA-containing compositions, and in particular, the beneficial effect of high ion concentrations on reducing the non-specific binding of labeled species. Salts that may be added to increase the ion concentrations are well known in the art and include salts comprising the cations $Li^+$, $Na^+$, $K^+$, $Rb^+$, $Mg^{+2}$, $Ca^{+2}$, $NH_4^+$ (preferably $Li^+$, $Na^+$ and $K^+$), and/or salts comprising the anions $F^-$, $Cl^-$, $Br^-$, $I^-$, phosphate, sulfate, borate (preferably $Cl^-$). Salts that may be used include potassium chloride (KCl), sodium chloride (NaCl), lithium chloride (LiCl) and combinations thereof. In one embodiment of the invention, the identity and concentration of the ionic species in a non-TPA containing ECL assay composition and/or read buffer are selected so that, compared to an analogous ECL assay composition in which the non-TPA coreactant is replaced with TPA, the specific signals in an ECL assay are between about 50% to about 200%, or between about 75 to about 125% of the signals with the TPA composition and the non-specific background signals are between about 50% to about 200%, or between about 75 to about 125% of the non-specific background signals with the TPA composition.

The coreactant containing ECL assay compositions and/or read buffers of the invention may include salts, such as those described herein, such that the total concentration of anionic species is about or greater than 250 mM, about or greater than 500 mM, about or greater than 750 mM, about or greater than 1000 mM, about 250 mM to about 1400 mM, about 500 mM to about 1200 mM, or about 1050 mM. Such compositions and/or read buffers include embodiments wherein the total concentration of chloride ion ($Cl^-$) is about or greater than 250 mM, about or greater than 500 mM, about or greater than 750 mM, about or greater than 1000 mM, about 250 mM to about 1400 mM, about 500 mM to about 1200 mM, or about 1050 mM.

In embodiments that include a Cl⁻ component, the disclosed composition can include NaCl, KCl, LiCl or mixtures thereof. In this embodiment, the concentration of NaCl can be about 200 mM to about 1400 mM, about 600 mM to about 1200 mM or about 800 mM the concentration of KCl can be about 50 mM, about 200 mM to about 1400 mM, about 500 mM, about 600 mM to about 1200 mM or about 800 mM; and the concentration of LiCl can be about 200 mM to about 1400 mM, about 600 mM to about 1200 mM or about 800 mM. The disclosed composition can include NaCl at a concentration of about 800 mM and the concentration of KCl can be about 50 mM. The disclosed composition can also include LiCL at a concentration of about 800 mM and the concentration of KCl can be about 50 mM.

In one embodiment of the disclosed composition, the composition can have an ionic strength of about 0.3 M to about 1.9 M or about 1.4 M, about 0.5 M to about 1.2 M or about 1.0 M, about 0.8 M to about 1.2 M, about 1.0 M to 1.2 M or about 1.1 M.

In embodiments of the compositions of the present disclosure, the ionic component comprises chloride ion. In embodiments, the ionic component comprises NaCl, KCl, LiCl or combinations of any two or any three of the salts. In embodiments, the ionic component comprises NaCl. In embodiments, the ionic component comprises KCl.

In embodiments, the composition has an ionic strength of greater than about 0.3 M. In embodiments, the composition has an ionic strength of greater than about 0.5 M. In embodiments, the composition has an ionic strength of greater than about 0.8 M. In embodiments, the composition has an ionic strength of greater than about 1.0 M.

In embodiments, the composition comprises chloride ion and the concentration of chloride ion is greater than about 0.25 M. In embodiments, the composition comprises chloride ion and the concentration of chloride ion is greater than about 0.5 M. In embodiments, the composition comprises Chloride ion and the concentration of chloride ion is greater than about 0.75 M. In embodiments, the composition comprises chloride ion and the concentration of chloride ion is greater than about 1.0 M.

In embodiments, non-specific binding (NSB) in an immunoassay is lower with the composition containing the ionic component compared to the same component that contains no ionic component.

5.4 Surfactants

An unexpected aspect of BDEA and DBAE-based ECL compositions and read buffers is the insensitivity of ECL generation to the presence, concentration or structure of surfactants. In contrast, TPA-based compositions require the presence of surfactants for optimal signal generation. In particular, TPA provides optimal ECL generation in the presence of surfactants comprising aromatic moieties, such as the phenolic ether moiety in TRITON X-100.

Accordingly, the coreactant-containing ECL assay compositions and/or read buffers of the invention include compositions (i) that do not include surfactants or (ii) that include surfactants, but only in concentrations that are below the critical micellar concentration (cmc) for the surfactants. The critical micellar concentration (cmc) is known as the concentration of surfactants above which micelles form, and all additional surfactants added to the composition go to the micelles. The coreactant-containing ECL assay compositions and/or read buffers of the invention also include compositions (i) that do not include aromatic surfactants or, more specifically, surfactants containing phenol ether moieties or, more specifically, TRITON X-100 or (ii) that include surfactants as described in (i), but only in concentrations that are below the critical micellar concentration (cmc) for the surfactants.

Alternatively, it may still be advantageous in some applications to include a surfactant, e.g., to provide a lower surface tension or to break up undesired molecular aggregates. Surfactants that may be present include aromatic surfactants such as TRITON X-100 and/or non-aromatic surfactants. Surfactants that may be present include non-ionic surfactants and ionic surfactants. Non-ionic surfactants that may be present include the surfactant classes known by the trade names of NONIDET, BRIJ, TRITON, TWEEN, THESIT, LUBROL, GENAPOL, PLURONIC, TETRONIC, F108, and SPAN. Preferably the surfactant is included a concentration that provides a solution with an air-liquid surface tension less than or about 50 dyne/cm, less than or about 40 dyne/cm or less than or about 35 dyne/cm. Preferably, included surfactants are present at concentrations about or above their cmc, about or above the two times their cmc, or about or above five times their cmc. In embodiments, the compositions and/or read buffers of the present disclosure include a surfactant at a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% by weight per volume of the composition. In embodiments, the compositions and/or read buffers of the present disclosure include a surfactant at a concentration of from about 0.1 mM to about 10 mM, from about 0.2 mM to about 8 mM, from about 0.3 mM to about 5 mM, from about 0.4 mM to about 0.8 mM, from about 0.5 mM, to about 0.6 mM, about 1 mM, or about 0.5 mM. In embodiments, the surfactant included in the ECL coreactant-containing composition and/or read buffer is included at a concentration of about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, or about 10 mM. In embodiments, the concentration of the surfactant is between about 0.2 mM and about 10 mM. In embodiments, the concentration of the surfactant is between about 0.5 mM and about 8 mM. In embodiments, the concentration of the surfactant is between about 1.0 mM and about 5 mM. In embodiments, the concentration of the surfactant is about 0.5 mM. In embodiments, the concentration of the surfactant is about 1.0 mM. In embodiments, the concentration of the surfactant is 5.0 mM. In embodiments, the concentration of the surfactant is about 10 mM. In embodiments, the concentration of the surfactant is greater than the critical micellar concentration (cmc) of the surfactant.

Advantageously, surfactants may be selected for inclusion in the compositions and/or read buffers that provide some desired attributes of surfactants such as low surface tension (and better controlled meniscus angles), but are less denaturing than TRITON X-100 with respect to specific biological assay targets. The invention includes embodiments wherein a mild surfactant is included that does not disrupt analytes that comprise lipid bilayer membranes. Such mild surfactants include but are not limited to (i) oligomers of ethylene glycol and/or propylene glycol, or (ii) alkyl chains linked though an ether group to oligomers of ethylene glycol and/or propylene glycol. Such mild surfactants may also be in the surfactant classes known by the trade names of BRIJ, TWEEN, PLURONIC or KOLLIPHOR. Such mild surfactants may also be specific surfactants such as KOLLIPHOR P-407, PLURONIC P-123, PLURONIC L-121, PLURONIC 31R1, TETRONIC 701, 2,4,7,9-tetramethyl-5-decyne-4,7-diol ethoxylate, $HO(CH_2CH_2)_{18}C_{13}H_{27}$ (also referred to as PEG(18) tridecyl ether). BRIJ L4, BRIJ 58, or TWEEN 20. Such mild surfactants may also be, specific surfactants such as KOLLIPHOR P-407, PLURONIC P-123, or PEG(18) tridecyl ether. Preferably, the surfactant does not include ester linkages.

In embodiments, the composition of the present disclosure comprises a non-ionic surfactant that does not comprise a phenol ether. In embodiments, the composition does not disrupt lipid bilayer membranes. In embodiments, the surfactant is a non-ionic surfactant such as KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the surfactant is TWEEN 20. In embodiments, the surfactant is PEG(18) tridecyl ether. In embodiments, the pH buffering component is phosphate, HEPES, glycylglycine, borate, acetate or citrate.

5.5 ECL Labels and Other Assay Reagents

The compositions of the invention may include a variety of assay reagents and/or components useful for carrying out an assay measurement, which in some cases may be labeled with an ECL label, including whole cells, cell surface antigens, subcellular particles (e.g., organelles or membrane fragments), exosomes, extracellular vesicles, liposomes, membrane vesicles, viruses, prions, dust mites or fragments thereof, viroids, antibodies, antigens, haptens, fatty acids, nucleic acids (and synthetic analogs), proteins (and synthetic analogs), lipoproteins, polysaccharides, inhibitors, cofactors, haptens, cell receptors, receptor ligands, lipopolysaccharides, glycoproteins, peptides, poly peptides, enzymes, enzyme substrates, enzyme products, second messengers, cellular metabolites, hormones, pharmacological agents, synthetic organic molecules, organometallic molecules, tranquilizers, barbiturates, alkaloids, steroids, vitamins, amino acids, sugars, lectins, recombinant or derived proteins, biotin, avidin, and/or streptavidin. The assay reagents can be useful as binding reagents or enzyme substrates in, e.g., binding assays or enzyme assays.

The compositions of the invention may include ECL labels. Useful ECL labels include labels that generate ECL in the presence of TPA as a coreactant. Examples of ECL labels that may be used include luminescent organometallic compounds such as organometallic compounds containing Ru, Os, Ir, Re or a Lanthanide metal (see, e.g., the labels described in U.S. Pat. Nos. 5,714,089, 6, 316, 607, 6,808, 939, 9,416,150). Preferred ECL labels are ruthenium or osmium-containing organometallic species. These ruthenium or osmium-containing organometallic may comprise ruthenium or osmium chelated to polypyridyl ligands (most preferably, bipyridine, phenanthroline, and/or substituted derivatives thereof). Most preferably, the ECL labels comprise ruthenium-tris-bipyridine, the bipyridine ligands being optionally substituted, e.g., with a linking group for attaching the label to an assay reagent and/or with hydrophilic substituents for minimizing non-specific binding. In one embodiment, the ECL label that is used is a ruthenium tri-bipyridine derivative that includes one or two 4,4'-bis (sulfomethyl)-bipyridine ligands (such as labels described in U.S. Pat. No. 6,808,939). The ECL label may be linked to an assay reagent as described herein.

In specific embodiments in which the compositions of the invention are used in binding assays for an analyte, the label may be linked to a binding component of the assay, e.g., an analyte or an analog thereof, a binding partner of the analyte or analog thereof, a further binding partner of such aforementioned binding partner, or a reactive component capable of binding with the analyte, an analog thereof or a binding partner as mentioned herein. The labels described herein can also be linked to a combination of one or more binding partners and/or one or more reactive components. The reactive component may be used to indirectly immobilize or label another assay component. By way of example, in a binding assay employing a binding reagent against an analyte, the binding reagent may be directly immobilized or labeled, or alternatively it may be labeled or immobilized indirectly using a reactive component. Such approaches are well known in the art and include (i) use of secondary binding reagents such as anti-species antibodies to label or immobilize an assay reagent (e.g., an anti-analyte antibody) or (ii) use of labeled or immobilized streptavidin to label or immobilize a biotin-binding reagent conjugate.

5.6 Other Components

The ECL assay compositions and/or read buffers of the disclosure may include various concentrations of one or more other components. In compositions that consist essentially of the recited components, such compositions contain the recited components and those that do not materially affect the basic and novel characteristics of the compositions. Components that do not materially affect the basic and novel characteristics of the compositions are those that do not change the essential ECL characteristics (for example, generation of ECL signal) of the composition. Non-limiting examples of components that could be included in the compositions include cosolvents (such as, e.g., the cosolvents described herein), preservatives and/or biocides (e.g., azide, 5-chloro-2-methyl-4-isothiazolin-3-one and/or 2-methyl-isothiazolin-3-one), anti-foaming agents (including silicone and/or non-silicone based agents, for example, Antifoams 204, A, B, C, Y-30 and/or SE-15 from Millipore Sigma), coloring agents, and tracer chemicals added to provide chemical fingerprints for verifying the source or authenticity of a reagent. In embodiments, a perchlorate compound is included.

5.7 Concentrated and Dried Forms

Another embodiment of the disclosure relates to dry or concentrated reagent compositions that can be diluted with a diluent (e.g., with water or an aqueous solution) to form the ECL assay compositions and/or read buffers as described above. By way of example, such concentrated reagent compositions may have reagent components in dry form, or in liquid form at concentrations that are greater than the concentrations of the reagents in the target ECL assay compositions and; or read buffers the concentrations may be greater than or equal to 2×, greater than or equal to 4×, or greater than or equal to 10× the target concentrations). The invention also includes a method of firming ECL assay compositions and/or read buffers of the invention, the method comprising mixing a dry or concentrated composition with a diluent (such as an aqueous solution, and preferably water). Preferably, a pre-defined amount of the dry or concentrated composition is provided, and a pre-defined volume of diluent is added. In embodiments wherein a concentrated composition is used, the ratio of the volume of the diluent to the volume of the concentrated composition may be about or greater than 1, about or greater than 2, or about or greater than 3.

The formulation of the ECL assay compositions and/or read buffers of the disclosure may be selected so that they are relatively insensitive to concentration or dilution of the ingredients, for example, in the instance of a user inaccurately measuring the volume of diluent used to rehydrate a dry reagent or dilute a concentrated composition. In one embodiment, a composition and/or read buffer is configured such that over a concentration range of 0.8 to 1.2 times the nominal concentration of the ingredients, the specific ECL signal from an ECL assay is relatively unchanged, or changes by less than 10%, or changes by less than 20%, or changes by less than 30%.

In embodiments of the present disclosure, the composition comprises a liquid diluent. In embodiments, the liquid diluent is water and the composition is substantially aqueous.

In embodiments of the present disclosure, the composition does not include a liquid diluent and the composition is provided in dry firm.

5.8 Kits

One aspect of the disclosure relates to kits comprising, in one or more containers, one or more components of the ECL assay compositions and/or read buffers of the disclosure. Preferably, at least one of the containers contains BDEA (or, alternatively, DBAE). Suitable containers that may be used include, but are not limited to, glass and/or plastic containers, and plastic and/or foil pouches. The kit packaging or the component containers can be labeled with information regarding the contents of the kit or container or instructions regarding proper storage and/or use in an assay. These components may be combined, optionally with additional reagents, to form the ECL assay compositions and/or read buffers of the disclosure. The kits may also comprise additional assay related components such as ECL labels, ECL labeled assay reagents, enzymes, binding reagents, electrodes, assay plates, etc. The kit may include components that are in a liquid or dry state.

Another aspect of the disclosure relates to kits that comprise two or more components that, when mixed, form an ECL assay composition or read buffer as described herein. The components may be solids and/or liquids, preferably at least one component is liquid. The invention also includes a method of forming ECL assay compositions and/or read buffers comprising mixing the components in such a kit. In one embodiment, pre-determined amounts of each component are mixed. Such pre-determined amounts of the components may be provided in pre-measured in separate containers. In one embodiment, the method also comprises providing one or more additional components that are not part of the kit and combining them with the components of the kit. In one example, the additional component is a liquid diluent (e.g., water).

Another aspect of the disclosure relates to kits for carrying out an assay that comprises, in one or more containers, an ECL read buffer and one or more additional assay components. Within such kits, the ECL read buffer can be provided as a single component, or as two or more components as described above. Additional assay components used in carrying out the assay that may be part of the kit include, but are not limited to, (i) an assay instrument; (ii) an assay consumable; (iii) an additional assay reagent, and (iv) assay samples, for example for use as calibration standards or assay controls.

Examples of assay consumables that can be included in the kit are assay modules designed to contain samples and/or reagents during one or more steps of the assay, pipette tips and other consumables for transferring liquid samples and reagents, covers and seals for assay modules and other consumables used in an assay, racks for holding other assay consumables, labels (including human readable or machine readable formats such as barcodes, RFIDs, etc.) for identifying samples or other assay consumables and media (including paper and electronic media) for providing information about the assay and/or instructions for carrying out the assay.

Assay modules can include tubes, cuvettes, wells, multi-well plates, cartridges, lateral flow devices, flow cells and the like. The kit can comprise an assay module having one or more assay electrodes, such as an assay plate, or multi-well assay plate according to U.S. Pat. Nos. 7,842,246 and 6,977,722, entitled "Assay Plates, Reader Systems and Methods for Luminescence Test Measurements," or an assay cartridge according to U.S. Pat. No. 9,731,297 entitled "Assay Cartridges and Methods of Using the Same," each hereby incorporated by reference. Preferably, the assay electrodes include carbon electrodes, which may be carbon ink electrodes. According to one embodiment, the kit comprises an assay module, and the assay module is used as a container for one or more other assay components provided in the kit. In such an embodiment, the one or more other assay components may include an ECL read buffer or one or more components of an ECL read buffer, for example, the read buffer or components thereof may be provided in one or more wells of a multi-well plate wells, optionally, in a dry form.

According to another embodiment, the kit comprises an assay module and the assay module is used as a container for at least one binding reagent. Optionally, the binding reagent is immobilized in the assay module. Optionally, a plurality of binding reagents are immobilized as an array of binding reagents in the assay module. The immobilized binding reagent and/or the array of immobilized binding reagents may be immobilized on electrodes (which may be carbon electrodes or carbon ink electrodes) within the assay module.

According to another embodiment, the kit comprises a multi-well assay plate having a plurality of wells, and the assay plate is used as a container for at least one binding reagent. Optionally, the binding reagent is immobilized in the plate. A plurality of wells within the plates may have binding reagents immobilized within them. The binding reagent in each of these wells may be the same for all of these wells, for some of these wells, or for none of these wells, Optionally, a plurality of binding reagents are immobilized as an array of binding reagents in each of these wells. The immobilized binding reagent and/or the array of immobilized binding reagents may be immobilized on electrodes (which may be carbon-based electrodes or, more specifically, carbon ink electrodes) within the wells.

Binding reagents that can be included in the kit (and/or within an assay module, immobilized or non-immobilized) include, but are not limited to, whole cells, cell surface antigens, subcellular particles (e.g., organelles or membrane fragments), exosomes, extracellular vesicles, membrane vesicles, liposomes, viruses, prions, dust mites or fragments thereof, viroids, antibodies, antigens, haptens, fatty acids, nucleic acids (and synthetic analogs), proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, second messengers, cellular metabolites, hormones, pharmacological agents, synthetic organic molecules, organometallic molecules, tranquilizers, barbiturates, alkaloids, steroids, vitamins, amino acids, sugars, lectins, recombinant or derived proteins, biotin, avidin, and/or streptavidin In one embodiment, the kit comprises a binding reagent that includes a lipid bilayer membrane (which may be provided in an assay module and optionally immobilized in an assay module) and an ECL read buffer (provided in one or more parts) that does not disrupt the lipid bilayer in this reagent. The read buffer may be surfactant free. Alternatively, the read buffer may contain surfactant, but at a concentration below the cmc for the surfactant. Alternatively, the read buffer may contain a mild surfactant (which may be present at a concentration above the cmc) that does not disrupt lipid bilayer membranes. In embodiments, the lipid bilayer membrane is derived from at least one of an intact cell, cell lysate, cell fragment, cell membrane, membrane ghost, organelle, organelle fragment, organelle membrane, virion, virion fragment, virion membrane, liposome, plasma membrane fragments, endosomes, clathrin-coated vesicles, endoplasmic reticulum fragments, synaptic vesicles, Golgi fragments, membrane subdomains, mitochondria, peroxisomes, lysosomes, liposomes, exosomes, extracellular vesicles, viral particles, viral-induced membrane enclosed particles shed from cells, or intact, organismally-derived lipid membrane bodies.

According to another embodiment, the kit comprises two or more, four or more, eight or more, 15 or more, or 25 or more assay modules or plates. According to one embodiment, the kit is contained in a resealable bag or container (e.g., a container having a zip-lock opening).

In embodiments, the present disclosure provides a kit comprising in one or more containers the following materials: N-butyldiethanolamine (BDEA) or 2-dibutylaminoethanol (DBAE), or both; a pH buffering component; and an ionic component.

In embodiments, one or more of the materials is provided in dry form. In embodiments, the kit further comprises a liquid diluent. In embodiments, the kit further comprises a surfactant. In embodiments, the kit does not comprise a surfactant or liquid diluent.

In embodiments, the present disclosure provides a kit comprising the compositions described herein and: an assay instrument; an assay consumable; an additional assay reagent; an assay sample; or a combination thereof. In embodiments, the kit comprises an assay instrument, wherein the assay instrument is configured to conduct ECL assays. In embodiments, the kit comprises an assay consumable and further comprises an electrode configured for use in an ECL assay. In embodiments, the electrode is a carbon-based electrode. In embodiments, the electrode is a screen-printed carbon ink electrode.

In embodiments, the kit comprises an additional assay reagent, wherein the additional assay reagent is a binding reagent. In embodiments, the binding reagent is labeled with an EU label. In embodiments, the label is an organometallic ruthenium complex. In embodiments, the kit comprises an additional assay reagent, wherein the additional assay reagent is a binding reagent and the additional assay reagent is immobilized on the electrode. In embodiments, the kit comprises an additional assay reagent, wherein the additional assay reagent is a binding reagent and the additional assay reagent is immobilized as an array on the electrode. In embodiments, the kit comprises an additional assay reagent, wherein the additional assay reagent is a binding reagent and the additional assay reagent is immobilized on a particle. In embodiments, the particle is magnetically collectable.

In embodiments, the kit comprises at least one assay sample, wherein the at least one assay sample includes an assay calibrator sample and/or an assay control sample.

5.9 Methods

Another aspect of the present disclosure relates to methods of using the buffers, reagents and/or compositions of the disclosure.

One embodiment of the disclosure relates to a method for conducting an electrochemiluminescence assay wherein electrochemiluminescence is induced in the presence of an ECL assay composition and/or read buffer of the disclosure. The electrochemiluminescence can be induced using a carbon-based electrode. A method according to this embodiment includes contacting an electrode with an ECL assay composition and/or read buffer, applying a voltage to the electrode and measuring the resulting electrochemiluminescence.

Another embodiment of the disclosure relates to a method tier measuring the quantity of ECL label wherein the label is induced to emit electrochemiluminescence in the presence of an ECL assay composition and; or read buffer of the disclosure, and the electrochemiluminescence is measured so as to measure the quantity of the ECL label. The electrochemiluminescence can be induced using a carbon-based electrode. A method according to this embodiment includes contacting an electrode with an ECL assay composition and/or read buffer, applying a voltage to the electrode, and measuring the resulting electrochemiluminescence, wherein a quantity of an ECL label is immobilized or otherwise held in proximity to said electrode. Alternatively, the quantity of the ECL label may be a component of the ECL assay composition and; or read buffer.

Another embodiment of the disclosure relates to a method for measuring the quantity of a binding complex comprising a binding assay reagent that is labeled with an ECL label, wherein the label is induced to emit electrochemiluminescence in the presence of an ECL assay composition and/or read buffer of the disclosure, and the electrochemiluminescence is measured so as to measure the quantity of the binding complex. The electrochemiluminescence can be induced using a carbon-based electrode. A method according to this embodiment includes (i) contacting an electrode with a binding reaction solution, wherein the electrode has an immobilized binding reagent immobilized thereon and the binding reaction solution comprises a labeled binding reagent that is labeled with an ECL label; (ii) forming a binding complex on the electrode comprising the immobilized binding reagent and the labeled binding reagent; (iii) contacting the binding complex on the electrode with a coreactant containing ECL assay composition; (iv) applying a voltage to the electrode in the presence of the ECL assay composition; and (v) measuring the resulting ECL to measure the quantity of the binding complex. Another method according to this embodiment includes (i) contacting a particle (or other solid phase binding reaction support) with a binding reaction solution, wherein the particle has an immobilized binding reagent immobilized thereon and the binding reaction solution comprises a labeled binding reagent that is labeled with an ECL label; (ii) forming a binding complex on the particle comprising the immobilized binding reagent and the labeled binding reagent; (iii) contacting the binding complex on the particle with a coreactant containing ECL assay composition; (iv) collecting the particle on an electrode (e.g., by gravity, centrifugation, filtering or, in the case of magnetic particles, by use of a magnet); (v) applying a voltage to the electrode in the presence of the ECL assay composition; and (vi) measuring the resulting ECL to measure the quantity of the binding complex. In further embodiments, the electrode comprises platinum, or consists essentially of platinum.

The method may use a "washed" assay format in which step (iii) of the methods described herein further comprises washing the electrode (or particle) to remove unbound labeled binding reagent and contacting the electrode (or particle) with an ECL coreactant-containing ECL read buffer to provide the ECL assay composition. Alternatively, a "non-washed" format may be used in which step (iii) does not include a wash step and comprises combining the binding reaction solution with an ECL coreactant-containing ECL read buffer to form the ECL assay composition. In an alternative "non-wash" format, the binding reaction solution is the coreactant-containing ECL assay composition.

Another embodiment of the disclosure involves methods for carrying out an assay for an analyte that employ the methods for measuring a binding complex, as described herein. In this embodiment, step (i) of the method may further comprise (a) contacting the electrode (or particle) with a sample containing a quantity of an analyte and/or (b) forming the binding reaction solution by combining the labeled binding reagent with the sample containing the quantity of the analyte. Furthermore, step (v) may comprise determining, from the quantity of binding complex, the quantity of analyte. Binding assay formats that can be carried out include, but are not limited to, (i) direct binding assays in which the labeled binding reagent is the analyte of interest and the immobilized binding reagent is a binding partner of the analyte, and the complex is formed by the direct binding of the two reagents; (ii) sandwich binding assays in which the immobilized and labeled binding reagents are both binding partners of an analyte of interest and the analyte binds the two binding partners to form the complex; (iii) competitive binding assays in which the immobilized binding reagent is a binding partner of the analyte and the labeled binding reagent is a competitor (e.g., the analyte or an analogue of the analyte) that competes with the immobilized binding reagent for binding to the analyte or, alternatively, the labeled binding reagent is a binding partner of the analyte and the immobilized binding reagent is a competitor that competes with the immobilized binding reagent for binding to the analyte (in the competitive formats, the labeled binding complex—formed by direct binding of the immobilized and labeled binding reagents—decreases in quantity with increasing quantity of analyte). Where the immobilized and/or labeled binding reagents are described herein as being binding partners or competitors of the analyte, it is well understood in the art that they could be replaced with reactive components that are, in turn, bound to the binding partners or competitors of the analyte, either directly or through additional reactive components.

Another embodiment of the disclosure relates to a method for measuring the quantity or activity of an analyte wherein the analyte reacts with, forms a complex with, or competes in a specific binding interaction with a labeled substance that comprises an ECL label, wherein the label is induced to emit electrochemiluminescence in the presence of an ECL coreactant-containing ECL assay composition and/or read buffer of the disclosure and the electrochemiluminescence is measured so as to measure the quantity or activity of the analyte. The electrochemiluminescence can be induced using a carbon-based electrode. The presence or activity of the analyte results in the label being bound to or released from an electrode (e.g., via the formation of a specific binding complex or via the cleavage or formation of a chemical bond). A method according to this embodiment may include contacting an electrode with an ECL assay composition and/or read buffer, applying a voltage to the electrode, and measuring the resulting electrochemiluminescence, wherein a quantity of an ECL label is immobilized or otherwise held in proximity to said electrode. Advantageously, the waveforms used to induce ECL in the presence of the ECL assay compositions and/or read buffers of the disclosure can be short in duration, for example, the duration of the waveforms may be less than 12 seconds, less than 6 seconds, less than 3 seconds, less than 2 seconds, or less than 1 second.

Approaches to using a measured amount of ECL to determine the quantity and/or concentration of an ECL label or an analyte in an ECL assay are established in the art and can include, for example, the use of calibration standards and/or calibration curves to establish the relationship between ECL signal and quantity and/or concentration of the label and/or analyte. Calibration may be carried out at different times, for example, during development of a method, during qualification of a specific lot of assay materials, or at the time of an assay measurement. Calibration may also be carried out using calculations based on the known physical and chemical behaviors of the assay components and instrumentation.

The embodiments of the disclosure can be used to test a variety of samples which may contain an analyte or activity of interest. Such samples may be in solid, emulsion, suspension, liquid, or gas form. They may be, but are not limited to, samples containing or derived from, for example, cells (live or dead) and cell-derived products, immortalized cells, cell fragments, cell fractions, cell lysates, organelles, cell membranes, hybridoma, cell culture supernatants (including supernatants from antibody producing organisms such as hybridomas), waste or drinking water, food, beverages, pharmaceutical compositions, blood, serum, plasma, hair, sweat, urine, feces, tissue, biopsies, effluent, separated and/or fractionated samples, separated and/or fractionated liquids, organs, saliva, animal parts, animal byproducts, plants, plant parts, plant byproducts, soil, minerals, mineral deposits, water, water supply, water sources, filtered residue from fluids (gas and liquid), swipes, absorbent materials, gels, cytoskeleton, protein complexes, unfractionated samples, unfractionated cell lysates, endocrine factors, paracrine factors, autocrine factors, cytokines, hormones, cell signaling factors and or components, second messenger signaling factors and/or components, cell nucleus/nuclei, nuclear fractions, chemicals, chemical compositions, structural biological components, skeletal (ligaments, tendons) components, separated and/or fractionated skeletal components, hair, fur, feathers, hair fractions and/or separations, skin, skin samples, skin fractions, dermis, endodermis, eukaryotic cells, prokaryotic cells, fungus, yeast, antibodies, antibody fragments, immunological factors, immunological cells, drugs, therapeutic drugs, oils, extracts, mucous, fur, oils, sewage, environmental samples, organic solvents or air. The sample may further comprise, for example, water, organic solvents e.g., acetonitrile, dimethyl sulfoxide, dimethyl formamide, n-methyl-pyrrolidone or alcohols) or mixtures thereof.

Analytes that may be measured include, but are not limited to, whole cells, cell surface antigens, subcellular particles (e.g., organelles or membrane fragments), exosomes, extracellular vesicles, liposomes, membrane vesicles, viruses, prions, dust mites or fragments thereof, viroids, antibodies, antigens, haptens, fatty acids, nucleic acids (and synthetic analogs), proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, second messengers, cellular metabolites, hormones, pharmacological agents, synthetic organic molecules, organometallic molecules, tranquilizers, barbiturates, alkaloids, steroids, vitamins, amino acids, sugars, lectins, recombinant or derived proteins, biotin, avidin, streptavidin, or inorganic molecules present in the sample. Activities that may be measured include, but are not limited to, the activities of phosphorylases, phosphatases, esterases, trans-glutaminases, nucleic acid damaging activities, transferases, oxidases, reductases, dehydrogenases, glycosidases, ribosomes, protein processing enzymes (e.g., proteases, kinases, protein phosphatases, ubiquitin-protein ligases, etc.), nucleic acid processing enzymes (e.g., polymerases, nucleases, integrases, ligases, helicases, telomerases, etc.), cellular receptor activation, second messenger system activation, etc.

Whole cells may be animal, plant, or bacteria, and may be viable or dead. Examples include plant pathogens such as fungi and nematodes. The term "subcellular particles" is meant to encompass, for example, subcellular organelles, membrane particles as from disrupted cells, fragments of cell walls, ribosomes, multi-enzyme complexes, and other particles which can be derived from living organisms. Nucleic acids include, for example, chromosomal DNA, plasmid NA, viral DNA, and recombinant DNA derived from multiple sources. Nucleic acids also include RNA's, for example messenger RNA's, ribosomal RNA's and transfer RNAs. Polypeptides include, for example, enzymes, transport proteins, receptor proteins, and structural proteins such as viral coat proteins. Preferred polypeptides are enzymes and antibodies. Particularly preferred polypeptides are monoclonal antibodies. Hormones include, for example, insulin and T4 thyroid hormone. Pharmacological agents include, for example, cardiac glycosides. It is of course within the scope of this disclosure to include synthetic substances which chemically resemble biological materials, such as synthetic polypeptides, synthetic nucleic acids, and synthetic membranes, vesicles and liposomes. The foregoing is not intended to be a comprehensive list of the biological substances suitable for use in this disclosure, but is meant only to illustrate the wide scope of the disclosure.

In embodiments, the present disclosure provides a method for producing a composition comprising combining: N-butyldiethanolamine (BDEA) or 2-dibutylaminoethanol (DBAE), or both; a buffering component; and an ionic component. In embodiments of the method, one or more of the materials is provided in dry form.

In embodiments, the present disclosure provides a method for generating ECL comprising: contacting an electrode with a composition described herein and an ECL label; applying a voltage to the electrode; and generating ECL.

In embodiments, the present disclosure provides a method for measuring the quantity of an ECL label comprising contacting an electrode with a composition described herein and the ECL label; applying a voltage to the electrode; generating ECL; measuring the ECL; and determining, from the measured ECL, the quantity of the label.

In embodiments, the present disclosure provides a method for measuring the quantity of a binding complex comprising a binding reagent linked to an ECL label, the method comprising contacting an immobilized binding reagent on an electrode with a labeled binding reagent comprising an ECL label; forming a binding complex on the electrode comprising the immobilized binding reagent and the labeled binding reagent; contacting the binding complex on the electrode with a composition as described herein; applying a voltage to the electrode in the presence of the composition; generating ECL; and measuring the ECL to determine the quantity of the binding complex on the electrode.

In embodiments, the present disclosure provides a method for measuring the quantity of a binding complex comprising a binding reagent linked to an ECL label, the method comprising contacting an immobilized binding reagent on a particle with a labeled binding reagent comprising an ECL label; forming a binding complex on the particle comprising the immobilized binding reagent and the labeled binding reagent; contacting the binding complex on the particle with a composition as described herein; collecting the particle on an electrode; applying a voltage to the electrode in the presence of the composition; generating ECL; and measuring the ECL to determine the quantity of the binding complex on the electrode. In embodiments, the method further comprises washing the electrode after formation of the binding complex and prior to and/or during contacting the electrode with the composition.

In embodiments, the present disclosure provides a method for measuring the quantity of a binding complex comprising a binding reagent linked to an ECL label, the method comprising contacting an immobilized binding reagent on a particle with a labeled binding reagent comprising an ECL label; forming a binding complex on the particle comprising the immobilized binding reagent and the labeled binding reagent; contacting the binding complex on the particle with a composition as described herein; collecting the particle on an electrode; applying a voltage to the electrode in the presence of the composition; generating ECL; and measuring the ECL to determine the quantity of the binding complex on the electrode. In embodiments, the particle is a magnetically collectable and the particle is collected on the electrode using a magnetic field. In embodiments, the method further comprises washing the particle after formation of the binding complex and prior to and/or during contacting the particle with the composition.

In embodiments of the method, the immobilized binding reagent and labeled binding reagent bind directly to each other. In embodiments of the method, the immobilized binding reagent and labeled binding reagent bind indirectly to each other through other binding species. In embodiments, the immobilized binding reagent and the labeled binding reagent comprise: (i) a binding partner of an analyte of interest, (ii) the analyte of interest or an analogue and/or competitor thereof, or (iii) a reactive component capable of binding with species (i) or (ii).

In embodiments, the present disclosure provides a method for measuring the quantity of an analyte, the method comprising: contacting an immobilized binding reagent on an electrode with a labeled binding reagent comprising an ECL label and the analyte (or a sample comprising the analyte); forming a binding complex on the electrode comprising the immobilized binding reagent and the labeled binding reagent; contacting the binding complex on the electrode with a composition as described herein; applying a voltage to the electrode in the presence of the composition; generating ECL; and measuring the ECL to determine the quantity of the analyte. In embodiments, the method further comprises washing the electrode after formation of the binding complex and prior to and/or during contacting the electrode with the composition. In embodiments, the method is configured to carry out a multiplexed measurement of a plurality of analytes, and the electrode has immobilized thereon an array of immobilized binding reagents for the plurality of analytes.

In embodiments, the present disclosure provides a method for measuring the quantity of an analyte, the method comprising: contacting an immobilized binding reagent on a particle with a labeled binding reagent comprising an ECL, label and an analyte (or a sample comprising the analyte); forming a binding complex on the particle comprising the immobilized binding reagent and the labeled binding reagent; contacting the binding complex on the particle with a composition described herein; collecting the particle on an electrode; applying a voltage to the electrode in the presence of the composition; generating ECL; and measuring the ECL to determine the quantity of the analyte. In embodiments, the particle is a magnetically collectable particle and the particle is collected on the electrode using a magnetic field. In embodiments, the method further comprises washing the particle after formation of the binding complex and prior to and/or during contacting the particle with the composition. In embodiments, the immobilized binding reagent and the labeled binding reagent comprise (i) a binding partner of the analyte, (ii) the analyte or an analogue and; or competitor thereof, or (iii) a reactive component capable of binding with species (i) or (ii).

In embodiments of the method, the electrode is a carbon-based electrode. In embodiments, the electrode is a screen-printed carbon ink electrode. In embodiments, the ECL is imaged using a camera. In embodiments, the ECL is measured using a photodiode. In embodiments, the electrode is in a multi-well plate assay consumable. In embodiments, the electrode is in a flow cell. In embodiments, the electrode is platinum.

5.10 Compositions

The following are some non-limiting examples of embodiments of the disclosed ECL assay compositions and/or read buffers.

In one embodiment of the disclosed composition the following components can be included: BDEA at a concentration of about 75 mM to about 300 mM; Tris(hydroxymethyl)aminomethane (TRIS) buffer, at a concentration of zero or about 100 mM to about 300 mM; TRITON X-100 ($C_{14}H_{22}O(C_2H_4O)_n$) surfactant at a concentration of zero or about 0.2 mM to about 10 mM; chloride ion at a concentration of zero or about 200 mM to about 1,000 mM; a non-phenol-containing non-ionic surfactant at a concentration of zero or about 0.2 mM to about 10 mM; glycerol at a concentration of zero or about 200 mM to about 800 mM; and $Na_2SO_4$ at a concentration of zero or about 200 mM to about 800 mM.

In another embodiment of the disclosed composition, the following components can be included: BDEA at a concentration of about 75 mM to about 300 mM, TRIS at a concentration of about 100 mM to about 300 mM; chloride ion at a concentration of about 200 mM to about 1,000 mM; TRITON X-100 at a concentration of about 0.2 to about 10 nM.

In another embodiment of the disclosed composition, the following components can be included: BDEA at a concentration of about 150 mM; TRIS at a concentration of about 200 mM; KCl at a concentration of about 50 mM; TRITON X-100 at a concentration of about 1 mM; and NaCl at a concentration of about 800 mM.

In another embodiment of the disclosed composition, the following components can be included: BDEA at a concentration of about 75 mM to about 300 mM, TRIS at a concentration of about 100 mM to about 300 mM; chloride ion at a concentration of about 200 mM to about 1,000 mM; a non-phenol-containing non-ionic surfactant at a concentration of about 0.2 to about 5 mM, wherein the surfactant is KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20.

In another embodiment of the disclosed composition, the following components can be included: BDEA at a concentration of about 150 mM; TRIS at a concentration of about 200 mM; KCl at a concentration of about 50 mM, a non-phenol-containing non-ionic surfactant at a concentration of about 1 mM; and NaCl at a concentration of about 800 mM, wherein the surfactant is KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20.

In embodiments, the present disclosure provides a composition comprising N-butyldiethanolamine (BDEA) or 2-dibutylaminoethanol (DBAE), or both; a pH buffering component; and an ionic component. In embodiments, the present disclosure provides a composition consisting essentially of N-butyldiethanolamine (BDEA) or 2-dibutylaminoethanol (DBAE), or both; a pH buffering component; and an ionic component.

In embodiments, the invention provides a composition comprising an alkyl diethanolamine of the following formula: $(HOCH_2CH_2CH_2)_2N-CH^1-CHR^2-CHR^3-R^4$), wherein $R^1$, $R^2$, $R^3$ and $R^4$ are each independently —H, —$CH_3$, —$CH_2CH_3$, or —$CH(CH_3)_2$, for example, R $R^1$, $R^2$, $R^3$ and $R^4$ are each H, at a concentration of about 75 mM to about 300 mM; Tris(hydroxymethyl)aminomethane (TRIS) buffer, at a concentration of zero or about 100 mM to about 300 mM; TRITON X-100 ($C_{14}H_{22}O(C_2H_4O)_n$) surfactant at a concentration of zero or about 0.2 mM to about 10 mM; chloride ion at a concentration of zero or about 200 mM to about 1,000 mM, a non-phenol-containing non-ionic surfactant at a concentration of zero or about 0.2 mM to about 10 mM, glycerol at a concentration of zero or about 200 mM, to about 800 mM; and $Na_2SO_4$ at a concentration of zero or about 200 mM to about 800 mM.

In another embodiment of the disclosed composition, the following components can be included: an alkyl diethanolamine of the following formula: $(HOCH_2CH_2)_2N-CHR^1-CHR^2-CHR^3-R^4$), wherein $R^1$, $R^2$, $R^3$ and $R^4$ are each independently —H, —$CH_3$, —$CH_2CH_3$, or —$CH(CH_3)_2$, for example, R $R^1$, $R^2$, $R^3$ and $R^4$ are each H, at a concentration of about 75 mM to about 300 mM, TRIS at a concentration of about 100 mM to about 300 mM; chloride ion at a concentration of about 200 mM to 1,000 mM; TRITON X-100 at a concentration of about 0.2 to about 10 mM.

In another embodiment of the disclosed composition, the following components can be included: an alkyl diethanolamine of the following formula: $(HOCH_2CH_2)_2N-CHR^1-CHR^2-CHR^3-R^4$), wherein $R^1$, $R^2$, $R^3$ and $R^4$ are each independently —H, —$CH_3$, —$CH_2CH_3$, or —$CH(CH_3)_2$, for example, R $R^1$, $R^2$, $R^3$ and $R^4$ are each H, at a concentration of about 150 mM; TRIS at a concentration of about 200 mM; KCl at a concentration of about 50 mM TRITON X-100 at a concentration of about 1 mM; and NaCl at a concentration of about 800 mM.

In another embodiment of the disclosed composition, the following components can be included: an alkyl diethanolamine of the following formula: $(HOCH_2CH_2)_2N-CHR^1-CHR^2-CHR^3-R^4$), wherein $R^1$, $R^2$, $R^3$ and $R^4$ are each independently —H, —$CH_3$, —$CH_2CH_3$, or —$CH(CH_3)_2$, for example, R $R^1$, $R^2$, $R^3$ and $R^4$ are each H, at a concentration of about 75 mM to about 300 mM, TRIS at a concentration of about 100 mM to about 300 mM; chloride ion at a concentration of about 200 mM to about 1,000 mM; a non-phenol-containing non-ionic surfactant at a concentration of about 0.2 to about 5 mM, wherein the surfactant is KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4; BRIJ 58 or TWEEN 20.

In another embodiment of the disclosed composition, the following components can be included: an alkyl diethanolamine of the following formula: $(HOCH_2CH_2)_2N-CHR^1-CHR^2-CHR^3-R^4$), wherein $R^1$, $R^2$, $R^3$ and $R^4$ are each independently —H, —$CH_3$, —$CH_2CH_3$, or —CH $(CH_3)_2$, for example, R $R^1$, $R^2$, $R^3$ and $R^4$ are each H, at a concentration of about 150 mM; TRIS at a concentration of about 200 mM; KCl at a concentration of about 50 mM; a non-phenol-containing non-ionic surfactant at a concentration of about 1 mM; and NaCl at a concentration of about 800 mM, wherein the surfactant is KOLLIPHOR P-407, PLURONIC P-123, PLURONIC PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20.

In embodiments, the compositions of the present disclosure further comprise at least one of a surfactant; a liquid diluent; an ECL label; a binding reagent for a binding assay; a preservative; a biocide; an anti-foaming agent; a perchlorate compound; a coloring agent; or a tracer chemical.

In embodiments, the present disclosure provides a composition consisting of N-butyldiethanolamine (BDEA) or 2-dibutylaminoethanol (DBAE), or both; a pH buffering component; and an ionic component.

In embodiments, the pH buffering component is tris (hydroxymethyl)-aminomethane (Tris).

In embodiments, the pH buffering component is tris (hydroxymethyl)-aminomethane (Tris) and the composition comprises a surfactant. In embodiments, the surfactant comprises a phenol ether. In embodiments, the surfactant is TRITON X-100, in embodiments, the surfactant does not comprise a phenol ether. In embodiments, the composition does not disrupt lipid bilayer membranes. In embodiments, the surfactant is KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the surfactant is TWEEN-20. In embodiments, the surfactant is PEG(18) tridecyl ether.

In embodiments, the compositions of the present disclosure comprise a surfactant that does not comprise a phenol ether. In embodiments, the composition does not disrupt lipid bilayer membranes. In embodiments, the surfactant is KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the surfactant is TWEEN-20. In embodiments, the surfactant is PEG(18) tridecyl ether. In embodiments, the pH buffering component is phosphate, HEPES, glycylglycine, borate, acetate or citrate.

In embodiments, the ECL coreactant is BDEA. In embodiments, the ECL coreactant is DBAE. In embodiments, an ECL generated by an ECL label in the presence of the composition changes, on average, by less than 1% per ° C. over the temperature range of 18° C. to 30° C. In embodiments, the ECL is generated from an electrochemiluminescent ruthenium organometallic complex in proximity to a carbon-based electrode.

In embodiments of the compositions described herein, the pH is between 6 and 9. In embodiments, the pH is between 7 and 8. In embodiments, the pH is between 7.6 and 7.9. In embodiments, the pH is about 7.8. In embodiments of the compositions described herein, a slope of a change in ECL with pH for an ECL generated by an ECL label in the presence of the composition is less than 10% per pH unit. In embodiments, the ECL is generated from an electrochemiluminescent ruthenium organometallic complex in proximity to a carbon-based electrode.

In embodiments of the compositions described herein, the ionic component comprises NaCl. In embodiments, the ionic component comprises KCl. In embodiments, the ionic component comprises LiCl. In embodiments, the ionic component comprises chloride ion.

In embodiments, the compositions described herein comprise a liquid diluent. In embodiments, the liquid diluent is water and the composition is substantially aqueous.

In embodiments of the compositions described herein, the concentration of the ECL coreactant is between about 10 mM and about 800 mM. In embodiments, the concentration of the ECL coreactant is between about 75 mM and about 300 mM, in embodiments, the concentration of the ECL coreactant is between about 100 mM and about 150 mM. In embodiments of the compositions described herein, a change in the concentration of the ECL coreactant from 0.8 to 1.2 times the nominal value provides less than a 10% change in an ECL generated by an ECL label in the presence of the composition. In embodiments, the ECL is generated from an electrochemiluminescent ruthenium organometallic complex in proximity to a carbon-based electrode. In embodiments, the ECL from the ECL label is generated from an electrochemiluminescent ruthenium organometallic complex in proximity to a carbon-based electrode and/or ECL in the absence of an ECL label is generated at a carbon-based electrode.

In embodiments, the concentration of the pH buffering component is between about 10 mM and about 800 mM. In embodiments, the concentration of the pH buffering component is between about 100 mM and about 300 mM. In embodiments, the concentration of the pH buffering component is between about 150 mM and about 250 mM.

In embodiments, the compositions described herein have an ionic strength of greater than 0.3 M. In embodiments, the compositions described herein have an ionic strength of greater than 0.5 M. In embodiments, the compositions described herein have an ionic strength of greater than 0.8 M. In embodiments, the compositions described herein have an ionic strength of greater than 1.0 M. In embodiments, the composition comprises chloride ion and the concentration of the chloride ion is greater than about 0.25 M. In embodiments, the composition comprises chloride ion and the concentration of the chloride ion is greater than about 0.5 M. In embodiments, the composition comprises chloride ion and the concentration of the chloride ion is greater than about 0.75 M. In embodiments, the composition comprises chloride ion and the concentration of the chloride ion is greater than about 1.0 M.

In embodiments of the compositions described herein, the pH buffering component is selected such that the composition provides at least a 20% decrease in an ECL generated by an ECL label and/or at least a 20% decrease in background ECL generated in the absence of an ECL label, compared with the same composition that contains phosphate as the pH buffering component.

In embodiments, non-specific binding (NSB) in an immunoassay is lower with the composition containing the ionic component compared to the same composition that contains no ionic component.

In embodiments, the compositions described herein do not include a liquid diluent, and the compositions are provided in dry form.

In embodiments, the present disclosure provides a composition comprising N-butyldiethanolamine (BDEA) or 2-dibutylaminoethanol (DBAE), or both; a pH buffering component; and an ionic component. In embodiments, the present disclosure provides a composition comprising N-butyldiethanolamine (BDEA) or 2-dibutylaminoethanol (DBAE), or both; a pH buffering component; an ionic component; and a surfactant. In embodiments, the present disclosure provides a composition comprising N-butyldiethanolamine (BDEA) or 2-dibutylaminoethanol (DBAE), or both; a buffering component; an ionic component; and a liquid diluent. In embodiments, the present disclosure provides a composition comprising N-butyldiethanolamine (BDEA) or 2-dibutylaminoethanol (DBAE), or both; a pH buffering component; an ionic component; a surfactant; and a liquid diluent.

In some embodiments, the compositions of the present disclosure further comprise at least one of an ECL label; a binding reagent for a binding assay; a preservative; a biocide; an anti-foaming agent; a perchlorate compound; a coloring agent; a tracer chemical; a solid support; or combinations thereof.

In embodiments, the present disclosure provides a composition consisting essentially of N-butyldiethanolamine (BDEA) or 2-dibutylaminoethanol (DBAE), or both; a pH buffering component; and an ionic component. In embodiments, the present disclosure provides a composition consisting essentially of N-butyldiethanolamine (BDEA) or 2-dibutylaminoethanol (DBAE), or both; a pH buffering component; an ionic component; and a surfactant. In embodiments, the present disclosure provides a composition consisting essentially of N-butyldiethanolamine (BDEA) or 2-dibutylaminoethanol (DBAE), or both; a buffering component; an ionic component; and a liquid diluent. In embodiments, the present disclosure provides a composition consisting essentially of N-butyldiethanolamine (BDEA) or 2-dibutylaminoethanol (DBAE), or both; a pH buffering component; an ionic component; a surfactant; and a liquid diluent.

In embodiments, the present disclosure provides a composition consisting of N-butyldiethanolamine (BDEA) or 2-dibutylaminoethanol (DBAE), or both; a pH buffering component; and an ionic component. In embodiments, the present disclosure provides a composition consisting of N-butyldiethanolamine (BDEA) or 2-dibutylaminoethanol (DBAE), or both; a pH buffering component; an ionic component; and a surfactant. In embodiments, the present disclosure provides a composition consisting of N-butyldiethanolamine (BDEA) or 2-dibutylaminoethanol (DBAE), or both; a pH buffering component; an ionic component; and a liquid diluent. In embodiments, the present disclosure provides a composition consisting of N-butyldiethanolamine (BDEA) or 2-dibutylaminoethanol (DBAE), or both; a pH buffering component; an ionic component; a surfactant; and a liquid diluent.

In embodiments, the compositions described herein comprise about 75 mM to about 300 mM of BDEA or DBAE, about 200 mM of a pH buffering component, and greater than or about 750 mM of an ionic component. In embodiments, the composition comprises about 75 mM to about 300 mM of BDEA or DBAE, about 200 mM of a pH buffering component, greater than or about 750 mM of an ionic component, and about 1.0 mM of a surfactant. In embodiments, the composition comprises about 75 mM to about 300 mM of BDEA or DBAE, about 200 mM of a pH buffering component, greater than or about 750 mM of an ionic component, and an aqueous liquid diluent. In embodiments, the composition comprises about 75 mM to about 300 mM of BDEA or DBAE, about 200 mM of a pH buffering component, greater than or about 750 mM of an ionic component, about 1.0 mM of a surfactant, and an aqueous liquid diluent. In embodiments, the pH of the composition is about 7.0 to about 8.0. In embodiments, the pH of the composition is about 7.5. In embodiments, the pH of the composition is about 7.8.

In embodiments, the compositions described herein comprise about 150 mM of BDEA or DBAE, about 100 mM to about 300 mM of a pH buffering component, and greater than or about 750 mM of an ionic component. In embodiments, the composition comprises about 150 mM of BDEA or DBAE, about 100 mM to about 300 mM of a pH buffering component, greater than or about 750 mM of an ionic component, and about 1.0 mM of a surfactant. In embodiments, the composition comprises about 150 mM of BDEA or DBAE, about 100 mM to about 300 mM of a pH1 buffering component, greater than or about 750 mM of an ionic component, and an aqueous liquid diluent. In embodiments, the composition comprises about 150 tall of BDEA or DBAE, about 100 mM to about 300 mM of a pH buffering component, greater than or about 750 mM of an ionic component, about 1.0 mM of a surfactant, and an aqueous liquid diluent. In embodiments, the pH of the composition is about 7.0 to about 8.0. In embodiments, the pH of the composition is about 7.5. In embodiments, the pH of the composition is about 7.8.

In embodiments, the compositions described herein comprise about 150 mM of BDEA or DBAE, about 200 mM of a pH buffering component, and about 500 mM to about 1500 mM of an ionic component. In embodiments, the composition comprises about 150 mM of BDEA or DBAE, about 200 mM of a pH buffering component, about 500 mM to about 1500 mM of an ionic component, and about 1.0 mM of a surfactant. In embodiments, the composition comprises about 150 mM of BDEA or DBAE, about 200 mM of a pH buffering component, about 500 mM to about 1500 mM of an ionic component, and an aqueous liquid diluent. In embodiments, the composition comprises about 150 mM of BDEA or DBAE, about 200 mM of a pH buffering component, about 500 mM, to about 1500 mM of an ionic component, about 1.0 mM of a surfactant, and an aqueous liquid diluent. In embodiments, the pH of the composition is about 7.0 to about 8.0. In embodiments, the pH of the composition is about 7.5. In embodiments, the pH of the composition is about 7.8.

In embodiments, the compositions described herein comprise about 75 mM to about 300 mM of an ECL coreactant selected from BDEA and DBAE, about 200 mM of a pH buffering component, and greater than or about 750 mM of an ionic component. In embodiments, the composition comprises about 75 mM to about 300 mM of an ECL coreactant selected from BDEA and DBAEBDEA or DBAE, about 200 mM of a pH buffering component, greater than or about 750 mM of an ionic component, and about 0.2 to about 10 mM of a surfactant. In embodiments, the composition comprises about 150 mM of BDEA or DBAE, about 200 mM of a pH buffering component, greater than or about 750 mM of an ionic component, and an aqueous liquid diluent. In embodiments, the composition comprises about 150 mM of BDEA or DBAE, about 200 mM of a pH buffering component, greater than or about 750 mM of an ionic component, about 0.2 to about 10 mM of a surfactant, and an aqueous liquid diluent. In embodiments, the pH of the composition is about 7.0 to about 8.0. In embodiments, the pH of the composition is about 7.5. In embodiments, the pH of the composition is about 7.8.

In embodiments, the compositions described herein comprise about 150 mM of BDEA or DBAE, about 200 mM of a pH buffering component, and greater than or about 750 mM of an ionic component. In embodiments, the composition comprises about 150 mM of BDEA or DBAE, about 200 mM of a pH buffering component, greater than or about 750 mM of an ionic component, and about 0.2 to about 10 mM of TRITON X-100. In embodiments, the composition comprises about 150 mM of BDEA or DBAE, about 200 mM of a pH buffering component, about greater than or about 750 mM of an ionic component, and an aqueous liquid diluent. In embodiments, the composition comprises about 150 mM of BDEA or DBAE, about 200 mM of a pH buffering component, greater than or about 750 mM of an ionic component, about 0.2 to about 5.0 mM of TRITON X-100, and an aqueous liquid diluent, in embodiments, the pH of the composition is about 7.0 to about 8.0. In embodiments, the pH of the composition is about 7.5. In embodiments, the pH of the composition is about 7.8.

In embodiments, the compositions described herein comprise about 150 mM of BDEA or DBAE, about 200 mM of a pH buffering component, and greater than or about 750 mM of an ionic component. In embodiments, the composition comprises about 150 mM, of BDEA or DBAE, about 200 mM of a pH buffering component, greater than or about 750 mM of an ionic component, and about 0.2 to about 10 mM of a non-phenol-containing non-ionic surfactant. In embodiments, the composition comprises about 150 mM of BDEA or DBAE, about 200 mM of a pH buffering component, greater than or about 750 mM of an ionic component, and an aqueous liquid diluent. In embodiments, the composition comprises about 150 mM of BDEA or DBAE, about 200 mM of a pH buffering component, greater than or about 750 mM of an ionic component, about 0.2 to about 5.0 mM of a non-phenol-containing non-ionic surfactant, and an aqueous liquid diluent. In embodiments, the pH of the composition is about 7.0 to about 8.0. In embodiments, the pH of the composition is about 7.5. In embodiments, the pH of the composition is about 7.8.

In embodiments, the compositions described herein comprise about 150 mM of BDEA or DBAE, about 200 mM of a pH buffering component, and greater than or about 750 mM of an ionic component. In embodiments, the composition comprises about 150 mM of BDEA or DBAE, about 200 mM of a pH buffering component, greater than or about 750 mM of an ionic component, and about 0.2 to about 10 mM of PEWS) triethyl ether. In embodiments, the composition comprises about 150 mM of BDEA or DBAE, about 200 mM of a pH buffering component, greater than or about 750 mM of an ionic component, and an aqueous liquid diluent. In embodiments, the composition comprises about 150 mM of BDEA or DBAE, about 200 mM of a pH buffering component, greater than or about 750 mM of an ionic component, about 0.2 to about 10 mM of PEG(18) triethyl ether, and an aqueous liquid diluent. In embodiments, the pH of the composition is about 7.0 to about 8.0. In embodiments, the pH of the composition is about 7.5. In embodiments, the pH of the composition is about 7.8.

In embodiments, the compositions described herein comprise about 150 mM of BDEA or DBAE, about 200 trill of a pH buffering component, and greater than or about 750 mM of an ionic component. In embodiments, the composition comprises about 150 mM of BDEA or DBAE, about 200 mM of a pH buffering component, about or greater than 750 mM of an ionic component, and about 0.2 to about 10 mM of KOLLIPHOR P-407, PLURONIC P-123, or PEWS) tridecyl ether. In embodiments, the composition comprises about 150 mM of BDEA or DBAE, about 200 mM of a pH buffering component, about or greater than 750 mM of an ionic component, and an aqueous liquid diluent. In embodiments, the composition comprises about 150 mM of BDEA or DBAE, about 200 mM of a pH buffering component, about or greater than 750 mM of an ionic component, about 0.2 to about 10 mM of KOLLIPHOR P-407, PLURONIC P-123, or PEG(18) tridecyl ether, and an aqueous liquid diluent. In embodiments, the pH of the composition is about 7.0 to about 8.0. In embodiments, the pH of the composition is about 7.5. In embodiments, the pH of the composition is about 7.8.

In embodiments, the compositions described herein comprise about 75 mM to about 300 mM of BDEA, about 200 mM of Tris, and greater than or about 750 mM of chloride ion. In embodiments, the compositions comprise about 75 mM of BDEA, about 0 or about 100 to about 300 Tris, and greater than or about 750 mM of chloride ion. In embodiments, the compositions comprise about about 75 mM to about 300 mM of BDEA, about 200 mM of Tris, and about 0 or about 500 mM to about 1500 mM chloride ion. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of BDEA, about 200 mM of Tris, greater than or about 750 mM of chloride ion, and about 0.2 iris of TRITON X-100. In embodiments, the compositions comprise about 75 mM to about 300 mM of BDEA, about 200 mM of Tris, greater than or about 750 mM of chloride ion, and about 1.0 mM of TRITON X-100. In embodiments, the compositions comprise about 75 mM to about 300 mM of BDEA, about 200 mM of Tris, greater than or about 750 mM of chloride ion, and about 5 mM of TRITON X-100. In embodiments, the compositions comprise about 75 mM to about 300 mM of BDEA, about 200 mM of Tris, greater than or about 750 mM of chloride ion, and about 10 mM of TRITON X-100. In embodiments, the compositions comprise about 75 mM to about 300 trio of BDEA, about 200 mM of Tris, greater than or about 750 mM of chloride ion, and a concentration of TRITON K-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of BDEA, about 200 mM of Tris, greater than or about 750 mM of chloride ion, and about 0.2 mM of a non-phenol-containing non-ionic surfactant. In embodiments, the compositions comprise about 75 mM to about 300 mM of BDEA, about 200 mM of Tris, greater than or about 750 mM of chloride ion, and about 1.0 mM of a non-phenol-containing non-ionic surfactant. In embodiments, the compositions comprise about 75 mM to about 300 mM of BDEA, about 200 mM of Tris, greater than or about 750 mM of chloride ion, and about 5 mM of a non-phenol-containing non-ionic surfactant, in embodiments, the compositions comprise about 75 mM to about 300 mM of BDEA, about 200 mM of Tris, greater than or about 75 mM of chloride ion, and about 10 mM of a non-phenol-containing non-ionic surfactant. In embodiments, the compositions comprise about 75 mM to about 300 mM of BDEA, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of BDEA, about 200 mM of Tris, greater than or about 750 mM of chloride ion, and about 0.2 mM of KOLLIPHOR P-407, PLURONIC P-123, PLURONIC L-121, PLURONIC 31R1 THROW 701, 2,4,7,9-tetramethyl-d-decyne-4,7-diol ethoxylate, PEG(18) tridecyl ether, BRIJ L4. BRIJ 58 or TWEEN 20. In embodiments, the compositions comprise about 75 mM to about 300 mM of BDEA, about 200 mM of Tris, greater than or about 750 mM of chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM to about 300 mM of BDEA, about 200 mM of Tris, greater than or about 750 mM of chloride ion, and about 5.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM to about 300 mM of BDEA, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM to about 300 mM of BDEA, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(1.8) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of BDEA, about 200 mM of Tris, greater than or about 750 mM of chloride ion, and about 0.2 mM of KOLLIPHOR P-407, PLURONIC P-123, or PEG(18) tridecyl ether. In embodiments, the compositions comprise about 75 mM to about 300 mM of BDEA, about 200 mM of Tris, greater than or about 750 mM of chloride ion, and about 1.0 mM of KOLLIPHOR P-407, PLURONIC P-123, or PEG(18) tridecyl ether. In embodiments, the compositions comprise about 75 mM to about 300 mM of BDEA, about 200 mM of Tris, greater than or about 750 mM of chloride ion, and about 5.0 mM of KOLLIPHOR P-407, PLURONIC P-123, or PEG(18) tridecyl ether. In embodiments, the compositions comprise about 75 mM to about 300 mM of BDEA, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 75 mM to about 300 mM of BDEA, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of BDEA, about 200 mM of Tris, greater than or about 750 mM of chloride ion, and about 0.2 mM of PEG(18) tridecyl ether. In embodiments, the compositions comprise about 75 mM to about 300 mM of BDEA, about 200 mM of Tris, greater than or about 750 mM of chloride ion, and about 1.0 mM of PEWS) tridecyl ether. In embodiments, the compositions comprise about 75 mM to about 300 mM of BDEA, about 200 mM of Tris, greater than or about 750 mM of chloride ion, and about 5 mM of PEG(18) tridecyl ether. In embodiments, the compositions comprise about 75 mM to about 300 mM of BDEA, about 200 mM of Tris, greater than or about 750 mM of chloride ion, and about 10 mM, of PEG(18) tridecyl ether. In embodiments, the compositions comprise about 75 mM to about 300 mM of BDEA, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of BDEA, about 200 mM of Tris, and about 500 mM to about 1500 mM of chloride ion. In embodiments, the compositions comprise about 75 mM of BDEA, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 75 mM of BDEA, about 200 mM of Tris, greater than or about 750 mM of chloride ion, and about 0.2 mM to about 10 mM, of TRITON X-100. In embodiments, the compositions comprise about 75 mM of BDEA, about 200 mM of Tris, greater than or about 750 mM of chloride ion, and about 0.2 mM of TRITON X-100. In embodiments, the compositions comprise about 75 mM of BDEA, about 200 mM of Tris, greater than or about 750 mM chloride ion, and about 1.0 mM of TRITON X-100, In embodiments, the compositions comprise about 75 mM of BDEA, about 200 mM of Tris, greater than or about 750 mM of chloride ion, and about 5 mM of TRITON X-100. In embodiments, the compositions comprise about 75 mM of BDEA, about 200 mM of Tris, greater than or about 750 mM of chloride ion, and about 10 mM of TRITON X-100. In embodiments, the compositions comprise about 75 mM of BDEA, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of BDEA, about 200 mM of Tris, greater than or about 750 mM of chloride ion, and about 0.2 mM to about 10 mM of a non-phenol-containing non-ionic surfactant. In embodiments, the compositions comprise about 75 mM of BDEA, about 200 mM of Tris, greater than or about 750 mM of chloride ion, and about 0.2 mM of a non-phenol-containing non-ionic surfactant. In embodiments, the compositions comprise about 75 mM of BDEA, about 200 mM of Tris, greater than or about 750 mM chloride ion, and about 1.0 mM of a non-phenol-containing non-ionic surfactant. In embodiments, the compositions comprise about 75 mM of BDEA, about 200 mM of Tris, greater than or about 750 mM of chloride ion, and about 5 mM of a non-phenol-containing non-ionic surfactant. In embodiments, the compositions comprise about 75 mM of BDEA, about 200 mM of Tris, greater than or about 750 mM of chloride ion, and about 10 mM of a non-phenol-containing non-ionic surfactant. In embodiments, the compositions comprise about 75 mM of BDEA, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of BDEA, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM of BDEA, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 75 mM of BDEA, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20, In embodiments, the compositions comprise about 75 mM of BDEA, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM, of BDEA, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20, In embodiments, the compositions comprise about 75 mM of BDEA, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of BDEA, about 200 mM of Tris, greater than or about 750 mM of chloride ion, and about 0.2 mM to about 10 mM of KOLLIPHOR P-407, PLURONIC P-123, or PEG(18) tridecyl ether. In embodiments, the compositions comprise about 75 mM of BDEA, about 200 mM of Tris, greater than or about 750 mM of chloride ion, and about 0.2 mM of KOLLIPHOR P-407, PLURONIC P-123, or PEG(I tridecyl ether. In embodiments, the compositions comprise about 75 mM of BDEA, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 75 mM of BDEA, about 200 mM of Tris, greater than or about 750 mM of chloride ion, and about 5 mM of KOLLIPHOR P-407, PLURONIC P-123, or PEG(18) tridecyl ether. In embodiments, the compositions comprise about 75 mM of BDEA, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 75 mM of BDEA, about 200 mM of Tris, greater than or about 750 mM, of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of BDEA, about 200 mM of Tris, greater than or about 750 mM of chloride ion, and about 0.2 mM to about 10 mM of PEG(18) tridecyl ether. In embodiments, the compositions comprise about 75 mM of BDEA, about 200 mM of Tris, greater than or about 750 mM of chloride ion, and about 0.2 mM of PEG(18) tridecyl ether. In embodiments, the compositions comprise about 75 mM of BDEA, about 200 mM of Tris, greater than or about 750 mM chloride ion, and about 1.0 mM of PEG(18) tridecyl ether. In embodiments, the compositions comprise about 75 mM of BDEA, about 200 mM of Tris, greater than or about 750 mM of chloride ion, and about 5 mM of PEG(18) tridecyl ether. In embodiments, the compositions comprise about 75 mM of BDEA, about 200 mM of Tris, greater than or about 750 mM of chloride ion, and about 10 mM of PEG(28) tridecyl ether. In embodiments, the compositions comprise about 75 mM, of BDEA, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of BDEA, about 200 mM of Tris, and about 500 mM to about 1500 mM of chloride ion. In embodiments, the compositions comprise about 100 mM of BDEA, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 100 mM of BDEA, about 200 mM of Tris, greater than or about 750 mM of chloride ion, and about 0.2 mM to about 10 mM of TRITON X-100. In embodiments, the compositions comprise about 100 mM of BDEA, about 200 mM of Tris, greater than or about 750 mM of chloride ion, and about 0.2 mM of TRITON X-100. In embodiments, the compositions comprise about 100 mM of BDEA, about 200 mM of Tris, greater than or about 750 mM chloride ion, and about 1.0 mM of TRITON X-100. In embodiments, the compositions comprise about 100 mM of BDEA, about 200 mM of Tris, greater than or about 750 mM of chloride ion, and about 5 mM of TRITON X-100. In embodiments, the compositions comprise about 100 mM of BDEA, about 200 mM of Tris, greater than or about 750 mM of chloride ion, and about 10 mM of TRITON X-100, In embodiments, the compositions comprise about 100 mM of BDEA, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of BDEA, about 200 mM of Tris, greater than or about 750 mM of chloride ion, and about 0.2 mM to about 10 mM of a non-phenol-containing non-ionic surfactant. In embodiments, the compositions comprise about 100 mM of BDEA, about 200 mM of Tris, greater than or about 750 mM of chloride ion, and about 0.2 mM of a non-phenol-containing non-ionic surfactant. In embodiments, the compositions comprise about 100 mM of BDEA, about 200 mM of Tris, greater than or about 750 mM chloride ion, and about 1.0 mM of a non-phenol-containing non-ionic surfactant. In embodiments, the compositions comprise about 100 mM of BDEA, about 200 mM of Tris, greater than or about 750 mM of chloride ion, and about 5 mM, of a non-phenol-containing non-ionic surfactant. In embodiments, the compositions comprise about 100 mM of BDEA, about 200 mM of Tris, greater than or about 750 mM of chloride ion, and about 10 mM of a non-phenol-containing non-ionic surfactant. In embodiments, the compositions comprise about 100 mM of BDEA, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of BDEA, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 100 mM of BDEA, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 100 mM of BDEA, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20, in embodiments, the compositions comprise about 100 mM of BDEA, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 100 mM of BDEA, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20, in embodiments, the compositions comprise about 100 mM of BDEA, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20 greater than its cmc. In embodiments, the pH of the composition is about 7.0 to about 8.0. In embodiments, the pH of the composition is about 7.5, In embodiments, the pH of the composition is about 7.8.

In embodiments, the compositions comprise about 100 mM of BDEA, about 200 mM of Tris, greater than or about 750 mM of chloride ion, and about 0.2 mM to about 10 mM of KOLLIPHOR P-407, PLURONIC P-123, or PEG(18) tridecyl ether. In embodiments, the compositions comprise about 100 mM of BDEA, about 200 mM of Tris, greater than or about 750 mM of chloride ion, and about 0.2 mM of KOLLIPHOR P-407, PLURONIC P-123, or PEG(18) tridecyl ether. In embodiments, the compositions comprise about 100 mM of BDEA, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 100 mM of BDEA, about 200 mM of Tris, greater than or about 750 mM of chloride ion, and about 5 mM of KOLLIPHOR P-407, PLURONIC P-123, or PEG(18) tridecyl ether. In embodiments, the compositions comprise about 100 mM of BDEA, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 100 mM of BDEA, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of BDEA, about 200 mM of Tris, greater than or about 750 mM of chloride ion, and about 0.2 mM to about 10 mM of PEG(18) tridecyl ether. In embodiments, the compositions comprise about 100 mM of BDEA, about 200 mM of Tris, greater than or about 750 mM of chloride ion, and about 0.2 mM of PEG(18) tridecyl ether. In embodiments, the compositions comprise about 100 mM of BDEA, about 200 mM of Tris, greater than or about 750 mM chloride ion, and about 1.0 mM of PEG(18) tridecyl ether. In embodiments, the compositions comprise about 100 mM of BDEA, about 200 mM of Tris, greater than or about 750 mM of chloride ion, and about 5 mM of PEG(18) tridecyl ether. In embodiments, the compositions comprise about 100 mM of BDEA, about 200 mM of Tris, greater than or about 750 mM of chloride ion, and about 10 mM of PEG(18) tridecyl ether. In embodiments, the compositions comprise about 100 mM of BDEA, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of BDEA, about 200 mM of Tris, and about 500 mM to about 1500 mM of chloride ion. In embodiments, the compositions comprise about 150 mM of BDEA, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 150 mM of BDEA, about 200 mM of Tris, greater than or about 750 mM of chloride ion, and about 0.2 mM to about 10 mM of TRITON X-100. In embodiments, the compositions comprise about 150 mM of BDEA, about 200 mM of Tris, greater than or about 750 mM of chloride ion, and about 0.2 mM of TRITON X-100. In embodiments, the compositions comprise about 150 mM of BDEA, about 200 mM of Tris, greater than or about 750 mM chloride ion, and about 1.0 mM of TRITON X-100. In embodiments, the compositions comprise about 150 mM of BDEA, about 200 mM of Tris, greater than or about 750 mM of chloride ion, and about 5 mM of TRITON X-100. In embodiments, the compositions comprise about 150 mM of BDEA, about 200 mM of Tris, greater than or about 750 mM of chloride ion, and about 10 mM of TRITON X-100. In embodiments, the compositions comprise about 150 mM of BDEA, about 200 mM of Tris, greater than or about 750 mkt of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of BDEA, about 200 mM of Tris, greater than or about 750 mM of chloride ion, and about 0.2 mM to about 10 mM of a non-phenol-containing non-ionic surfactant. In embodiments, the compositions comprise about 150 mM of BDEA, about 200 mM of Tris, greater than or about 750 mM of chloride ion, and about 0.2 mM of a non-phenol-containing non-ionic surfactant. In embodiments, the compositions comprise about 150 mM of BDEA, about 200 mM of Tris, greater than or about 750 mM chloride ion, and about 1.0 mM of a non-phenol-containing non-ionic surfactant. In embodiments, the compositions comprise about 150 mM of BDEA, about 200 mM of Tris, greater than or about 750 mM of chloride ion, and about 5 mM of a non-phenol-containing non-ionic surfactant. In embodiments, the compositions comprise about 150 mM of BDEA, about 200 mM of Tris, greater than or about 750 mM of chloride ion, and about 10 mM of a non-phenol-containing non-ionic surfactant. In embodiments, the compositions comprise about 150 mM of BDEA, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of BDEA, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 150 mM of BDEA, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 150 mM of BDEA, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TW 20. In embodiments, the compositions comprise about 150 mM of BDEA, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20, In embodiments, the compositions comprise about 150 mM of BDEA, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 150 mM of BDEA, about 200 mM of Tris, greater than or about 750 Wild of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of BDEA, about 200 mM of Tris, greater than or about 750 mM of chloride ion, and about 0.2 mM to about 10 mM of KOLLIPHOR P-407, PLURONIC P-123, or PEG(18) tridecyl ether. In embodiments, the compositions comprise about 150 mM of BDEA, about 200 mM of iris, greater than or about 750 mM of chloride ion, and about 0.2 mM of KOLLIPHOR P-407, PLURONIC P-123, or PEG(18) tridecyl ether. In embodiments, the compositions comprise about 150 mM of BDEA, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 150 mM of BDEA, about 200 mM of Tris, greater than or about 750 mM, of chloride ion, and about 5 mM of KOLLIPHOR P-407, PLURONIC P-123, or PEG(18) tridecyl ether. In embodiments, the compositions comprise about 150 mM of BDEA, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 150 mM of BDEA, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of BDEA, about 200 mM of Tris, greater than or about 750 mM of chloride ion, and about 0.2 mM to about 10 mM of PEG(18) tridecyl ether. In embodiments, the compositions comprise about 150 mM of BDEA, about 200 mM of Tris, greater than or about 750 mM of chloride ion, and about 0.2 mM of PEG(18) tridecyl ether. In embodiments, the compositions comprise about 150 mM of BDEA, about 200 mM of Tris, greater than or about 750 mM chloride ion, and about 1.0 mM of PEG (18) tridecyl ether, in embodiments, the compositions comprise about 150 nM of BDEA, about 200 mM of Tris, greater than or about 750 mM of chloride ion, and about 5 mM of PEG(18) tridecyl ether. In embodiments, the compositions comprise about 150 mM of BDEA, about 200 mM of Tris, greater than or about 750 mM of chloride ion, and about 10 mM of PEG(18) tridecyl other. In embodiments, the compositions comprise about 150 mM of BDEA, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of BDEA, about 200 mM of Tris, and about 500 mM to about 1500 mM of chloride ion. In embodiments, the compositions comprise about 200 mM of BDEA, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 200 mM of BDEA, about 200 mM of Tris, greater than or about 750 mM of chloride ion, and about 0.2 mM to about 10 mM of TRITON X-100. In embodiments, the compositions comprise about 200 mM of BDEA, about 200 mM of Tris, greater than or about 750 mM of chloride ion, and about 0.2 mM of TRITON X-100. In embodiments, the compositions comprise about 200 mM of BDEA, about 200 mM of Tris, greater than or about 750 mM chloride ion, and about 1.0 mM of TRITON X-100. In embodiments, the compositions comprise about 200 mM of BDEA, about 200 mM of Tris, greater than or about 750 mM of chloride ion, and about 5 mM of TRITON X-100. In embodiments, the compositions comprise about 200 mM of BDEA, about 200 mM of Tris, greater than or about 750 mM of chloride ion, and about 10 mM of TRITON X-100. In embodiments, the compositions comprise about 200 mM of BDEA, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of BDEA, about 200 mM of Tris, greater than or about 750 mM of chloride ion, and about 0.2 mM to about 10 mM of a non-phenol-containing non-ionic surfactant. In embodiments, the compositions comprise about 200 mM of BDEA, about 200 mM of Tris, greater than or about 750 mM of chloride ion, and about 0.2 mM of a non-phenol-containing non-ionic surfactant. In embodiments, the compositions comprise about 200 of BDEA, about 200 mM of Tris, greater than or about 750 mM chloride ion, and about 1.0 mM of a non-phenol-containing non-ionic surfactant. In embodiments, the compositions comprise about 200 mM of BDEA, about 200 mM of Tris, greater than or about 750 mM of chloride ion, and about 5 mM of a non-phenol-containing non-ionic surfactant. In embodiments, the compositions comprise about 200 mM of BDEA, about 200 mM of Tris, greater than or about 750 mM of chloride ion, and about 10 mM of a non-phenol-containing non-ionic surfactant. In embodiments, the compositions comprise about 200 mM of BDEA, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of BDEA, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of BDEA, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 200 mM of BDEA, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of BDEA, about 200 mM of Tris, greater than or about 750 mM of chloride ion, and about 5 mM of KOLLIPHOR. P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of BDEA, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 200 mM of BDEA, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(1.8) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of BDEA, about 200 mM of Tris, greater than or about 750 mM of chloride ion, and about 0.2 mM to about 10 mM of KOLLIPHOR P-407, PLURONIC P423, or PEG(IS) tridecyl ether. In embodiments, the compositions comprise about 200 mM of BDEA, about 200 mM of Tris, greater than or about 750 mM of chloride ion, and about 0.2 mM of KOLLIPHOR P-407, PLURONIC P-123, or PEG(18) tridecyl ether. In embodiments, the compositions comprise about 200 mM of BDEA, about 200 mM of Tris, greater than or about 750 mM chloride ion, and about 1.0 nM of KOLLIPHOR P-407, PLURONIC P-123, or PEG(18) tridecyl ether. In embodiments, the compositions comprise about 200 mM of BDEA, about 200 mM of iris, greater than or about 750 mM of chloride ion, and about 5 mM of KOLLIPHOR P-407, PLURONIC P-123, or PEG(18) tridecyl ether. In embodiments, the compositions comprise about 200 mM of BDEA, about 200 mM of Tris, greater than or about 750 mM of chloride ion, and about 10 mM of KOLLIPHOR P-407, PLURONIC P123, or PEG(18) tridecyl ether. In embodiments, the compositions comprise about 200 mM of BDEA, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of BDEA, about 200 mM of Tris, greater than or about 750 mM of chloride ion, and about 0.2 mM to about 10 mM of PEG(18) tridecyl ether. In embodiments, the compositions comprise about 200 mM of BDEA, about 200 mM of Tris, greater than or about 750 mM of chloride ion, and about 0.2 mM of PEG(18) tridecyl ether. In embodiments, the compositions comprise about 200 mM of BDEA, about 200 mM of Tris, greater than or about 750 mM chloride ion, and about 1.0 mM of PEG(18) tridecyl ether. In embodiments, the compositions comprise about 200 mM of BDEA, about 200 mM of Tris, greater than or about 750 mM of chloride ion, and about 5 mM of PEG(18) tridecyl ether. In embodiments, the compositions comprise about 200 mM of BDEA, about 200 mM of Tris, greater than or about 750 mM of chloride ion, and about 10 mM of PEG(18) tridecyl ether. In embodiments, the compositions comprise about 200 mM of BDEA, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of BDEA, about 200 mM of Tris, and about 500 mM to about 1500 mM of chloride ion. In embodiments, the compositions comprise about 300 mM of BDEA, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 300 mM of BDEA, about 200 mM of Tris, greater than or about 750 mM of chloride ion, and about 0.2 mM to about 10 mM of TRITON X-100. In embodiments, the compositions comprise about 300 mM of BDEA, about 200 mM of Tris, greater than or about 750 mM of chloride ion, and about 0.2 mM of TRITON X-100. In embodiments, the compositions comprise about 300 mM of BDEA, about 200 mM of Tris, greater than or about 750 mM chloride ion, and about 1.0 mM of TRITON X-100. In embodiments, the compositions comprise about 300 mM of BDEA, about 200 mM of Tris, greater than or about 750 mM of chloride ion, and about 5 mM of TRITON X-100. In embodiments, the compositions comprise about 300 mM of BDEA, about 200 mM of Tris, greater than or about 750 mM of chloride ion, and about 10 mM of TRITON X-100. In embodiments, the compositions comprise about 300 mM of BDEA, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of BDEA, about 200 mM of Tris, greater than or about 750 mM of chloride ion, and about 0.2 mM to about 10 mM of a non-phenol-containing non-ionic surfactant. In embodiments, the compositions comprise about 300 mM of BDEA, about 200 mM of Tris, greater than or about 750 mM of chloride ion, and about 0.2 mM of a non-phenol-containing non-ionic surfactant. In embodiments, the compositions comprise about 300 mM of BDEA, about 200 mM of Tris, greater than or about 750 mM chloride ion, and about 1.0 mM of a non-phenol-containing non-ionic surfactant. In embodiments, the compositions comprise about 300 mM of BDEA, about 200 mM of Tris, greater than or about 750 mM of chloride ion, and about 5 mM of a non-phenol-containing non-ionic surfactant. In embodiments, the compositions comprise about 300 mM of BDEA, about 200 mM of Tris, greater than or about 750 mM of chloride ion, and about 10 mM of a non-phenol-containing non-ionic surfactant. In embodiments, the compositions comprise about 300 mM of BDEA, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of BDEA, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 300 mM of BDEA, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 300 mM of BDEA, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 300 mM of BDEA, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 300 nM of BDEA, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 300 mM of BDEA, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of BDEA, about 200 mM of Tris, greater than or about 750 mM of chloride ion, and about 0.2 mM to about 10 mM of KOLLIPHOR P-407, PLURONIC P-123, or PEG(18) tridecyl ether. In embodiments, the compositions comprise about 300 mM of BDEA, about 200 mM of Tris, greater than or about 750 nM of chloride ion, and about 0.2 mM of KOLLIPHOR P-407, PLURONIC P-123, or PEG(18) tridecyl ether. In embodiments, the compositions comprise about 300 mM of BDEA, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 300 mM of BDEA, about 200 mM of Tris, greater than or about 750 mM of chloride ion, and about 5 mM of KOLLIPHOR P-407, PLURONIC P-123, or PEG(18) tridecyl ether. In embodiments, the compositions comprise about 300 mM of BDEA, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 300 mM of BDEA, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of BDEA, about 200 mM of Tris, greater than or about 750 mM of chloride ion, and about 0.2 mM to about 10 mM of PEG(18) tridecyl ether. In embodiments, the compositions comprise about 300 mM of BDEA, about 200 mM, of Tris, greater than or about 750 mM of chloride ion, and about 0.2 mM of PEG(18) tridecyl ether. In embodiments, the compositions comprise about 300 mM of BDEA, about 200 mM of Tris, greater than or about 750 mM chloride ion, and about 1.0 mM of PEG(18) tridecyl ether. In embodiments, the compositions comprise about 300 mM of BDEA, about 200 mM of Tris, greater than or about 750 mM of chloride ion, and about 5 mM of PEG(18) tridecyl ether. In embodiments, the compositions comprise about 300 mM of BDEA, about 200 mM of Tris, greater than or about 750 mM of chloride ion, and about 10 mM of PEG(18) tridecyl ether. In embodiments, the compositions comprise about 300 mM of BDEA, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions described herein comprise about 75 mM to about 300 mM of DBAE, about 200 mM of Tris, and greater than or about 750 mM of chloride ion. In embodiments, the compositions comprise about 75 mM of DBAE, about 0 or about 100 mM to about 300 mM of Tris, and greater than or about 750 mM of chloride ion. In embodiments, the compositions comprise about about 75 mM to about 300 mM of DBAE, about 200 mM of Tris, and about 0 or about 500 mM to about 1500 mM chloride ion. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of DBAE, about 200 mM, of Tris, greater than or about 750 mM of chloride ion, and about 0.2 mM of TRITON X-100. In embodiments, the compositions comprise about 75 mM to about 300 mM of DBAE, about 200 mM of Tris, greater than or about 750 mM of chloride ion, and about 1.0 mM of TRITON X-100. In embodiments, the compositions comprise about 75 mM to about 300 mM of DBAE, about 200 mM of Tris, greater than or about 750 mM of chloride ion, and about 5 mM of TRITON X-100. In embodiments, the compositions comprise about 75 mM to about 300 mM of DBAE, about 200 mM of Tris greater than or about 750 mM of chloride ion, and about 10 mM of TRITON X-100. In embodiments, the compositions comprise about 75 mM to about 300 mM of DBAE, about 200 mM of Tris, greater than or about 750 mM of chloride ion, and a concentration of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of DBAE, about 200 mM of Tris, greater than or about 750 mM of chloride ion, and about 0.2 mM of a non-phenol-containing non-ionic surfactant. In embodiments, the compositions comprise about 75 mM to about 300 mM of DBAE, about 200 mM of Tris, greater than or about 750 mM of chloride ion, and about 1.0 mM of a non-phenol-containing non-ionic surfactant. In embodiments, the compositions comprise about 75 mM to about 300 mM of DBAE, about 200 mM of Tris, greater than or about 750 mM of chloride ion, and about 5 mM of a non-phenol-containing non-ionic surfactant. In embodiments, the compositions comprise about 75 mM to about 300 mM of DBAE, about 200 mM of Tris, greater than or about 750 mM of chloride ion, and about 10 mM of a non-phenol-containing non-ionic surfactant. In embodiments, the compositions comprise about 75 mM to about 300 mM of DBAE, about 200 mM of Tris, greater than or about 750 mM of chloride ion, and a concentration of a non-phenol-containing non-ionic surfactant greater than its cmc.

In embodiments, the compositions comprise about 75 mM to about 300 mM of DBAE, about 200 mM of Tris, greater than or about 750 mM of chloride ion, and about 0.2 mM of KOLLIPHOR P-407, PLURONIC P-123, PLURONIC L-121, PLURONIC 31R1, THROW 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM to about 300 mM of DBAE, about 200 mM of Tris, greater than or about 750 mM of chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM to about 300 mM of DBAE, about 200 mM of Tris, greater than or about 750 mM of chloride ion, and about 5.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEWS) tridecyl ether, BRIJ L4, BRIJ 58 or TWEEN 20. In embodiments, the compositions comprise about 75 mM to about 300 mM of DBAE, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM to about 300 mM of DBAE, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of DBAE, about 200 mM of Tris, greater than or about 750 mM of chloride ion, and about 0.2 mkt of KOLLIPHOR P-407, PLURONIC P-123, or PEG(18) tridecyl ether. In embodiments, the compositions comprise about 75 mM to about 300 mM of DBAE, about 200 mM of Tris, greater than or about 750 mM of chloride ion, and about 1.0 mM of KOLLIPHOR P-407, PLURONIC P-123, or PEG(18) tridecyl ether. In embodiments, the compositions comprise about 75 mM to about 300 mM of DBAE, about 200 mM of Tris greater than or about 750 mM of chloride ion, and about 5.0 mM of KOLLIPHOR P-407, PLURONIC P-123, or PEG(18) tridecyl ether. In embodiments, the compositions comprise about 75 mM to about 300 mM of DBAE, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 75 mM to about 300 mM of DBAE, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM to about 300 mM of DBAE, about 200 mM of Tris, greater than or about 750 mM of chloride ion, and about 0.2 mM of PEG(18) tridecyl ether. In embodiments, the compositions comprise about 75 mM to about 300 mM of DBAE, about 200 mM of Tris, greater than or about 750 mM of chloride ion, and about 1.0 mM of PEWS) tridecyl ether. In embodiments, the compositions comprise about 75 mM to about 300 mM of DBAE, about 200 mM of Tris, greater than or about 750 mM of chloride ion, and about 5 mM of PEG(18) tridecyl ether. In embodiments, the compositions comprise about 75 mM to about 300 mM of DBAE, about 200 mM of Tris, greater than or about 750 mM of chloride ion, and about 10 mM of PEG(18) tridecyl ether. In embodiments, the compositions comprise about 75 mM to about 300 mM of DBAE, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of DBAE, about 200 mM of Tris, and about 500 mM to about 1500 mM of chloride ion. In embodiments, the compositions comprise about 75 mM of DBAE, about 200 mM of Tris, about greater than or about 750 mM of chloride ion. In embodiments, the pH of the composition is about 7.0 to about 8.0, In embodiments, the pH of the composition is about 7.5. In embodiments, the pH of the composition is about 7.8.

In embodiments, the compositions comprise about 75 mM of DBAE, about 200 mM of Tris, greater than or about 750 mM of chloride ion, and about 0.2 mM to about 10 mM, of TRITON X-100. In embodiments, the compositions comprise about 75 mM of DBAE, about 200 mM of Tris, greater than or about 750 mM of chloride ion, and about 0.2 mM of TRITON X-100. In embodiments, the compositions comprise about 75 mM of DBAE, about 200 mM of Tris, greater than or about 750 mM chloride ion, and about 1.0 mM of TRITON X-100, In embodiments, the compositions comprise about 75 mM of DBAE, about 200 mM of Tris, greater than or about 750 mM of chloride ion, and about 5 mM of TRITON X-100. In embodiments, the compositions comprise about 75 mM of DBAE, about 200 mM of Tris, greater than or about 750 mM of chloride ion, and about 10 mM of TRITON X-100. In embodiments, the compositions comprise about 75 mM of DBAE, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of DBAE, about 200 mM of Tris, greater than or about 750 mM of chloride ion, and about 0.2 mM to about 10 mM of a non-phenol-containing non-ionic surfactant. In embodiments, the compositions comprise about 75 mM of DBAE, about 200 mM of Tris, greater than or about 750 mM of chloride ion, and about 0.2 mM of a non-phenol-containing non-ionic surfactant. In embodiments, the compositions comprise about 75 mM of DBAE, about 200 mM of Tris, greater than or about 750 mM chloride ion, and about 1.0 mM of a non-phenol-containing non-ionic surfactant. In embodiments, the compositions comprise about 75 mM of DBAE, about 200 mM of Tris, greater than or about 750 mM of chloride ion, and about 5 mM of a non-phenol-containing non-ionic surfactant. In embodiments, the compositions comprise about 75 mM of DBAE, about 200 mM of Tris, greater than or about 750 mM of chloride ion, and about 10 mM of a non-phenol-containing non-ionic surfactant. In embodiments, the compositions comprise about 75 mM of DBAE, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of DBAE, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 trill of DBAE, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ IA, BRIJ 58 or TWEEN 20. In embodiments, the compositions comprise about 75 mM of DBAE, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20, In embodiments, the compositions comprise about 75 mM of DBAE, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 75 mM of DBAE, about 200 mM of Tris, greater than or about 750 nM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20, In embodiments, the compositions comprise about 75 mM of DBAE, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20 greater than its cmc. In embodiments, the pH of the composition is about 7.0 to about 8.0. In embodiments, the pH of the composition is about 7.5, In embodiments, the pH of the composition is about 7.8.

In embodiments, the compositions comprise about 75 mM of DBAE, about 200 mM of Tris, greater than or about 750 mM of chloride ion, and about 0.2 mM to about 10 mM of KOLLIPHOR P-407, PLURONIC P-123, or PEG(18) tridecyl ether. In embodiments, the compositions comprise about 75 mM of DBAE, about 200 mM of Tris, greater than or about 750 mM of chloride ion, and about 0.2 mM of KOLLIPHOR P-407, PLURONIC P-123, or PEG(I tridecyl ether. In embodiments, the compositions comprise about 75 mM of DBAE, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 75 mM of DBAE, about 200 mM of Tris, greater than or about 750 mM of chloride ion, and about 5 mM of KOLLIPHOR P-407, PLURONIC P-123, or PEG(18) tridecyl ether. In embodiments, the compositions comprise about 75 mM of DBAE, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 75 mM of DBAE, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 75 mM of DBAE, about 200 mM of Tris, greater than or about 750 mM of chloride ion, and about 0.2 mM to about 10 mM of PEG(18) tridecyl ether. In embodiments, the compositions comprise about 75 mM of DBAE, about 200 mM of Tris, greater than or about 750 mM of chloride ion, and about 0.2 mM of PEG(18) tridecyl ether. In embodiments, the compositions comprise about 75 mM of DBAE, about 200 mM of Tris, greater than or about 750 mM chloride ion, and about 1.0 mM of PEG(18) tridecyl ether. In embodiments, the compositions comprise about 75 mM of DBAE, about 200 mM of Tris, greater than or about 750 mM of chloride ion, and about 5 mM of PEG(18) tridecyl ether. In embodiments, the compositions comprise about 75 mM of DBAE, about 200 mM of Tris, greater than or about 750 mM of chloride ion, and about 10 mM of PEG(18) tridecyl ether. In embodiments, the compositions comprise about 75 mM of DBAE, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of DBAE, about 200 mM of Tris, and about 500 mM to about 1500 mM of chloride ion. In embodiments, the compositions comprise about 100 mM of DBAE, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 100 mM of DBAE, about 200 mM of Tris, greater than or about 750 mM of chloride ion, and about 0.2 mM to about 10 mM of TRITON X-100. In embodiments, the compositions comprise about 100 mM of DBAE, about 200 mM of Tris, greater than or about 750 mM of chloride ion, and about 0.2 mM of TRITON X-100. In embodiments, the compositions comprise about 100 mM of DBAE, about 200 mM of Tris, greater than or about 750 mM chloride ion, and about 1.0 mM of TRITON X-100. In embodiments, the compositions comprise about 100 mM of DBAE, about 200 mM of Tris, greater than or about 750 mM of chloride ion, and about 5 mM of TRITON X-100.

In embodiments, the compositions comprise about 100 mM of DBAE, about 200 mM of Tris, greater than or about 750 mM of chloride ion, and about 10 mM of TRITON X-100. In embodiments, the compositions comprise about 100 mM of DBAE, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of DBAE, about 200 mM of Tris, greater than or about 750 mM of chloride ion, and about 0.2 mM to about 10 mM of a non-phenol-containing non-ionic surfactant. In embodiments, the compositions comprise about 100 mM of DBAE, about 200 mM of Tris, greater than or about 750 mM of chloride ion, and about 0.2 mM of a non-phenol-containing non-ionic surfactant. In embodiments, the compositions comprise about 100 mM of DBAE, about 200 mM of Tris, greater than or about 750 mM chloride ion, and about 1.0 mM of a non-phenol-containing non-ionic surfactant. In embodiments, the compositions comprise about 100 mM of DBAE, about 200 mM of Tris, greater than or about 750 mM of chloride ion, and about 5 mM of a non-phenol-containing non-ionic surfactant. In embodiments, the compositions comprise about 100 mM of DBAE, about 200 mM of Tris, greater than or about 750 mM of chloride ion, and about 10 mM of a non-phenol-containing non-ionic surfactant. In embodiments, the compositions comprise about 100 mM of DBAE, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of DBAE, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 100 mM of DBAE, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 100 mM of DBAE, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20, in embodiments, the compositions comprise about 100 mM of DBAE, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 100 mM of DBAE, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20, in embodiments, the compositions comprise about 100 mM of DBAE, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of DBAE, about 200 mM of Tris, greater than or about 750 mM of chloride ion, and about 0.2 mM to about 10 mM of KOLLIPHOR P-407, PLURONIC P-123, or PEG(18) tridecyl ether. In embodiments, the compositions comprise about 100 mM of DBAE, about 200 mM of Tris, greater than or about 750 mM of chloride ion, and about 0.2 mM of KOLLIPHOR P-407, PLURONIC P-123, or PEG(18) tridecyl ether. In embodiments, the compositions comprise about 100 mM of DBAE, about 200 mM of Tris, greater than or about 750 mM chloride ion, and about 1.0 mM of KOLLIPHOR P-407, PLURONIC P-123, or PEG(18) tridecyl ether. In embodiments, the compositions compose about 100 mM of DBAE, about 200 mM of Tris, greater than or about 750 mM of chloride ion, and about 5 mM of KOLLIPHOR P-407, PLURONIC P-123, or PEG(18) tridecyl ether. In embodiments, the compositions comprise about 100 mM of DBAE, about 200 mM of Tris, greater than or about 750 mM of chloride ion, and about 10 mM of KOLLIPHOR P-407, PLURONIC P-123, or PEWS) tridecyl ether. In embodiments, the compositions comprise about 100 mM of DBAE, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 100 mM of DBAE, about 200 mM of Tris, greater than or about 750 mM of chloride ion, and about 0.2 mM to about 10 mM of PEG(18) tridecyl ether. In embodiments, the compositions comprise about 100 mM of DBAE, about 200 mM of Tris, greater than or about 750 mM of chloride ion, and about 0.2 mM of PEG(18) tridecyl ether. In embodiments, the compositions comprise about 100 mM of DBAE, about 200 mM of Tris, greater than or about 750 mM chloride ion, and about 1.0 mM of PEG(18) tridecyl ether. In embodiments, the compositions comprise about 100 mM of DBAE, about 200 mM of Tris, greater than or about 750 mM of chloride ion, and about 5 mM of PEG(18) tridecyl ether. In embodiments, the compositions comprise about 100 mM of DBAE, about 200 mM of Tris, greater than or about 750 mM of chloride ion, and about 10 mM of PEG(18) tridecyl ether. In embodiments, the compositions comprise about 100 mM of DBAE, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of DBAE, about 200 mM of Tris, and about 500 mM to about 1500 mM of chloride ion. In embodiments, the compositions comprise about 150 mM of DBAE, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 150 mM of DBAE, about 200 mM of Tris, greater than or about 750 mM of chloride ion, and about 0.2 mM to about 10 mM of TRITON X-100. In embodiments, the compositions comprise about 150 mM of DBAE, about 200 mM of Tris, greater than or about 750 mM of chloride ion, and about 0.2 mM of TRITON X-100. In embodiments, the compositions comprise about 150 mM of DBAE, about 200 mM of Tris, greater than or about 750 mM chloride ion, and about 1.0 mM of TRITON X-100. In embodiments, the compositions comprise about 150 mM of DBAE, about 200 mM of Tris, greater than or about 750 mM of chloride ion, and about 5 mM of TRITON X-100, In embodiments, the compositions comprise about 150 mM of DBAE, about 200 mM of Tris, greater than or about 750 mM of chloride ion, and about 10 mM of TRITON X-100. In embodiments, the compositions comprise about 150 mM of DBAE, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of DBAE, about 200 mM of Tris, greater than or about 750 mM of chloride ion, and about 0.2 mM to about 10 mM of a non-phenol-containing non-ionic surfactant. In embodiments, the compositions comprise about 150 mM of DBAE, about 200 mM of Tris, greater than or about 750 mM of chloride ion, and about 0.2 mM of a non-phenol-containing non-ionic surfactant. In embodiments, the compositions comprise about 150 mM of DBAE, about 200 mM of Tris, greater than or about 750 mM chloride ion, and about 1.0 mM of a non-phenol-containing non-ionic surfactant. In embodiments, the compositions comprise about 150 mM of DBAE, about 200 mM of Tris, greater than or about 750 mM of chloride ion, and about 5 mM of a non-phenol-containing non-ionic surfactant. In embodiments, the compositions comprise about 150 mM of DBAE, about 200 mM of Tris, greater than or about 750 mM of chloride ion, and about 10 mM of a non-phenol-containing non-ionic surfactant. In embodiments, the compositions comprise about 150 mM of DBAE, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of DBAE, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 150 mM of DBAE, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 150 mM of DBAE, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 150 mM of DBAE, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 150 mM of DBAE, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 150 mM of DBAE, about 200 mM of Tris, greater than or about 750 nM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 150 mM of DBAE, about 200 mM of Tris, greater than or about 750 mM of chloride ion, and about 0.2 mM to about 10 mM of KOLLIPHOR P-407, PLURONIC P-123, or PEG(18) tridecyl ether. In embodiments, the compositions comprise about 150 mM of DBAE, about 200 mM of iris, greater than or about 750 mM of chloride ion, and about 0.2 mM of KOLLIPHOR P-407, PLURONIC P-123, or PEG(18) tridecyl ether. In embodiments, the compositions comprise about 150 nM of DBAE, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 150 mM of DBAE, about 200 mM of iris, greater than or about 750 mM of chloride ion, and about 5 mM of KOLLIPHOR P-407, PLURONIC P-123, or PEG(18) tridecyl ether. In embodiments, the compositions comprise about 150 mM of DBAE, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 150 mM of DBAE, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5, in embodiments, the pH of the composition is about 7.8.

In embodiments, the compositions comprise about 150 mM of DBAE, about 200 mM of Tris, greater than or about 750 mM of chloride ion, and about 0.2 mM to about 10 mM, of PEG(18) tridecyl ether. In embodiments, the compositions comprise about 150 mM of DBAE, about 200 mM of Tris, greater than or about 750 mM of chloride ion, and about 0.2 mM of PEG(18) tridecyl ether. In embodiments, the compositions comprise about 150 mM of DBAE, about 200 mM of Tris, greater than or about 750 mM chloride ion, and about 1.0 mM of PEG(18) tridecyl ether, in embodiments, the compositions comprise about 150 mM of DBAE, about 200 mM of Tris, greater than or about 750 mM of chloride ion, and about 5 mM of PEG(18) tridecyl ether. In embodiments, the compositions comprise about 150 mM of DBAE, about 200 mM of Tris, greater than or about 750 mM of chloride ion, and about 10 mM of PEG(18) tridecyl ether. In embodiments, the compositions comprise about 150 mM of DBAE, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of DBAE, about 200 mM of Tris, and about 500 mM to about 1500 mM of chloride ion. In embodiments, the compositions comprise about 200 mM of DBAE, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 200 mM of DBAE, about 200 mM of Tris, greater than or about 750 mM of chloride ion, and about 0.2 mM to about 10 mM, of TRITON X-100. In embodiments, the compositions comprise about 200 mM of DBAE, about 200 mM of Tris, greater than or about 750 mM of chloride ion, and about 0.2 mM of TRITON X-100. In embodiments, the compositions comprise about 200 mM of DBAE, about 200 mM of Tris, greater than or about 750 mM chloride ion, and about 1.0 mM of TRITON X-100. In embodiments, the compositions comprise about 200 mM of DBAE, about 200 mM of Tris, greater than or about 750 mM of chloride ion, and about 5 mM of TRITON X-100. In embodiments, the compositions comprise about 200 mM of DBAE, about 200 mM of Tris, greater than or about 750 mM of chloride ion, and about 10 mM of TRITON X-100. In embodiments, the compositions comprise about 200 mM of DBAE, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of DBAE, about 200 mM of Tris, greater than or about 750 mM of chloride ion, and about 0.2 mM to about 10 mM of a non-phenol-containing non-ionic surfactant. In embodiments, the compositions comprise about 200 mM of DBAE, about 200 mM of Tris, greater than or about 750 mM of chloride ion, and about 0.2 mM of a non-phenol-containing non-ionic surfactant. In embodiments, the compositions comprise about 200 mM of DBAE, about 200 mM of Tris, greater than or about 750 mM chloride ion, and about 1.0 mM of a non-phenol-containing non-ionic surfactant. In embodiments, the compositions comprise about 200 mM of DBAE, about 200 mM of Tris, greater than or about 750 mM of chloride ion, and about 5 mM of a non-phenol-containing non-ionic surfactant. In embodiments, the compositions comprise about 200 mM of DBAE, about 200 mM of Tris, greater than or about 750 mM of chloride ion, and about 10 mM of a non-phenol-containing non-ionic surfactant. In embodiments, the compositions comprise about 200 mM of DBAE, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of DBAE, about 200 mM of Tris, greater than or about 750 mM of chloride ion, and about 0.2 mM to about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of DBAE, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of DBAE, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of DBAE, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of DBAE, about 200 mM of Tris, greater than or about 750 mM of chloride ion, and about 10 mM of KOLLIPHOR P-407, PLURONIC P-123. PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 200 mM of DBAE, about 200 mM of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of DBAE, about 200 mM of Tris, greater than or about 750 mM of chloride ion, and about 0.2 mM to about 10 mM of KOLLIPHOR P-407, PLURONIC P423, or PEG(18) tridecyl ether. In embodiments, the compositions comprise about 200 mM of DBAE, about 200 mM of Tris, greater than or about 750 mM of chloride ion, and about 0.2 mM of KOLLIPHOR P-407, PLURONIC P-123, or PEG(18) tridecyl ether. In embodiments, the compositions comprise about 200 mM of DBAE, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 200 mM of DBAE, about 200 mM of Tris, greater than or about 750 mM of chloride ion, and about 5 mM of KOLLIPHOR P-407, PLURONIC P-123, or PEG(18) tridecyl ether. In embodiments, the compositions comprise about 200 mM of DBAE, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 200 mM of DBAE, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 200 mM of DBAE, about 200 mM of Tris, greater than or about 750 mM of chloride ion, and about 0.2 mM to about 10 mM of PEG(18) tridecyl ether. In embodiments, the compositions comprise about 200 mM of DBAE, about 200 mM of Tris, greater than or about 750 mM of chloride ion, and about 0.2 mM of PEG(18) tridecyl ether. In embodiments, the compositions comprise about 200 mM of DBAE, about 200 mM of Tris, greater than or about 750 mM chloride ion, and about 1.0 mM of PEG(18) tridecyl ether. In embodiments, the compositions comprise about 200 mM of DBAE, about 200 mM of Tris, greater than or about 750 mM chloride ion, and about 5 mM of PEG(18) tridecyl ether. In embodiments, the compositions comprise about 200 mM of DBAE, about 200 mM of Tris, greater than or about 750 mM of chloride ion, and about 10 mM of PEG(18) tridecyl ether. In embodiments, the compositions comprise about 200 mM of DBAE, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5, in embodiments, the pH of the composition is about 7.8.

In embodiments, the compositions comprise about 300 mM of DBAE, about 200 mM of Tris, and about 500 mM to about 1500 mM of chloride ion. In embodiments, the compositions comprise about 300 mM of DBAE, about 200 mM of Tris, about greater than or about 750 mM of chloride ion. In embodiments, the pH of the composition is about 7.0 to about 8.0. In embodiments, the pH of the composition is about 7.5. In embodiments, the pH of the composition is about 7.8.

In embodiments, the compositions comprise about 300 mM of DBAE, about 200 mM of Tris, greater than or about 750 mM of chloride ion, and about 0.2 mM to about 10 mM of TRITON X-100. In embodiments, the compositions comprise about 300 mM of DBAE, about 200 mM of Tris, greater than or about 750 mM of chloride ion, and about 0.2 mM of TRITON X-100. In embodiments, the compositions comprise about 300 mM of DBAE, about 200 trial of Tris, greater than or about 750 mM chloride ion, and about 1.0 mM of TRITON X-100. In embodiments, the compositions comprise about 300 mM of DBAE, about 200 mM of Tris, greater than or about 750 mM of chloride ion, and about 5 mM of TRITON X-100. In embodiments, the compositions comprise about 300 mM of DBAE, about 200 mM of Tris, greater than or about 750 mM of chloride ion, and about 10 mM of TRITON X-100. In embodiments, the compositions comprise about 300 ml of DBAE, about 200 mM of Tris, greater than or about 750 mM of chloride ion, and a concentration of of TRITON X-100 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of DBAE, about 200 mM of Tris, greater than or about 750 mM of chloride ion, and about 0.2 mM to about 10 mM of a non-phenol-containing non-ionic surfactant. In embodiments, the compositions comprise about 300 mM of DBAE, about 200 mM of Tris, greater than or about 750 mM of chloride ion, and about 0.2 mM of a non-phenol-containing non-ionic surfactant. In embodiments, the compositions comprise about 300 mM of DBAE, about 200 mM of Tris, greater than or about 750 mM chloride ion, and about 1.0 mM of a non-phenol-containing non-ionic surfactant. In embodiments, the compositions comprise about 300 mM of DBAE, about 200 mM of Tris, greater than or about 750 mM of chloride ion, and about 5 mM of a non-phenol-containing non-ionic surfactant. In embodiments, the compositions comprise about 300 mM of DBAE, about 200 mM of Tris, greater than or about 750 mM of chloride ion, and about 10 mM of a non-phenol-containing non-ionic surfactant. In embodiments, the compositions comprise about 300 mM of DBAE, about 200 mM of Tris, greater than or about 750 mM of chloride ion, and a concentration of a non-phenol-containing non-ionic surfactant greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 nikl of DBAE, about 200 mM of Tris, greater than or about 750 mM of chloride ion, and about 0.2 mM to about 10 mM, of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4. BRIJ 58 or TWEEN 20. In embodiments, the compositions comprise about 300 mM of DBAE, about 200 mM of Tris, greater than or about 750 mM of chloride ion, and about 0.2 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 300 mM of DBAE, about 200 mM of Tris, greater than or about 750 mM chloride ion, and about 1.0 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 300 mM of DBAE, about 200 mM of Tris, greater than or about 750 mM of chloride ion, and about 5 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether, BRIJ L4, BRIJ 58 or TWEEN 20. In embodiments, the compositions comprise about 300 nM of DBAE, about 200 mM of Tris, greater than or about 750 mM of chloride ion, and about 10 mM of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG (18) tridecyl ether, BRIJ L4, BRIJ 58 or TWEEN 20. In embodiments, the compositions comprise about 300 mM of DBAE, about 200 mM, of Tris, greater than or about 750 mM of chloride ion, and a concentration of KOLLIPHOR P-407, PLURONIC P-123, PLURONIC L-121, PLURONIC 31R1, TETRONIC 701, 2,4,7,9-tetramethyl-d-decyne-4,7-diol ethoxylate, PEG(18) tridecyl ether BRIJ L4, BRIJ 58 or TWEEN 20 greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of DBAE, about 200 mM of Tris, greater than or about 750 mM of chloride ion, and about 0.2 mM to about 10 mM, of KOLLIPHOR P-407, PLURONIC P-123, or PEG(18) tridecyl ether. In embodiments, the compositions comprise about 300 mM of DBAE, about 200 nM of Tris, greater than or about 750 nM of chloride ion, and about 0.2 mM of KOLLIPHOR P-407, PLURONIC P-123, or PEG(18) tridecyl ether. In embodiments, the compositions comprise about 300 mM of DBAE, about 200 mM of Tris, greater than or about 750 mM chloride ion, and about 1.0 mM of KOLLIPHOR P-407, PLURONIC P-123, or PEG(18) tridecyl ether. In embodiments, the compositions comprise about 300 mM of DBAE, about 200 mM of Tris, greater than or about 750 mM of chloride ion, and about 5 mM of KOLLIPHOR P-407, PLURONIC P-123, or PEG(18) tridecyl ether. In embodiments, the compositions comprise about 300 nM of DBAE, about 200 mM of Tris, greater than or about 750 mM of chloride ion, and about 10 mM of KOLLIPHOR P-407, PLURONIC P-123, or PEG(18) tridecyl ether. In embodiments, the compositions comprise about 300 mM of DBAE, about 200 mM of Tris, greater than or about 750 mM of chloride ion, and a concentration of KOLLIPHOR P-407, PLURONIC P-123, or PEG(18) tridecyl ether greater than its cmc. In embodiments, the pH of the composition is about 7.0 to about 8.0. In embodiments, the pH of the composition is about 7.5. In embodiments, the pH of the composition is about 7.8.

In embodiments, the compositions comprise about 300 mM of DBAE, about 200 mM of Tris, greater than or about 750 mM of chloride ion, and about 0.2 mM to about 10 mM of PEG(18) tridecyl ether. In embodiments, the compositions comprise about 300 mM of DBAE, about 200 mM of Tris, greater than or about 750 mM of chloride ion, and about 0.2 mM of PEG(18) tridecyl ether. In embodiments, the compositions comprise about 300 mM of DBAE, about 200 mM of Tris, greater than or about 750 mM chloride ion, and about 1.0 mM of PEG(18) tridecyl ether. In embodiments, the compositions comprise about 300 mM of DBAE, about 200 mM of Tris, greater than or about 750 mM of chloride ion, and about 5 mM of PEG(18) tridecyl ether. In embodiments, the compositions comprise about 300 mM of DBAE, about 200 mM of Tris, greater than or about 750 mM of chloride ion, and about 10 trim of PEG(18) tridecyl ether. In embodiments, the compositions comprise about 300 mM of DBAE, about 200 mM of Tris, greater than or about 750 mM of chloride ion, and a concentration of PEG(18) tridecyl ether greater than its cmc. In embodiments, the pH of the composition is about 7.0 to about 8.0. In embodiments, the pH of the composition is about 7.5. In embodiments, the pH of the composition is about 7.8.

6. EXAMPLES

The following examples are illustrative of some of the electrodes, plates, kits and methods falling within the scope of the present disclosure. They are, of course, not to be considered in any way limitative of the disclosure. Numerous changes and modifications can be made with respect to the disclosure by one of ordinary skill in the art without undue experimentation.

Example I

Comparison of ECL Coreactants

ECL read buffers were prepared with three different EC, co-reactants: tripropylamine (TPA), N-butyldiethanolamine (BDEA) and 2-dibutylaminoethanol (DBAE). BDEA and DBAE have low volatility (vapor pressure=0.1 mm Hg and 1 mm Hg), high boiling points (446° C. and 273-275° C.), low flammability, high water solubility and low odor when compared to TPA (vapor pressure=2.9 mm Hg, boiling point=156° C.). The TPA-containing read buffer was MSD Read Buffer T (1×) (Meso Scale Discovery). The BDEA and DBAE read buffers were prepared using the same formulation (125 mM coreactant, 200 trim Tris-HCl, 50 mM KCl, 0.1% (v/v) TRITON X-100, adjusted to pH 7.8 with HCl) except for replacement of TPA with BDEA or DBAE. In addition, two additional read buffers were prepared that were analogous to the TPA and BDEA read buffers described above except for omission of the surfactant (TRITON X-100).

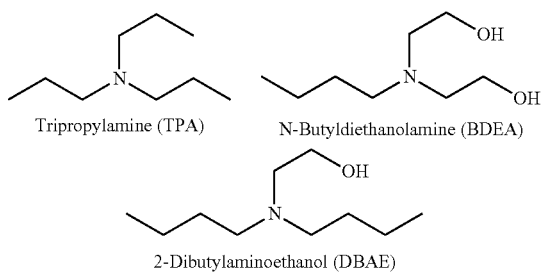

Figure 1A:
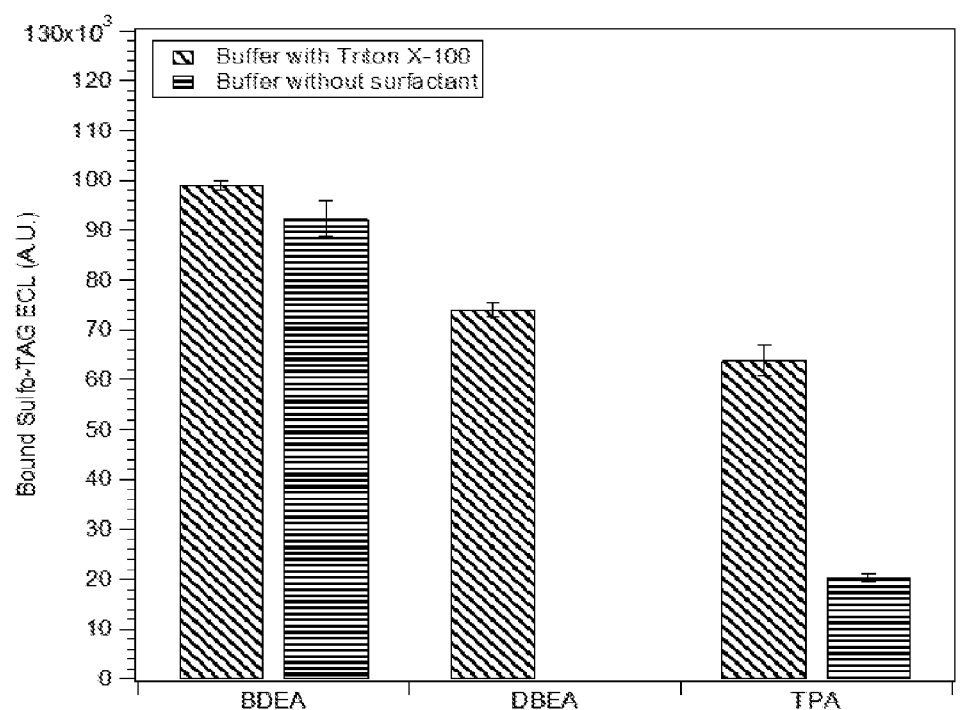
Figure 1B:
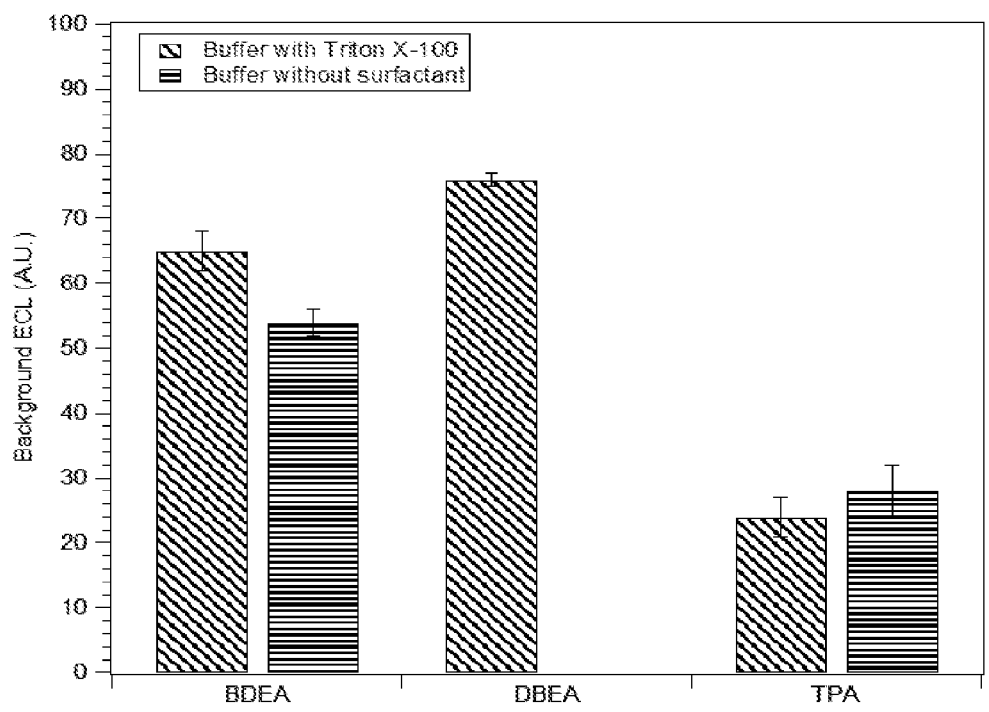

ECL measurements were carried out using MSD MULTI-ARRAY Streptavidin plates (Meso Scale Discovery). Each well of the plates has an integrated carbon ink working electrode on which is supported an immobilized layer of streptavidin. Prior to use, the wells were washed with phosphate buffered saline containing TWEEN 20 (PBST). To measure ECL signal from an ECL label, some wells of the plates were incubated with a solution containing a low concentration bovine IgG that was labeled with both biotin NHS ester (to provide binding to the plate) and SULFO-TAG NHS ester (an ECL label; Meso Scale Discovery). To measure ECL background in the absence of label, some wells were incubated with the same solution except for the omission of the labeled bovine IgG. After incubation at room temperature with shaking to allow for binding of the labeled. IgG to the streptavidin-coated electrodes, the wells were washed with PBST and one of the test read buffers was added. ECL was then measured using an ECL plate reader (MSD SECTOR Imager 6000, Meso Scale Discovery), FIGS. 1A and 1B show that for the surfactant (TRITON X-100)-containing read buffers, BDEA DBAE and TPA all provided similar specific signals in the presence of ECL labels (FIG. 1A) and similar background signals in the absence of ECL labels (FIG. 1B), showing that BDEA and DBAE are potential alternatives to TPA. In keeping with the known benefits of surfactants (and, in particular, aromatic ether-containing surfactants such as TRITON X-100) on ECL in the presence of TPA-containing read buffers, the specific signal for the surfactant-free TPA read buffers was substantially less than for the surfactant-containing TPA read buffer, in comparison, omission of surfactant from the BDEA-containing read buffer had a minimal effect on specific signal.

Figure 1C:
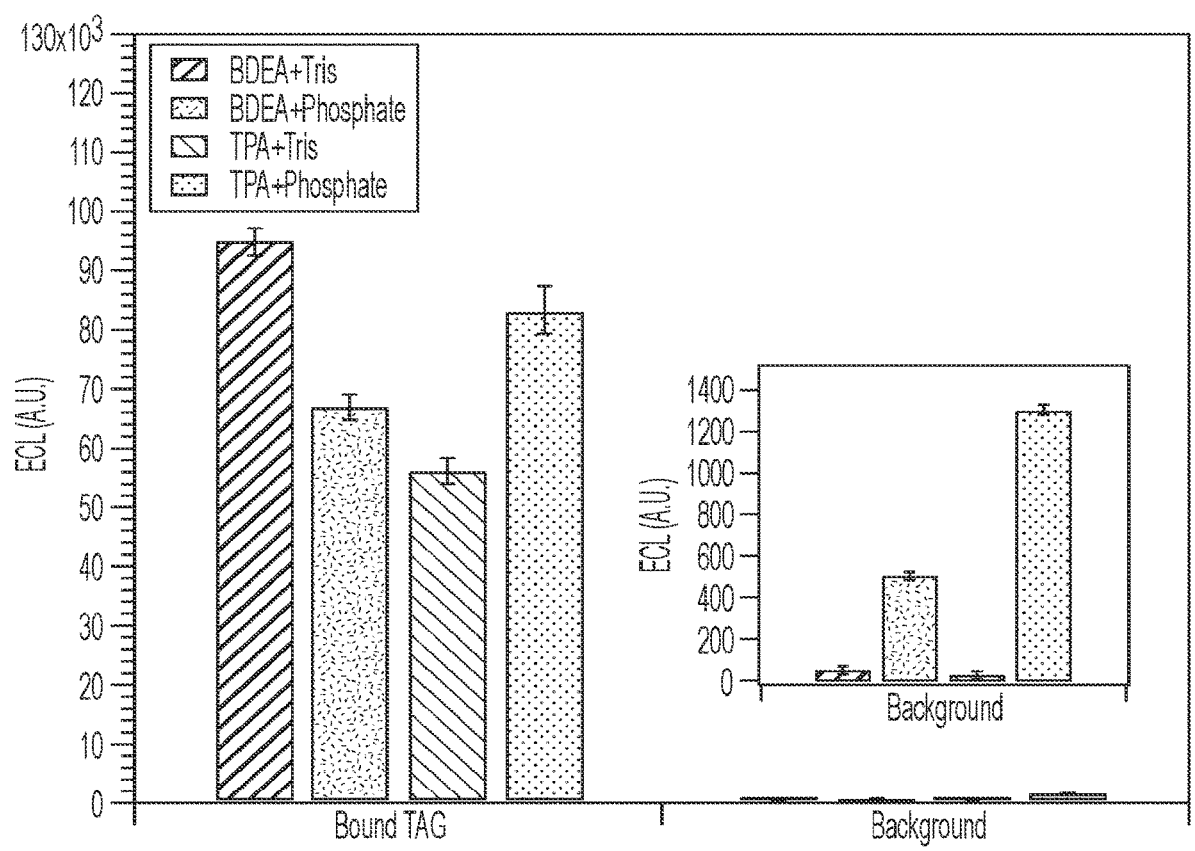

FIG. 1C compares the surfactant-containing BDEA read buffer as described for FIGS. 1A and 1B to an analogous read buffer, except for the replacement of the Tris pH buffering component with phosphate as the buffering component. The figure shows that use of phosphate as the buffering component leads to a decrease in performance due to both a loss of specific signal and an increase in background signal.

Example II

Immunoassays Using BDEA-Based Read Buffers

The performance of BDEA-based read buffers for multiplexed sandwich immunoassays was compared to conventional TPA-based read buffers using the 10 multiplexed assays in the MSD V-PLEX Proinflammatory Panel 1 kit (Meso Scale Discovery). The kit uses MSD MULTI-ARRAY plates in which each well has an integrated screen-printed carbon ink electrode on the bottom and a 10-plex array of capture antibodies against 10 analytes immobilized on the electrode. The assays were run according to the kit instructions except for the use of BDEA-containing ECL read buffers. Briefly, (i) the plates were washed prior to adding sample; (ii) 50 µL of sample (containing calibration standards for each analyte diluted in the kit assay diluent) was added to each well; (iii) the plates were incubated for 120 min. with shaking to allow analyte to bind the capture antibodies and then washed to remove unbound samples; (iv) 25 µL of a mixture of 10 labeled detection antibodies for the 10 analytes (labeled with MSD SULFO-TAG NHS ester) in the kit antibody diluent was added to each well; (v) the plates were incubated for 90 min. with shaking to allow detection antibodies to bind to capture analyte and then washed to remove unbound detection antibody; (vi) 150 µL of ECL read buffer was added and ECL was measured in a MSD SECTOR Imager 6000 plate reader.

FIG. 2A compares the signals measured using TPA and BDEA read buffers with optimized concentrations of each co-reactant: the conventional TPA-containing read buffer specified by the kit (MSD Read Buffer T (2X)) and a BDEA-containing read buffer as described in Example 1. Signals are shown for a "Mid-Cal" sample that contains a concentration of each analyte that falls somewhere in the middle of the quantitation range for that assay, and for a "NSB" sample which is the kit assay diluent without any added analyte. The figure provides the measured ECL signals for each analyte/array element and ECL signals normalized to the signal measured using the TPA read buffer. Each value represents the average of 240 replicates (5 assay plates×48 replicates per plate), in some cases after removal of outliers using the Grossman test using a 99% confidence interval. The figure also provides the average of the intraplate coefficients of variation (CV) measured for each of the 5 plates (Intraplate CV), as well as the coefficient of variation for the average signal in each plate (Interplate CV). The results show that at their optimized concentrations, the TPA and BDEA-based read buffers provide similar signals in the presence of analyte (the normalized signals for the Mid-Cal sample using the BDEA-based read buffer fall between 90% and 140%). Variability (as represented by the CVs) for the BDEA read buffer was on average similar or slightly better than the TPA read buffer. Unexpectedly, the NSB sample signals (representing undesirable non-specific background signals from non-specific binding of detection antibodies to the capture array elements) were very high when using the BDEA buffer (normalized NSB signals on one array element approached 300%).

FIG. 2B shows results from a repeat of the experiment described above for FIG. 2A, except that a further optimized BDEA read buffer was used and only 4 plates were tested per condition. The composition of the read buffer was as described in Example 1, but had a slightly higher BDEA concentration (150 mM) and also included 800 mM NaCl. The addition of the high salt levels had only a minor effect on specific signals measured with the Mid-Cal sample (normalized signals were in the range of about 75% to 125%), but had an unexpected ability to drastically reduce the non-specific binding with the NSB samples (the highest normalized NSB signal was 152%, although most were mostly in the range of about 75% to 125%).

Example III

Robustness of Optimized BDEA Read Buffer

This example shows the results of several experiments comparing the robustness of an optimized BDEA read buffer (as described above for FIG. 2B) and conventional TPA read buffers to different potential sources of environmental and compositional variation. Specific signals were generated using biotin- and SULFO-TAG labeled bovine IgG bound to MSD streptavidin plates (as described in Example 1).

Figure 3A:
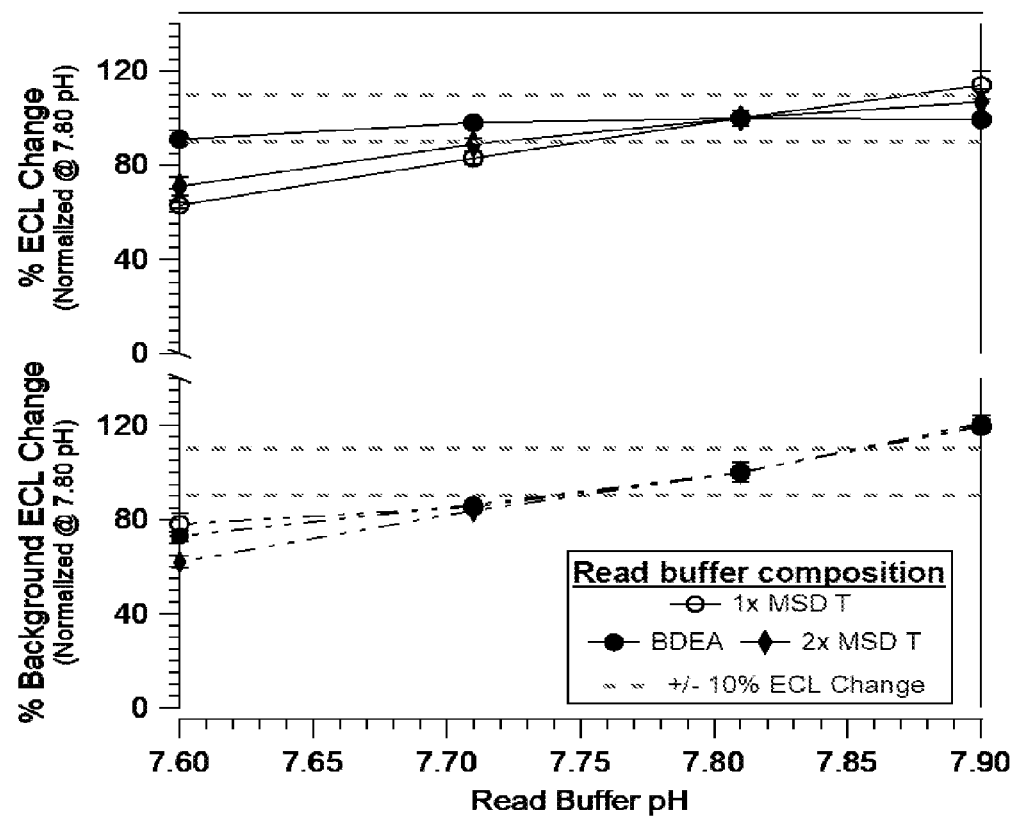

FIG. 3A shows the effect of read buffer pH on specific ECL signals (ECL) from bound labeled IgG and background. ECL (Background ECL) measured in the absence of the labeled IgG. The results are shown as % changes relative to values measured at pH 7.8. The specific ECL signals measured over the range of pH 7.7 to 7.9 were within 5% of the signal measured at pH 7.8 for the BDEA read buffer (filled circle symbol), but not for two conventional TPA-containing read buffers (MSD Read Buffer T (MSD T) 1× and 2×, diamond and open circles, respectively). The slope of the changes in the specific ECL signal over the same pH range was about 7.4% per pH unit for the BDEA read buffer compared to 161% per pH unit for Read Buffer T (1×) and 93% per pH unit for Read Buffer T (2×), demonstrating that the optimized BDEA formulation was much less sensitive to pH variations.

Figure 3B:
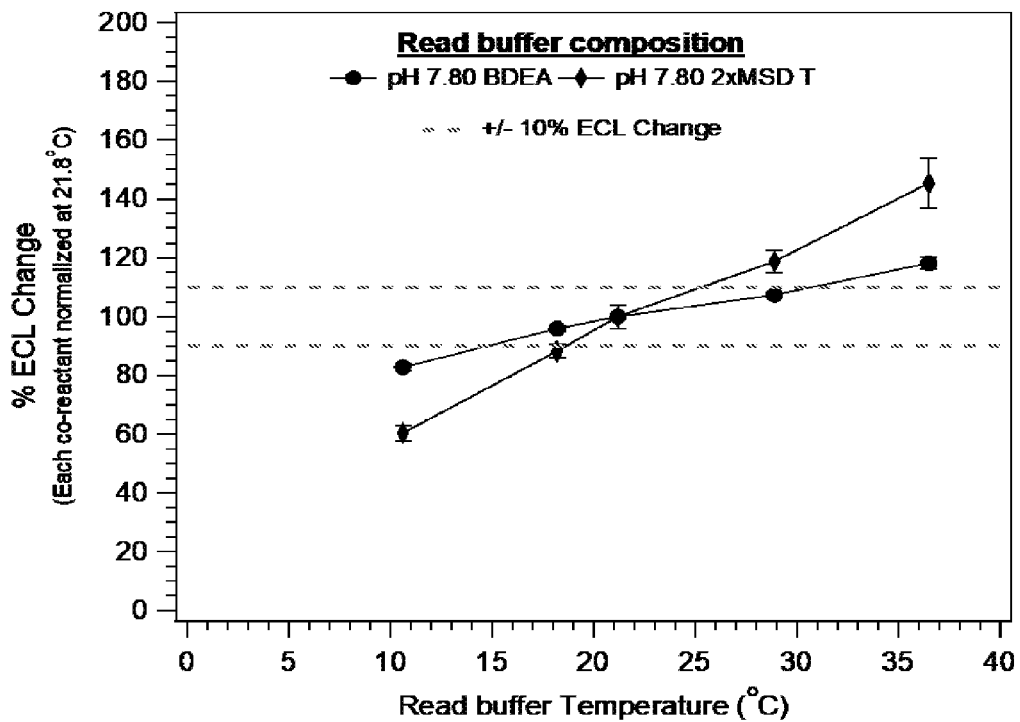

FIG. 3B shows the effect of temperature on ECL generation in the presence of different read buffers. The specific signal from biotin- and SULFO-TAG-labeled IgG streptavidin plates (reported as the % change from the signal at 21.8° C.) stayed within 10% of the 21.8° C. value when temperature was varied between about 18° C. and 30° C. when the optimized BDEA formulation was used as the read buffer, but showed much large changes when a conventional TPA read buffer was used (MSD Read Buffer T (2×)). The slope of the changes in the specific ECL signal over the tested temperature range was about 1.6% per ° C. for the BDEA read buffer compared to 3.9% per ° C. for Read Buffer T (2×), demonstrating that the optimized BDEA formulation was much less sensitive to temperature variations.

Figure 3C:
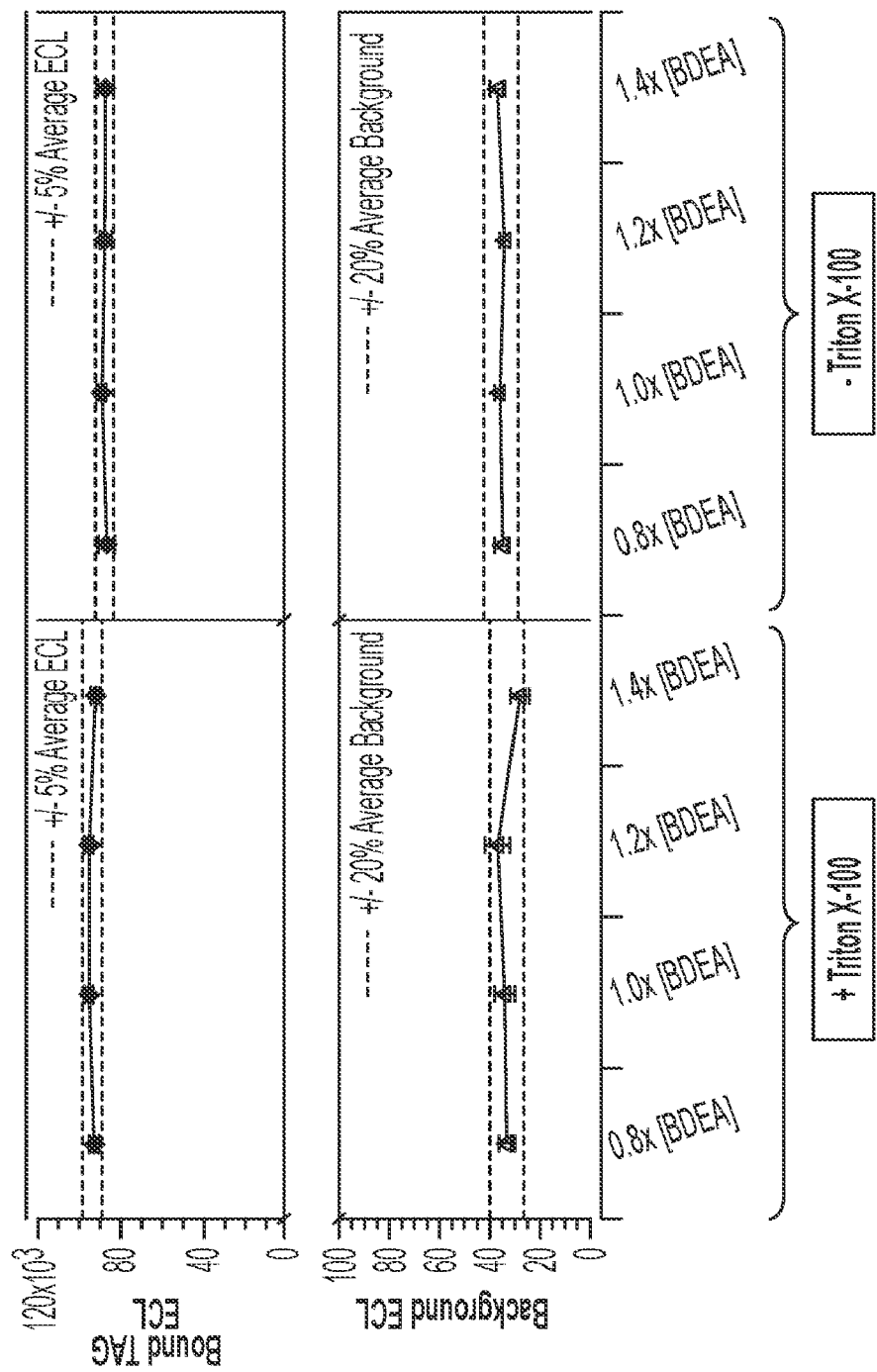
Figure 3D:
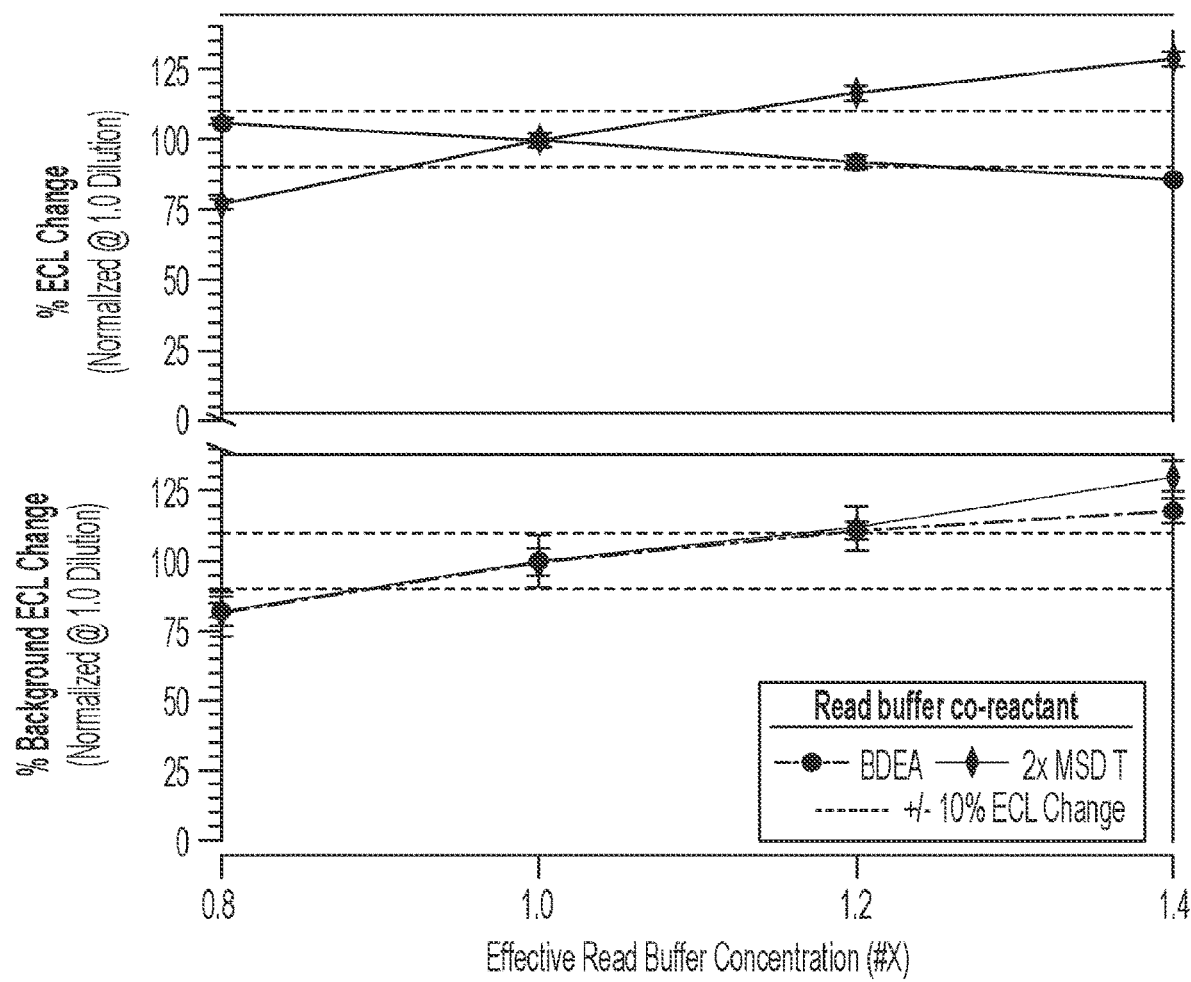

FIG. 3C shows the effect of coreactant concentration on ECL generation in the presence of different read buffers. The concentration of BDEA in the optimized BDEA read buffer formulation was varied from 0.8 times (0.8×, 100 mM) to 1.4 times (1.4×, 175 mM) from the nominal concentration (1×, 125 nM). Over these concentration ranges, there was almost no change in the measured specific ECL signals (which stayed within 5% of the 1× condition). Similar signals and behavior were observed if TRITON X-100 was omitted from the formulation. The result shows that the BDEA read buffer will be relatively insensitive to changes in BDEA concentration resulting from differences in BDEA raw materials or due to manufacturing variability, FIG. 3D shows the effect of diluting or concentrating all the components in the BDEA read buffer. The concentration of all the components in the optimized BDEA read buffer formulation were varied from 0.8 times (0.8×) to 1.4 times (1.4×) the nominal concentrations (1×). Over the range from 0.8× to 1.2×, the specific signal measured with the BDEA formulations stayed within 10% of the 1× condition, while the variation of the specific signal measured with a TPA read buffer (MSD Read Buffer T 2×) was roughly twice as much as that of the BDEA formulations. The result shows that the BDEA read buffer is relatively insensitive to changes in dilution, such as user errors in preparing BDEA read buffer by reconstituting a dry reagent or diluting a liquid concentrate.

Figure 3E:
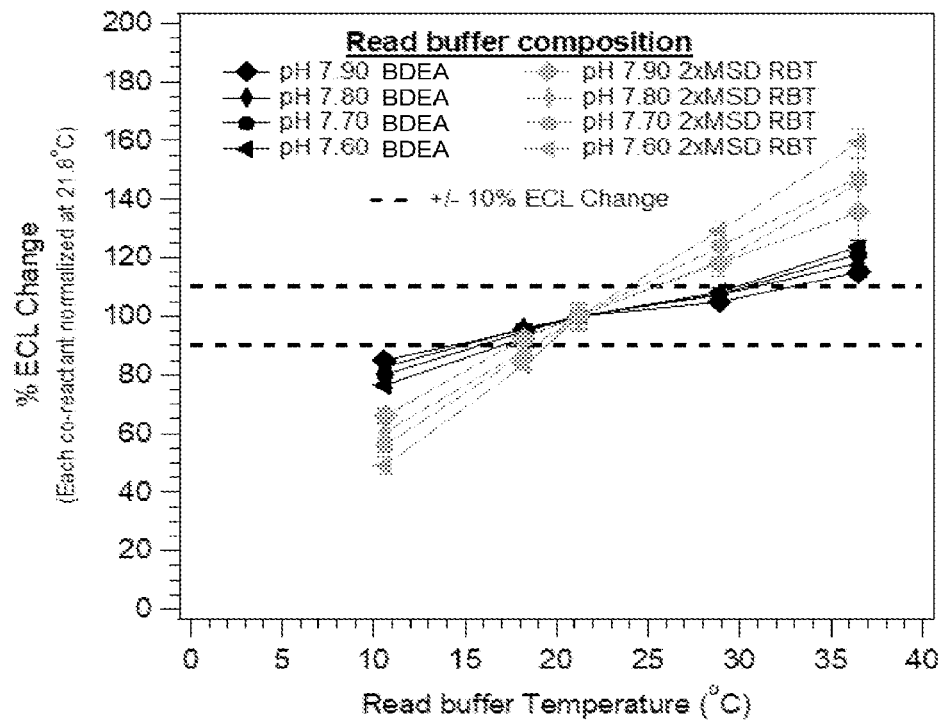
Figure 3F:
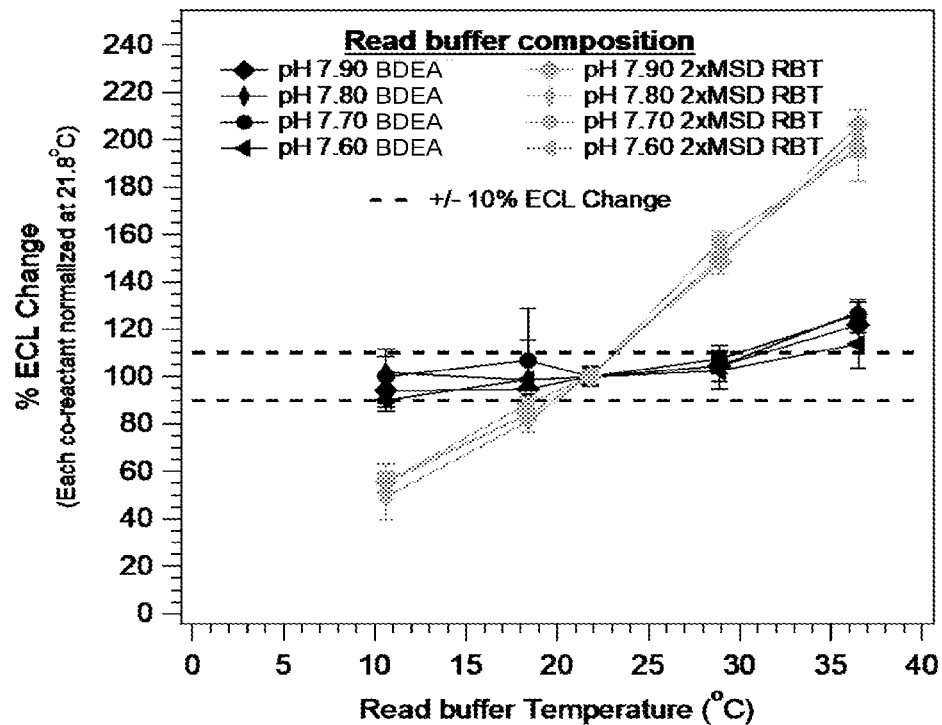

FIG. 3E shows the effect of temperature on TEL generation in the presence of different read buffers (TPA read buffer, MSD Read Buffer T (2×) and BDEA formulation) and at various pH ranging from 7.60 to 7.90. FIG. 3F shows the % background change in ECL signal in the presence of TPA read buffer and BDEA formulation at different temperatures and pH. The slope of the changes in the specific ECL signal over the tested temperature range at pH 7.80 was less than 1% per ° C. for the BDEA read buffer, compared to 6% per ° C. for Read Buffer T (2×), further demonstrating the robustness of the BDEA read buffer at different temperatures.

Figure 4:
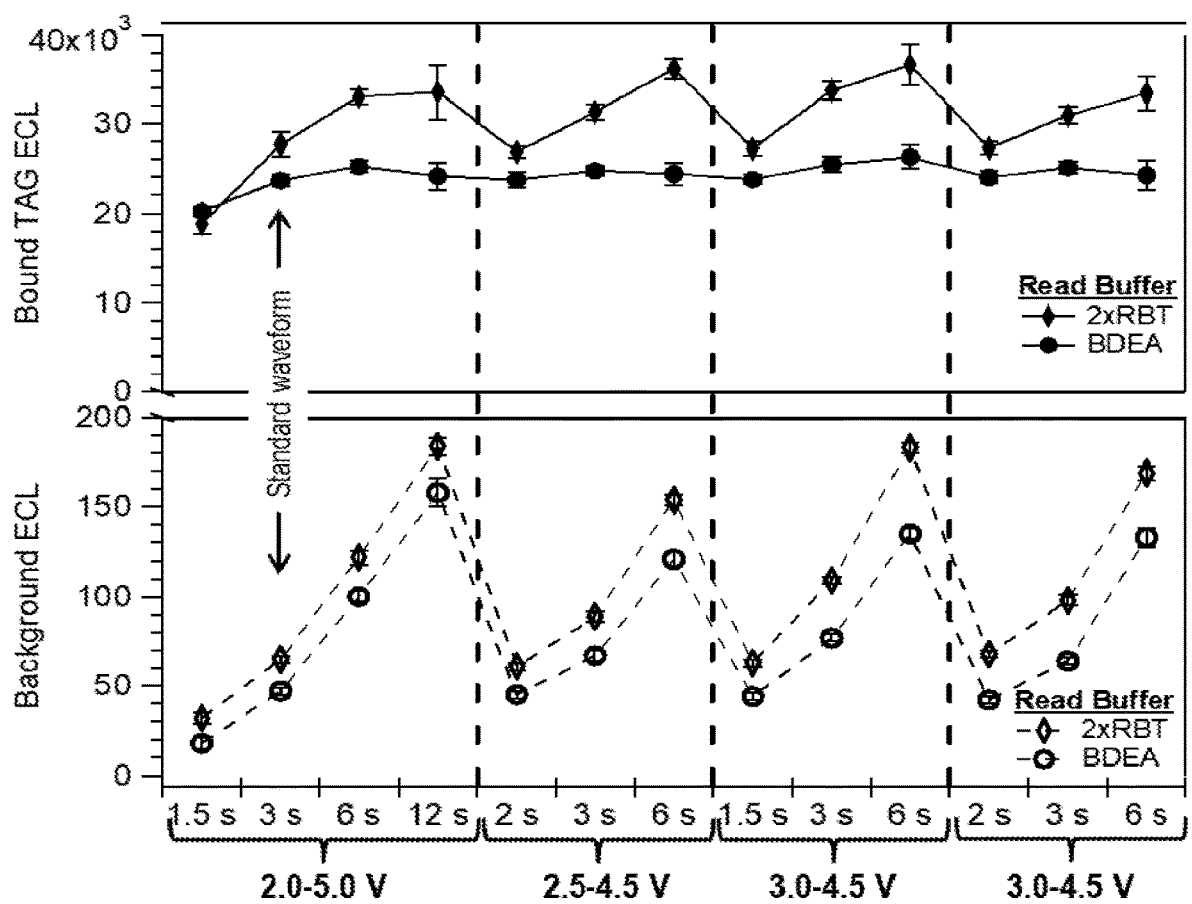
FIG. 4 shows the effect of voltage waveform and duration on the generation of specific ECL signals and ECL background signals generated in the presence of BDEA and TPA containing read buffers.

FIG. 4 shows the effect of different voltage waveforms applied to the streptavidin-coated electrodes in the streptavidin MULTI-ARRAY plates. The plot shows specific signal (ECL) and background signal (Background ECL) for 4 different voltage ramps (2.0 to 5.0V, 2.5 to 4.5V, 3.0 to 4.5V and 3.0 to 5.0V) applied over different durations (between 1.5 and 12 seconds, depending on the ramp voltages). The ramp rate is determined by the ramp voltages and duration; for example, a ramp from 2.0 to 5.0V over 3 seconds duration would have a ramp rate of (5V-2V)/3s=1V/s. The figure shows that for a given ramp, the background ECL increases with duration for both TPA and BDEA-based read buffers. In contrast, the specific ECL increases with duration when a TPA read buffer was used (MSD Read Buffer T 2×), but is relatively independent of duration when the BDEA read buffer is used. The result shows that the BDEA formulation is more tolerant of variations in ECL excitation conditions, and also shows that faster waveforms and measurements are achievable with the BDEA read buffer, without a loss in sensitivity.

Example IV

BDEA Read Buffers with Alternative Surfactants

Figure 5A:
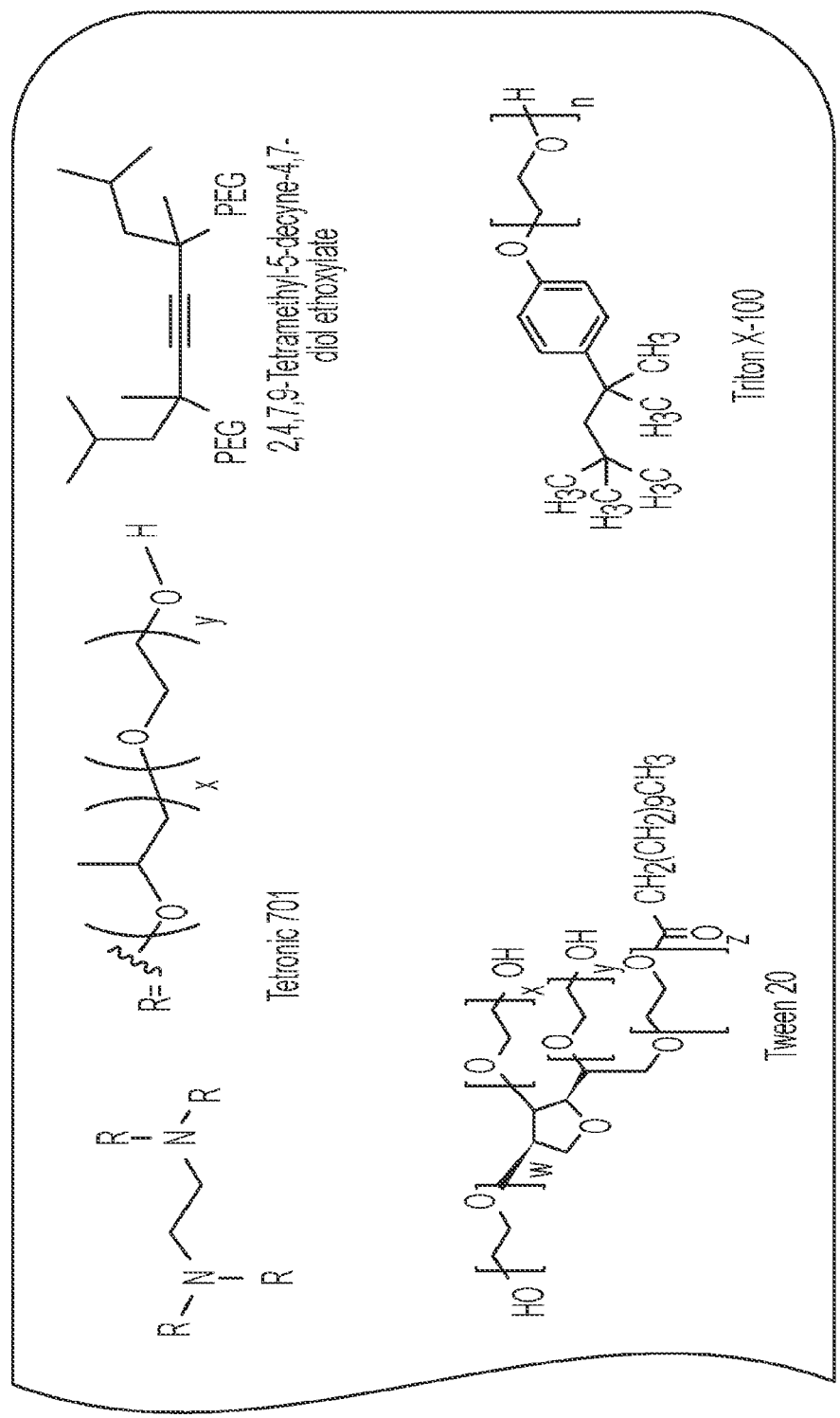
FIG. 5A shows the chemical structures of a set of non-ionic surfactants.

A number of BDEA-containing ECL read buffers were prepared with the composition of the optimized high salt formulation of Example 2, except for the replacement of the 1 mM TRITON X-100 component with a variety of alternative milder surfactants at 0.5 mM (or omission of the surfactant as a control). FIG. 5A shows surfactants that were tested in this experiment. FIG. 5B shows that addition of the surfactants resulted in a significant reduction in the liquid-air surface tension of the read buffers relative to the surfactant-free read buffer (as determined by the shape of pendant droplets). Surface tensions less than 40 dyne/cm provided a consistent meniscal shape for reproducible imaging into wells of a 96-well plate.

Figure 6A:
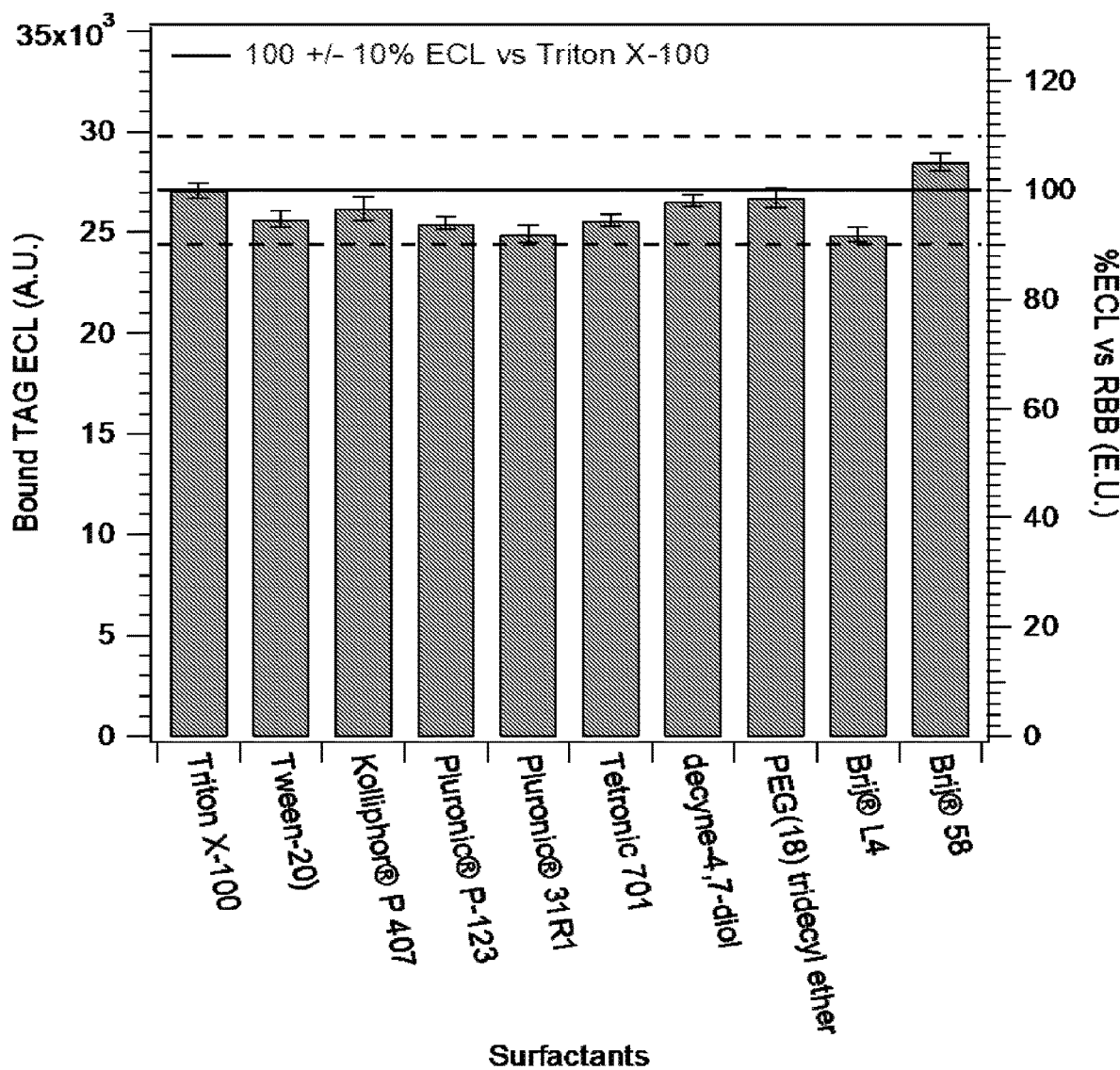
FIG. 6A shows comparison of specific ECL signals.
Figure 6B:
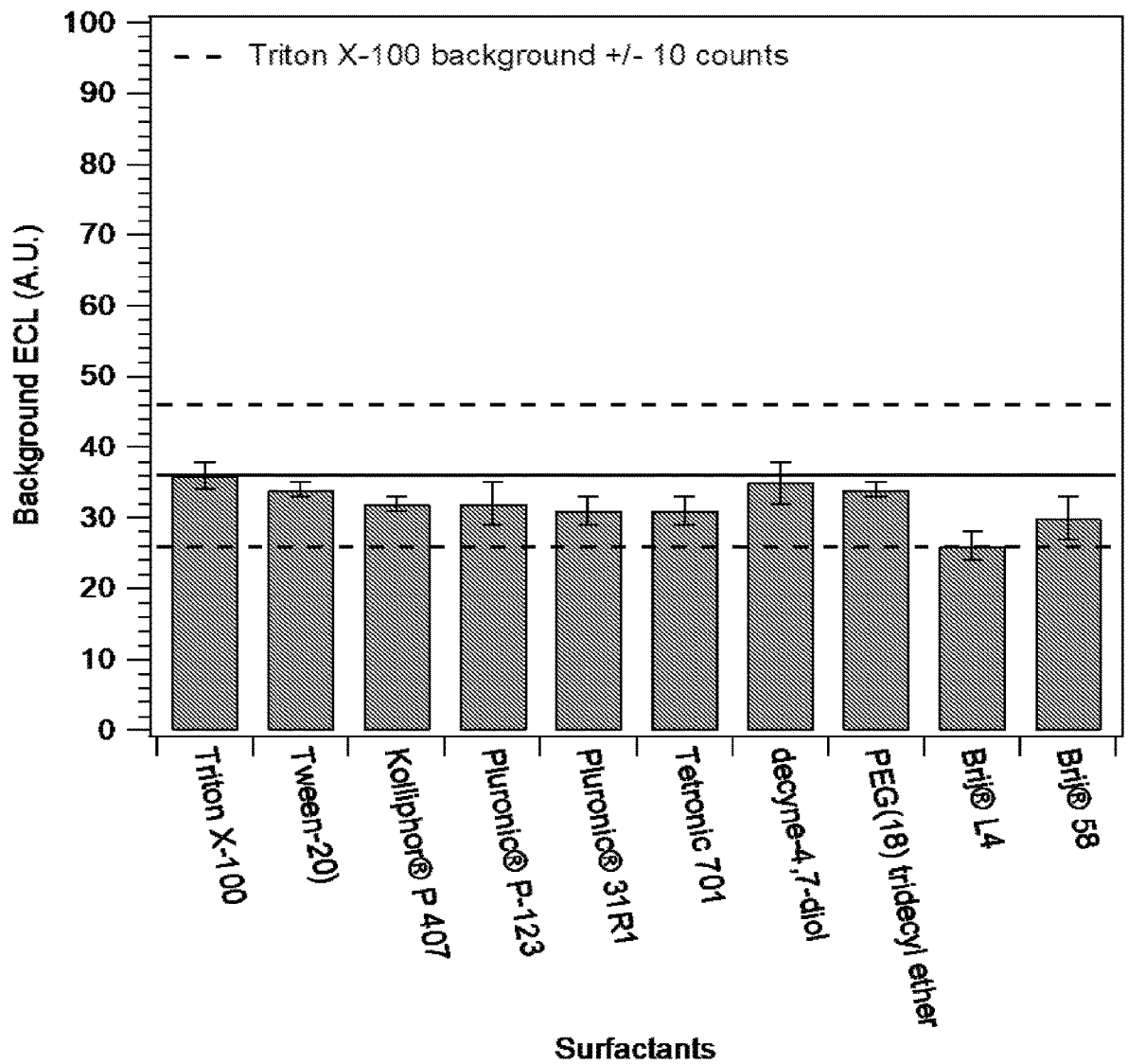
FIG. 6B shows comparison of ECL background signals, generated using read buffers containing BDEA, but having different surfactants.

The efficiency of ECL generation in the different read buffers was measured by measuring specific signals from biotin- and SULFO-TAG labeled bovine IgG bound to MSD streptavidin plates, and background signals measured in the same system in the absence of labeled IgG (as described in Example 1). The specific ECL signals (FIG. 6A) and background ECL signals (FIG. 6B) were remarkably independent of surfactant structure: the specific signals were all within 10%, and the background signals were all within 10 ECL units of the values measured for the read buffer containing TRITON X-100.

The different read buffer formulations were used in assays for a surfactant sensitive biological structure having a lipid bilayer membrane (extracellular vesicles presenting CD9 surface protein). MSD MULTI-ARRAY plates were prepared with capture antibodies against CD9 immobilized on their integrated carbon ink working electrodes. The wells were incubated with a sample containing the extracellular vesicles. The wells were then washed to remove unbound sample and incubated with a solution containing a SULFO-TAG labeled detection antibody against CD9 to bind the labeled detection antibody to captured extracellular vesicles. The wells were then washed to remove unbound detection antibody and read buffer was added. The plates were then analyzed immediately on an MSD SECTOR Imager 6000 ECL plate reader (Time=0), or incubated for 15 minutes prior to the ECL measurement (Time=15). FIG. 7 shows the measured ECL signals. The figure shows that even at Time=0, exposure of the captured extracellular vesicles to the TRITON X-100 containing read buffer led to almost complete loss of signal, presumably due to lysing of the vesicles. By contrast, all the other read buffers gave signals at Time=0 that were within about 5% of each other, except for BRIJ C10, which gave a signal that was still within about 20%. Furthermore, all the read buffers except those containing TRITON X-100, BRIJ C10, BRIJ S10 and BRIJ S20 exhibited less than a 5% change in signal when the plates were incubated in read buffer for 15 minutes, demonstrating that the remaining surfactants (KOLLIPHOR P-407, PLURONIC P-123, PLURONIC L-121, PLURONIC 31R1, TETRONIC 701, 2,4,7,9-tetramethyl-5-decyne-4,7-diol ethoxylate, PEG(18) tridecyl ether, BRIJ L4, BRIJ 58, and TWEEN 20) did not disrupt the captured extracellular vesicles or cause dissociation of the bound SULFO-TAG labeled detection antibody.

The read buffer formulations were very stable; accelerated stability testing of these formulations at 50° C. in the dark showed minimal or no significant change in their performance in most cases, except for the TWEEN 20, PLURONIC 31R1, and TETRONIC 701 formulation which produced about 25% less specific signal after exposure to this temperature for 220 days. The formulations were also robust to changes in the surfactant concentration. FIG. 8 shows that changing the concentration of PEG(18) tridecyl ether between 0.5 and 4 mM had no significant effect on specific ECL signal in the CD9 extracellular vesicle assay, or on the stability of the captured binding reaction products to 15 minutes incubation in the read buffers.

Example V

Immunoassay Off-Rates

Read buffer containing TPA (MSD T2X) and BDEA were tested in an antibody screening experiment for different capture and detection antibodies for various analytes. FIGS. 9A-9D show the average % ECL loss, which is indicative of the off-rate between the antibody and analyte (e.g., between the capture antibody and/or the detection antibody and the analyte), for antibody screens to sRange (FIG. 9A), IL-9 (Figure PB), Kim-1 (FIG. 9C), and MIG (FIG. 9D). In each of the antibody screens, BDEA read buffer had reduced. % ECL loss compared with TPA read buffer, demonstrating that BDEA read buffer can reduce antibody-analyte off-rate relative to TPA read buffer.

FIGS. 10A-10C further demonstrate the improvement in antibody-analyte off-rate with BDEA compared with TPA read buffer in multiplex panel experiments with the analytes IL-13 (FIG. 10A), MDC (FIG. 10B), and TNF-$\beta$ (FIG. 10C). In each of the experiments, BDEA read buffer showed a reduction in the antibody-analyte off-rate, while non-specific background signal (NSB) with BDEA read buffer was either comparable or improved relative to TPA read buffer.

Example VI

Extracellular Vesicle Assays

TPA read buffer (MSD T1X) and BDEA read buffer containing varying concentrations of TRITON X-100 were tested for performance in an intact extracellular vesicle (EV) assay. The EV assay signal change for each buffer type and TRITON X-100 concentration was measured.

Results are shown in FIG. 11A. With MSD T1X, assay performance improved as the concentration of TRITON X-100 was decreased from 0.1% to 0.01%. The MSD T1X assay performance declined as TRITON X-100 concentration was further decreased from 0.01% to 0%. BDEA read buffer with 0.1% TRITON X-100 had low assay performance, while BDEA read buffer with 0% TRITON X-100 had the best assay performance out of all the tested buffer types and TRITON X-100 concentrations.

BDEA read buffer containing a surfactant that does not lyse EVs, was tested for assay performance variability, Titration curves using known concentrations of CD8+EVs were generated for two different lots of the non-TRITON BDEA read buffer. Results are shown in FIG. 11B. The two tested lots of the non-TRITON BDEA read buffer had very similar titration curves, indicating low lot-to-lot variability in performance.

7. INCORPORATION OF REFERENCES

The present disclosure is not to be limited in scope by the specific embodiments described herein. Indeed, various modifications of the disclosure in addition to those described herein will become apparent to those skilled in the art from the foregoing description and accompanying figures. Such modifications are intended to fall within the scope of the claims. Various publications are cited herein, the disclosures of which are incorporated by reference in their entireties.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. A composition comprising:
   (i) about 100 mM to about 175 mM N-butyldiethanolamine (BDEA);
   (ii) about 600 mM to about 1200 mM of at least one salt; and
   (iii) about 100 mM to about 300 mM of at least one pH buffering component,
   wherein the composition further comprises a surfactant, wherein the surfactant is PEG(18) tridecyl ether.

2. The composition of claim 1, wherein the concentration of BDEA is about 125 mM to about 175 mM.

3. The composition of claim 2, wherein the concentration of BDEA is about 150 mM.

4. The composition of claim 1, wherein the at least one salt comprises chloride ion.

5. The composition of claim 4, wherein the at least one salt comprises NaCl, KCl, LiCl or a combination thereof.

6. The composition of claim 5, wherein the at least one salt comprises NaCl and KCl.

7. The composition of claim 6, wherein the concentration of NaCl is about 800 mM and the concentration of KCl is about 50 mM.

8. The composition of claim 1, wherein the pH buffering component is tris(hydroxymethyl)aminomethane (Tris), phosphate, HEPES, glycylglycine, borate, acetate, citrate, or a combination thereof.

9. The composition of claim 8, wherein the pH buffering component is Tris.

10. The composition of claim 1, wherein the concentration of the pH buffering component is about 150 mM to about 250 mM.

11. The composition of claim 1, further comprising TRITON X 100.

12. The composition of claim 1, wherein the concentration of the PEG(18) tridecyl ether is about 0.2 mM to about 10 mM.

13. The composition of claim 11, wherein the concentration of the TRITON X-100 is about 0.2 mM to about 10 mM.

14. The composition of claim 1, wherein:
   (i) the concentration of BDEA is about 150 mM;
   (ii) the at least one salt comprises a concentration of about 850 mM; and
   (iii) the concentration of the pH buffering component is about 200 mM.

15. The composition of claim 14, wherein the at least one salt comprises NaCl and KCl.

16. A composition comprising: (i) about 150 mM BDEA; (ii) about 800 mM NaCl; (iii) about 50 mM KCl; (iv) about 1 mM PEG(18) tridecyl ether; (v) about 200 mM Tris-HCl; and (vi) HCl.

* * * * *